US009033919B2

(12) United States Patent
Wang

(10) Patent No.: US 9,033,919 B2
(45) Date of Patent: *May 19, 2015

(54) MEDICAL DEVICE RAPID DRUG RELEASING COATINGS COMPRISING OILS, FATTY ACIDS, AND/OR LIPIDS

(71) Applicant: Lutonix, Inc., New Hope, MN (US)

(72) Inventor: Lixiao Wang, Medina, MN (US)

(73) Assignee: Lutonix, Inc., New Hope, MN (US)

( * ) Notice: Subject to any disclaimer, the term of this patent is extended or adjusted under 35 U.S.C. 154(b) by 121 days.

This patent is subject to a terminal disclaimer.

(21) Appl. No.: 13/846,104

(22) Filed: Mar. 18, 2013

(65) Prior Publication Data

US 2013/0197435 A1 Aug. 1, 2013

Related U.S. Application Data

(63) Continuation of application No. 12/123,951, filed on May 20, 2008, now Pat. No. 8,414,526, which is a continuation-in-part of application No. 11/942,452, filed on Nov. 19, 2007, now Pat. No. 8,414,909.

(60) Provisional application No. 60/860,084, filed on Nov. 20, 2006, provisional application No. 60/880,742, filed on Jan. 17, 2007, provisional application No. 60/897,427, filed on Jan. 25, 2007, provisional application No. 60/903,529, filed on Feb. 26, 2007, provisional application No. 60/926,850, filed on Apr. 30, 2007, provisional application No. 60/904,473, filed on Mar. 2, 2007, provisional application No. 60/981,380, filed on Oct. 19, 2007, provisional application No. 60/981,384, filed on Oct. 19, 2007.

(51) Int. Cl.

| | |
|---|---|
| ***A61M 31/00*** | (2006.01) |
| ***A61L 29/16*** | (2006.01) |
| ***A61K 31/337*** | (2006.01) |
| ***A61K 31/436*** | (2006.01) |
| ***A61L 31/16*** | (2006.01) |

(52) U.S. Cl.

CPC ............... *A61L 29/16* (2013.01); *A61K 31/337* (2013.01); *A61K 31/436* (2013.01); *A61L 31/16* (2013.01); *A61L 2300/22* (2013.01); *A61L 2300/416* (2013.01); *A61L 2300/802* (2013.01)

(58) Field of Classification Search

CPC .............. A61K 31/337; A61K 31/436; A61K 2300/00; A61L 29/16; A61L 31/16; A61L 2300/22; A61L 2300/416; A61L 2300/802

See application file for complete search history.

(56) References Cited

U.S. PATENT DOCUMENTS 3,929,992 A 12/1975 Sehgal et al.
3,993,749 A 11/1976 Sehgal et al.
4,316,885 A 2/1982 Rakhit et al.
4,364,921 A 12/1982 Speck et al.
4,921,483 A 5/1990 Wijay et al.
5,023,262 A 6/1991 Caufield et al.
5,023,263 A 6/1991 Von Burg et al.
5,023,264 A 6/1991 Caufield et al.
5,026,607 A 6/1991 Kiezulas et al.
5,061,738 A 10/1991 Solomon et al.
5,080,899 A 1/1992 Sturm et al.
5,092,841 A 3/1992 Spears et al.
5,100,883 A 3/1992 Schiehser et al.
5,102,402 A 4/1992 Dror et al.
5,102,876 A 4/1992 Caufield et al.
5,118,677 A 6/1992 Caufield et al.
5,118,678 A 6/1992 Kao et al.
5,120,322 A 6/1992 Davis et al.
5,120,725 A 6/1992 Kao et al.
5,120,726 A 6/1992 Failli et al.
5,120,727 A 6/1992 Kao et al.
5,120,842 A 6/1992 Failli
5,130,307 A 7/1992 Failli et al.
5,135,516 A 8/1992 Sahatjian et al.
5,138,051 A 8/1992 Hughes et al.

(Continued)

FOREIGN PATENT DOCUMENTS

DE 10115740 A1 10/2002
EP 1539267 A2 6/2005

(Continued)

OTHER PUBLICATIONS

Hershberger et al ("Calcitriol (1,25-dihydroxy cholecalciferol) Enhances Paclitaxel Antitumor Activity in Vitro and in Vivo and Accelerates Paclitaxel- Induced Apoptosis," Clin. Can. Res. 7:1043-1051 (Apr. 2001)).*

USPTO Final Rejection mailed Aug. 12, 2014 in reference to co-pending U.S. Appl. No. 13/846,143, filed Mar. 18, 2013.

USPTO Final Rejection mailed Aug. 6, 2014 in reference to co-pending U.S. Appl. No. 13/846,163, filed Mar. 18, 2013.

USPTO Non Final Rejection mailed Aug. 29, 2014 in reference to co-pending U.S. Appl. No. 13/803,419, filed Mar. 14, 2013.

USPTO Final Rejection mailed Aug. 5, 2014 in reference to co-pending U.S. Appl. No. 13/846,078, filed Mar. 18, 2013.

(Continued)

*Primary Examiner* — Suzanne Ziska

(74) *Attorney, Agent, or Firm* — Dinsmore & Shohl LLP

(57) ABSTRACT

The invention relates to a coated medical device for rapid delivery of a therapeutic agent to a tissue in seconds to minutes. The medical device has a layer overlying the exterior surface of the medical device. The layer contains a therapeutic agent, at least one of an oil, a fatty acid, and a lipid, and an additive. In certain embodiments, the additive has a hydrophilic part and a drug affinity part, wherein the drug affinity part is at least one of a hydrophobic part, a part that has an affinity to the therapeutic agent by hydrogen bonding, a part that has an affinity to the therapeutic agent by charge, and a part that has an affinity to the therapeutic agent by van der Waals interactions. In embodiments, the additive is at least one of a surfactant and a chemical compound. In further embodiments, the chemical compound is water-soluble.

20 Claims, 2 Drawing Sheets

(56) References Cited

U.S. PATENT DOCUMENTS 5,151,413 A 9/1992 Caufield et al.
5,162,333 A 11/1992 Failli et al.
5,164,299 A 11/1992 Lambert
5,164,399 A 11/1992 Failli et al.
5,177,203 A 1/1993 Failli et al.
5,193,447 A 3/1993 Lucas et al.
5,194,447 A 3/1993 Kao et al.
5,196,596 A 3/1993 Abatjoglou
5,199,951 A 4/1993 Spears et al.
5,221,670 A 6/1993 Caufield et al.
5,221,740 A 6/1993 Hughes et al.
5,233,036 A 8/1993 Hughes et al.
5,252,579 A 10/1993 Skotnicki et al.
5,254,089 A 10/1993 Wang
5,260,300 A 11/1993 Hu et al.
5,262,423 A 11/1993 Kao et al.
5,269,770 A 12/1993 Conway et al.
5,302,584 A 4/1994 Kao et al.
5,304,121 A 4/1994 Sahatjian
5,324,261 A 6/1994 Amundson et al.
5,346,893 A 9/1994 Failli et al.
5,349,060 A 9/1994 Kao et al.
5,362,718 A 11/1994 Skotnicki et al.
5,370,614 A 12/1994 Amundson et al.
5,373,014 A 12/1994 Failli et al.
5,378,696 A 1/1995 Caufield et al.
5,378,836 A 1/1995 Kao et al.
5,380,298 A 1/1995 Zabetakis et al.
5,380,299 A 1/1995 Fearnot et al.
5,385,908 A 1/1995 Nelson et al.
5,385,909 A 1/1995 Nelson et al.
5,385,910 A 1/1995 Ocain et al.
5,387,680 A 2/1995 Nelson et al.
5,389,639 A 2/1995 Failli et al.
5,391,730 A 2/1995 Skotnicki et al.
5,411,967 A 5/1995 Kao et al.
5,441,759 A 8/1995 Crouther et al.
5,446,048 A 8/1995 Failli et al.
5,463,048 A 10/1995 Skotnicki et al.
5,464,650 A 11/1995 Berg et al.
5,480,988 A 1/1996 Failli et al.
5,480,989 A 1/1996 Kao et al.
5,482,945 A 1/1996 Armstrong et al.
5,489,680 A 2/1996 Failli et al.
5,490,839 A 2/1996 Wang et al.
5,491,231 A 2/1996 Nelson et al.
5,496,276 A 3/1996 Wang et al.
5,504,091 A 4/1996 Molnar et al.
5,504,092 A 4/1996 Nilsson et al.
5,504,204 A 4/1996 Failli et al.
5,508,399 A 4/1996 Kao et al.
5,509,899 A 4/1996 Fan et al.
5,516,781 A 5/1996 Morris et al.
5,525,348 A 6/1996 Whitbourne et al.
5,525,610 A 6/1996 Caufield et al.
5,530,007 A 6/1996 Kao et al.
5,530,121 A 6/1996 Kao et al.
5,532,355 A 7/1996 Skotnicki et al.
5,536,729 A 7/1996 Waranis et al.
5,559,121 A 9/1996 Harrison et al.
5,559,227 A 9/1996 Failli et al.
5,563,145 A 10/1996 Failli et al.
5,563,146 A 10/1996 Morris et al.
5,567,709 A 10/1996 Skotnicki et al.
5,573,518 A 11/1996 Haaga et al.
5,599,307 A 2/1997 Bacher et al.
5,607,463 A 3/1997 Schwartz et al.
5,609,629 A 3/1997 Fearnot et al.
5,616,608 A 4/1997 Kinsella et al.
5,632,772 A 5/1997 Alcime et al.
5,674,192 A 10/1997 Sahatjian et al.
5,674,287 A 10/1997 Slepian et al.
5,679,400 A 10/1997 Tuch
5,693,034 A 12/1997 Buscemi et al.
5,698,582 A 12/1997 Bastart et al.
5,702,754 A 12/1997 Zhong et al.
5,716,981 A 2/1998 Hunter et al.
5,733,925 A 3/1998 Kunz et al.
5,738,901 A 4/1998 Wang et al.
5,752,930 A 5/1998 Rise et al.
5,766,158 A 6/1998 Opolski
5,776,184 A 7/1998 Tuch
5,776,943 A 7/1998 Christians et al.
5,780,462 A 7/1998 Lee et al.
5,797,887 A 8/1998 Rosen et al.
5,807,306 A 9/1998 Shapland et al.
5,824,049 A 10/1998 Ragheb et al.
5,827,289 A 10/1998 Reiley et al.
5,843,089 A 12/1998 Sahatjian et al.
5,865,814 A 2/1999 Tuch
5,868,719 A 2/1999 Tsukernik
5,869,127 A 2/1999 Zhong
5,873,904 A 2/1999 Ragheb et al.
5,879,697 A 3/1999 Ding et al.
5,893,840 A 4/1999 Hull et al.
5,919,145 A 7/1999 Sahatjian et al.
5,919,570 A 7/1999 Hostettler et al.
5,922,730 A 7/1999 Hu et al.
5,947,977 A 9/1999 Slepian et al.
5,954,706 A 9/1999 Sahatjian
5,977,163 A 11/1999 Li et al.
5,981,568 A 11/1999 Kunz et al.
5,985,325 A 11/1999 Nagi
5,989,591 A 11/1999 Nagi
6,015,809 A 1/2000 Zhu et al.
6,039,721 A 3/2000 Johnson et al.
6,042,875 A 3/2000 Ding et al.
6,046,230 A 4/2000 Chung et al.
6,050,980 A 4/2000 Wilson
6,056,722 A 5/2000 Jayaraman et al.
6,074,659 A 6/2000 Kunz et al.
6,096,070 A 8/2000 Ragheb et al.
6,120,904 A 9/2000 Hostettler et al.
6,129,705 A 10/2000 Grantz
6,143,037 A 11/2000 Goldstein et al.
6,146,358 A 11/2000 Rowe
6,176,849 B1 1/2001 Yang et al.
6,218,016 B1 4/2001 Tedeschi et al.
6,221,467 B1 4/2001 Nazarova et al.
6,228,393 B1 5/2001 DiCosmo et al.
6,248,363 B1 6/2001 Patel et al.
6,261,630 B1 7/2001 Nazarova et al.
6,280,411 B1 8/2001 Lennox
6,294,192 B1 9/2001 Patel et al.
6,299,604 B1 10/2001 Ragheb et al.
6,299,980 B1 10/2001 Shah et al.
6,306,144 B1 10/2001 Sydney et al.
6,306,166 B1 10/2001 Barry et al.
6,312,406 B1 11/2001 Jayaraman
6,328,970 B1 12/2001 Molnar-Kimber et al.
6,331,547 B1 12/2001 Zhu et al.
6,335,029 B1 1/2002 Kamath et al.
6,364,856 B1 4/2002 Ding et al.
6,364,893 B1 4/2002 Sahatjian et al.
6,369,039 B1 4/2002 Palasis et al.
6,395,326 B1 5/2002 Castro et al.
6,409,716 B1 6/2002 Sahatjian et al.
6,419,692 B1 7/2002 Yang et al.
6,432,973 B1 8/2002 Zhu et al.
6,443,941 B1 9/2002 Slepian et al.
6,444,324 B1 9/2002 Yang et al.
6,458,138 B1 10/2002 Sydney et al.
6,506,408 B1 1/2003 Palasis
6,524,274 B1 2/2003 Rosenthal et al.
6,528,150 B2 3/2003 Nazarova et al.
6,544,544 B2 4/2003 Hunter et al.
6,571,125 B2 5/2003 Thompson
6,576,224 B1 6/2003 Osbakken et al.
6,589,215 B2 7/2003 Yang et al.
6,589,546 B2 7/2003 Kamath et al.
6,592,548 B2 7/2003 Jayaraman
6,610,035 B2 8/2003 Yang et al.
6,616,650 B1 9/2003 Rowe
6,656,156 B2 12/2003 Yang et al.

(56) References Cited

U.S. PATENT DOCUMENTS 6,677,357 B2 1/2004 Zhu et al.
6,680,330 B2 1/2004 Zhu et al.
6,682,545 B1 1/2004 Kester
6,699,272 B2 3/2004 Slepian et al.
6,730,064 B2 5/2004 Ragheb et al.
6,774,278 B1 8/2004 Ragheb et al.
6,890,339 B2 5/2005 Sahatjian et al.
6,890,546 B2 5/2005 Mollison et al.
6,893,431 B2 5/2005 Naimark et al.
6,899,731 B2 5/2005 Li et al.
6,918,869 B2 7/2005 Shaw et al.
6,921,390 B2 7/2005 Bucay-Couto et al.
6,939,320 B2 9/2005 Lennox
6,958,153 B1 10/2005 Ormerod et al.
6,991,809 B2 1/2006 Anderson
6,997,949 B2 2/2006 Tuch
7,008,411 B1 3/2006 Mandrusov et al.
7,025,752 B2 4/2006 Rice et al.
7,048,714 B2 5/2006 Richter
7,056,550 B2 6/2006 Davila et al.
7,060,051 B2 6/2006 Palasis
7,066,904 B2 6/2006 Rosenthal et al.
7,077,859 B2 7/2006 Sirhan et al.
7,108,684 B2 9/2006 Farnan
7,144,419 B2 12/2006 Cheng et al.
7,153,957 B2 12/2006 Chew et al.
7,160,317 B2 1/2007 Mc Hale et al.
7,163,555 B2 1/2007 Dinh
7,172,619 B2 2/2007 Richter
7,175,873 B1 2/2007 Roorda et al.
7,176,261 B2 2/2007 Tijsma et al.
7,179,251 B2 2/2007 Palasis
7,198,637 B2 4/2007 Deshmukh et al.
7,208,009 B2 4/2007 Richter
7,214,198 B2 5/2007 Greco et al.
7,226,586 B2 6/2007 Fitzhugh et al.
7,232,573 B1 6/2007 Ding
7,235,096 B1 6/2007 Van Tassel et al.
7,244,444 B2 7/2007 Bates
7,247,313 B2 7/2007 Roorda et al.
7,282,213 B2 10/2007 Schroeder et al.
7,285,304 B1 10/2007 Hossainy et al.
7,292,885 B2 11/2007 Scott et al.
7,294,329 B1 11/2007 Ding
7,306,580 B2 12/2007 Paul et al.
7,507,433 B2 3/2009 Weber
7,524,527 B2 4/2009 Stenzel
7,547,294 B2 6/2009 Seward
8,241,249 B2 8/2012 Wang
8,244,344 B2 8/2012 Wang
8,366,660 B2 2/2013 Wang
8,366,662 B2 2/2013 Wang
8,403,910 B2 3/2013 Wang
8,404,300 B2 3/2013 Wang
8,414,525 B2 4/2013 Wang
8,414,526 B2 4/2013 Wang
8,414,909 B2 4/2013 Wang
8,414,910 B2 4/2013 Wang
8,425,459 B2 4/2013 Wang
8,430,055 B2 4/2013 Wang et al.
2001/0002435 A1 5/2001 Berg et al.
2001/0018072 A1 8/2001 Unger
2001/0034363 A1 10/2001 Li et al.
2002/0010419 A1 1/2002 Jayaraman
2002/0039594 A1 4/2002 Unger
2002/0077684 A1 6/2002 Clemens et al.
2002/0082552 A1 6/2002 Ding et al.
2002/0095114 A1 7/2002 Palasis
2002/0098278 A1 7/2002 Bates et al.
2002/0099332 A1 7/2002 Slepian et al.
2002/0102280 A1 8/2002 Anderson
2002/0138048 A1 9/2002 Tuch
2002/0151844 A1 10/2002 Yang et al.
2002/0183380 A1 12/2002 Hunter
2002/0192280 A1 12/2002 Hunter et al.
2003/0004209 A1 1/2003 Hunter et al.
2003/0045587 A1 3/2003 Anderson
2003/0064965 A1 4/2003 Richter
2003/0100577 A1 5/2003 Zhu et al.
2003/0100886 A1 5/2003 Segal et al.
2003/0100887 A1 5/2003 Scott et al.
2003/0114477 A1 6/2003 Zhu et al.
2003/0114791 A1 6/2003 Rosenthal et al.
2003/0157032 A1 8/2003 Cavaillon et al.
2003/0157161 A1 8/2003 Hunter et al.
2003/0207936 A1 11/2003 Chen
2003/0216699 A1 11/2003 Falotico
2003/0235602 A1 12/2003 Schwarz
2004/0018296 A1 1/2004 Castro et al.
2004/0037886 A1 2/2004 Hsu
2004/0062810 A1 4/2004 Hunter et al.
2004/0073284 A1 4/2004 Bates et al.
2004/0076672 A1 4/2004 Hunter et al.
2004/0077677 A1 4/2004 Ashraf et al.
2004/0087902 A1 5/2004 Richter
2004/0127551 A1 7/2004 Zhang et al.
2004/0156816 A1 8/2004 Anderson
2004/0167152 A1 8/2004 Rubino et al.
2004/0176339 A1 9/2004 Sherman et al.
2004/0197408 A1 10/2004 Gravett
2004/0201117 A1 10/2004 Anderson
2004/0202712 A1 10/2004 Lambert et al.
2004/0219214 A1 11/2004 Gravett et al.
2004/0224001 A1 11/2004 Pacetti et al.
2004/0224003 A1 11/2004 Schultz
2004/0225077 A1 11/2004 Gravett et al.
2004/0230176 A1 11/2004 Shanahan et al.
2004/0258662 A1 12/2004 Gibbons, Jr. et al.
2005/0025802 A1 2/2005 Richard et al.
2005/0038409 A1 2/2005 Segal et al.
2005/0042268 A1 2/2005 Aschkenasy et al.
2005/0049271 A1 3/2005 Benjamin et al.
2005/0054978 A1 3/2005 Segal et al.
2005/0055078 A1 3/2005 Campbell
2005/0080477 A1 4/2005 Sydney et al.
2005/0100580 A1 5/2005 Osborne et al.
2005/0101522 A1 5/2005 Speck et al.
2005/0123582 A1 6/2005 Sung et al.
2005/0152983 A1 7/2005 Ashraf et al.
2005/0159704 A1 7/2005 Scott et al.
2005/0171596 A1 8/2005 Furst et al.
2005/0182361 A1 8/2005 Lennox
2005/0186244 A1 8/2005 Hunter et al.
2005/0191323 A1 9/2005 Chen
2005/0191333 A1 9/2005 Hsu
2005/0192210 A1 9/2005 Rothbard et al.
2005/0209664 A1 9/2005 Hunter et al.
2005/0222191 A1 10/2005 Falotico et al.
2005/0234086 A1 10/2005 Gu et al.
2005/0234087 A1 10/2005 Gu et al.
2005/0234234 A1 10/2005 Gu et al.
2005/0238584 A1 10/2005 Annapragada et al.
2005/0239178 A1 10/2005 Ruppen et al.
2005/0250672 A9 11/2005 Speck et al.
2005/0251249 A1 11/2005 Sahatjian et al.
2005/0256564 A1 11/2005 Yang et al.
2005/0272758 A1 12/2005 Bayever et al.
2005/0278021 A1 12/2005 Bates et al.
2005/0288481 A1 12/2005 DesNoyer et al.
2006/0020243 A1 1/2006 Speck
2006/0020331 A1 1/2006 Bates et al.
2006/0040971 A1 2/2006 Zhu et al.
2006/0045901 A1 3/2006 Weber
2006/0051392 A1 3/2006 Heruth et al.
2006/0052744 A1 3/2006 Weber
2006/0067977 A1* 3/2006 Labrecque et al. ........... 424/426
2006/0094745 A1 5/2006 Ruffolo
2006/0112536 A1 6/2006 Herweck et al.
2006/0121117 A1 6/2006 Hunter et al.
2006/0121545 A1 6/2006 Molnar-Kimber et al.
2006/0127445 A1 6/2006 Hunter et al.
2006/0135549 A1 6/2006 Graziani et al.
2006/0135550 A1 6/2006 Graziani et al.
2006/0165753 A1 7/2006 Richard

(56) References Cited

U.S. PATENT DOCUMENTS

2006/0183766 A1 8/2006 Boni et al.
2006/0184236 A1 8/2006 Jones et al.
2006/0188543 A1 8/2006 Feng
2006/0199834 A1 9/2006 Zhu
2006/0199954 A1 9/2006 Shaw et al.
2006/0224237 A1 10/2006 Furst et al.
2006/0230476 A1 10/2006 Atanasoska et al.
2006/0240113 A1 10/2006 Hunter et al.
2006/0257444 A1 11/2006 Tropsha et al.
2006/0257445 A1 11/2006 Tropsha et al.
2006/0282114 A1 12/2006 Barone
2007/0003629 A1 1/2007 Hunter et al.
2007/0003630 A1 1/2007 Hunter et al.
2007/0020308 A1 1/2007 Richard et al.
2007/0020380 A1 1/2007 Ding
2007/0032694 A1 2/2007 Dinkelborg et al.
2007/0050010 A1 3/2007 Bates et al.
2007/0059434 A1 3/2007 Roorda et al.
2007/0065484 A1 3/2007 Chudzik et al.
2007/0073385 A1 3/2007 Schaeffer et al.
2007/0077347 A1 4/2007 Richter
2007/0078446 A1 4/2007 Lavelle
2007/0078513 A1 4/2007 Campbell
2007/0117925 A1 5/2007 Strickler et al.
2007/0128118 A1 6/2007 Yu et al.
2007/0142772 A1 6/2007 Deshmukh et al.
2007/0142905 A1 6/2007 Hezi-Yamit et al.
2007/0150043 A1 6/2007 Richter
2007/0150047 A1 6/2007 Ruane et al.
2007/0161967 A1 7/2007 Fischer et al.
2007/0162103 A1 7/2007 Case et al.
2007/0167735 A1 7/2007 Zhong et al.
2007/0168012 A1 7/2007 Ragheb et al.
2007/0184083 A1 8/2007 Coughlin
2007/0190103 A1 8/2007 Hossainy et al.
2007/0191934 A1 8/2007 Blakstvedt et al.
2007/0198080 A1 8/2007 Ding et al.
2007/0212386 A1 9/2007 Patravale et al.
2007/0212394 A1 9/2007 Reyes et al.
2007/0218246 A1 9/2007 Ding
2007/0219642 A1 9/2007 Richter
2007/0225799 A1 9/2007 Doty
2007/0237803 A1 10/2007 Cheng et al.
2007/0244284 A1 10/2007 Cheng et al.
2007/0244548 A1 10/2007 Myers et al.
2007/0264307 A1 11/2007 Chen et al.
2007/0265565 A1 11/2007 Johnson
2007/0276466 A1 11/2007 Lavelle et al.
2007/0282422 A1 12/2007 Biggs et al.
2007/0286814 A1 12/2007 Sawant
2007/0298069 A1 12/2007 Bucay-Couto et al.
2008/0021385 A1 1/2008 Barry et al.
2008/0038307 A1 2/2008 Hoffmann
2008/0082552 A1 4/2008 Krishnaswamy
2008/0102033 A1 5/2008 Speck et al.
2008/0102034 A1 5/2008 Speck et al.
2008/0114331 A1 5/2008 Holman et al.
2008/0118544 A1 5/2008 Wang
2008/0140002 A1 6/2008 Ramzipoor et al.
2008/0175887 A1 7/2008 Wang
2008/0194494 A1 8/2008 Martinez et al.
2008/0215137 A1 9/2008 Epstein et al.
2008/0255508 A1 10/2008 Wang
2008/0255509 A1 10/2008 Wang
2008/0255510 A1 10/2008 Wang
2008/0255658 A1 10/2008 Cook et al.
2008/0262412 A1 10/2008 Atanasoska et al.
2008/0274159 A1 11/2008 Schultz
2008/0274266 A1 11/2008 Davis et al.
2008/0276935 A1 11/2008 Wang
2008/0317827 A1 12/2008 Wright et al.
2009/0010987 A1 1/2009 Parker et al.
2009/0011116 A1 1/2009 Herweck et al.
2009/0047414 A1 2/2009 Corbeil et al.
2009/0069883 A1 3/2009 Ding et al.
2009/0076448 A1 3/2009 Consigny et al.
2009/0098176 A1 4/2009 Helmus et al.
2009/0105686 A1 4/2009 Snow et al.
2009/0105687 A1 4/2009 Deckman et al.
2009/0136560 A1 5/2009 Bates et al.
2009/0181937 A1 7/2009 Faucher et al.
2009/0182273 A1 7/2009 Johnson
2009/0187144 A1 7/2009 Jayaraman
2009/0208552 A1 8/2009 Faucher et al.
2009/0215882 A1 8/2009 Bouzada et al.
2009/0227948 A1 9/2009 Chen et al.
2009/0227949 A1 9/2009 Knapp et al.
2009/0238854 A1 9/2009 Pacetti et al.
2009/0246252 A1 10/2009 Arps et al.
2009/0324682 A1 12/2009 Popowski
2010/0030183 A1 2/2010 Toner et al.
2010/0055294 A1 3/2010 Wang et al.
2010/0063570 A1 3/2010 Pacetti et al.
2010/0068170 A1 3/2010 Michal et al.
2010/0068238 A1 3/2010 Managoli
2010/0069838 A1 3/2010 Weber et al.
2010/0069879 A1 3/2010 Michal et al.
2010/0081992 A1 4/2010 Ehrenreich et al.
2010/0087783 A1 4/2010 Weber et al.
2010/0179475 A1 7/2010 Hoffmann et al.
2010/0198150 A1 8/2010 Michal et al.
2010/0198190 A1 8/2010 Michal et al.
2010/0209472 A1 8/2010 Wang
2010/0272773 A1 10/2010 Kangas et al.
2010/0285085 A1 11/2010 Stankus et al.
2010/0324645 A1 12/2010 Stankus et al.
2010/0331816 A1 12/2010 Dadino et al.
2011/0054396 A1 3/2011 Kangas et al.
2011/0060275 A1 3/2011 Christiansen
2011/0129514 A1 6/2011 Hossainy et al.
2011/0137243 A1 6/2011 Hossainy et al.
2011/0143014 A1 6/2011 Stankus et al.
2011/0144577 A1 6/2011 Stankus et al.
2011/0144578 A1 6/2011 Pacetti et al.
2011/0152906 A1 6/2011 Escudero et al.
2011/0152907 A1 6/2011 Escudero et al.
2011/0159169 A1 6/2011 Wang
2011/0160658 A1 6/2011 Wang
2011/0160660 A1 6/2011 Wang
2011/0166548 A1 7/2011 Wang
2011/0178503 A1 7/2011 Kangas
2011/0190863 A1 8/2011 Ostroot et al.
2012/0029426 A1 2/2012 Wang
2012/0035530 A1 2/2012 Wang
2013/0189190 A1 7/2013 Wang
2013/0189329 A1 7/2013 Wang
2013/0197431 A1 8/2013 Wang
2013/0197434 A1 8/2013 Wang
2013/0197435 A1 8/2013 Wang
2013/0197436 A1 8/2013 Wang

FOREIGN PATENT DOCUMENTS

EP 1118325 B2 1/2006
EP 1649853 A3 11/2006
EP 1372737 B8 12/2006
EP 1666071 B1 8/2007
EP 1666070 B1 9/2007
EP 1857127 A1 11/2007
EP 1539266 B1 4/2008
EP 1913962 A1 4/2008
EP 1510220 B1 7/2008
EP 1576970 B1 3/2010
EP 1669092 B1 3/2010
EP 1970185 A3 11/2010
EP 1586338 B1 1/2011
EP 2127617 A4 9/2011
EP 1468660 B1 12/2011
WO 2004006976 A1 1/2004
WO 2004026357 A1 4/2004
WO 2004028582 A1 4/2004
WO 2004028610 A3 6/2004
WO 2005011769 A3 4/2005
WO 2006023859 A1 3/2006

(56) References Cited

FOREIGN PATENT DOCUMENTS

| | | | |
|---|---|---|---|
| WO | 2006101573 | A1 | 9/2006 |
| WO | 2006124647 | A1 | 11/2006 |
| WO | 2006081210 | A3 | 2/2007 |
| WO | 2007047416 | A3 | 11/2007 |
| WO | 2007079560 | A3 | 12/2007 |
| WO | 2007134239 | A3 | 1/2008 |
| WO | 2007149161 | A3 | 4/2008 |
| WO | 2008114585 | A1 | 9/2008 |
| WO | 2007139931 | A3 | 10/2008 |
| WO | 2008063576 | A3 | 2/2009 |
| WO | 2008003298 | A3 | 7/2009 |
| WO | 2008086794 | A3 | 1/2010 |

OTHER PUBLICATIONS

Baumbach et al., "Local Drug Delivery: Impact of Pressure Substance Characteristics, and Stenting on Drug Transfer Into the Arterial Wall," Catheterization and Cardiovascular Interventions, vol. 47, pp. 102-106 (1999).

Charles et al., "Ceramide-Coated Balloon Catheters Limit Neointimal Hyperplasia After Stretch Injury in Carotid Arteries," Circulation Research published by the American Heart Association, 87, pp. 282-288 (2000).

Chun Li, et al, "Synthesis, Biodistribution and Imaging Properties of Indium-111-DTPA-Paclitaxel in Mice Bearing Mammary Tumors," The Journal of Nuclear Medicine, vol. 38, No. 7, Jul. 1997, 1042-1047.

Creel, C.J., et al., "Arterial Paclitaxel Distribution and Deposition", Circ Res, vol. 86, pp. 879-884 (2000).

D. M. Long et al., "Perflurocarbon Compounds As X-Ray Contrast Media in the Lungs," Bulletin de la Societe Internationale De Chirurgie, vol. 2, 1975, 137-141.

D.M. Jackson et al., "Current usage of contract agents, anticoagulant and antiplatelet drugs in angiography and angioplasty in the UK," Department of Diagnostic Radiology, Hammersmith Hospital, London, UK, Clinical Radiology (1995), 50, pp. 699-704.

English Language Abstract for DE 101 15 740, Oct. 2, 2002.

English Language Abstract for EP 1 372 737 A2, Jan. 20, 2004.

English Language Abstract for EP 1 539 266 A1, Jun. 15, 2005.

English Language Abstract for EP 1 539 267, Jun. 15, 2005.

English Language Abstract for EP 1 666 070 A1, Jun. 7, 2006.

English Language Abstract for EP 1 669 092 A1, Jun. 14, 2006.

English Language Abstract for EP 1 857 127, Nov. 21, 2007.

English Language Abstract for WO 02/076509, Oct. 3, 2002.

English Language Abstract for WO 2004/028582, Apr. 8, 2004.

English Language Abstract for WO 2004/028610, Apr. 8, 2004.

English Language Abstract for WO 2008/003298 A2, Jan. 10, 2008.

English Language Abstract for WO 2008/086794 , Jul. 24, 2008.

European Search Report for EP 09156858, Jul. 21, 2009.

European Search Report for EP 09160605, Jul. 20, 2009.

European Search Report for EP 10168411, Nov. 30, 2010.

European Search Report for EP 10168412, Nov. 30, 2010.

European Search Report for EP 10189393, Apr. 4, 2011.

Gyula Ostoros et al., "Fatal Pulmonary Fibrosis Induced Paclitaxel: A Case Report and Review of the Literature," International Journal of Gynecological Cancer, vol. 16, Suppl. 1, Jan. 2006, at pp. 391-393.

Gyula Ostoros et al., "Paclitaxel Induced Pulmonary Fibrosis," Lung Cancer, Elsevier, Amsterdam, NL, vol. 41, Aug. 1, 2003, at p. S280.

Herdeg et al., "Paclitaxel: Ein Chemotherapeuticum zum Restenoseprophylaxe? Experimentell Untersuchungen in vitro and in vivo," Z Kardiol, vol. 89, (2000) 390-397.

Hershberger et al "Calcitriol (1, 25-dihydroxy cholecalciferol) Enhances Paclitaxel Antitumor Activity in Vitro and in Vivo and Accelerates Paclitaxel-Induced Apoptosis," Clin. Can. Res. 7: 1043-1051 (Apr. 2001).

International Search Report for International Application No. PCT/US2007/024116, Nov. 20, 2008.

International Search Report for International Application No. PCT/US2007/024108, Aug. 7, 2008.

International Search Report for International Application No. PCT/US2008/006415, May 20, 2008.

International Search Report for International Application No. PCT/US2008/006348, May 16, 2008.

International Search Report for International Application No. PCT/US2008/006417, May 20, 2008.

International Search Report for International Application No. PCT/US2008/007177, Sep. 16, 2008.

International Search Report for International Application No. PCT/US2008/007177, Dec. 2, 2008.

International Search Report for International Application No. PCT/US2008/006348, Nov. 26, 2008.

International Search Report for International Application No. PCT/US2008/006348, Jan. 28, 2009.

International Search Report for International Application No. PCT/US2008/006415, Nov. 24, 2008.

International Search Report for International Application No. PCT/US2008/006417, Nov. 24, 2008.

International Search Report for International Application No. PCT/US2009/004868, Jan. 4, 2010.

International Search Report for International Application No. PCT/US2009/004868, Jan. 1, 2010.

International Search Report for International Application No. PCT/US2009/ 004868, May 21, 2010.

International Search Report for International Application No. PCT/US2010/028599, Dec. 21, 2010.

J.F. Mitchel et al., "Inhibition of Platelet Deposition and Lysis of Intracoronary Thrombus During Balloon Angioplasty Using Urokinase-Coated Hydrogel Balloons." Circulation 90, (Oct. 1994), pp. 1979-1988.

J.H. Baron, et al., "In vitro evaluation of c7E3-Fab (ReoPro) eluting polymer-coated coronary stents." Cardiovascular Research, 46 (2000) pp. 585-594.

"Literature Alerts", Journal of Microencapsulation, vol. 17, No. 6, pp. 789-799 (2000).

K. Kandarpa et al., "Mural Delivery of Iloprost with Use of Hydrogel-coated Balloon Catheters Suppresses Local Platelet Aggregation." J. Vasc. Interv. Radiol. 8, pp. 997-1004, Nov./Dec. 1997.

K. Kandarpa et al., "Site-specific Delivery of Iloprost during Experimental Angioplasty Suppresses Smooth Muscle Cell Proliferation." J. Vasc. Interv. Radiol. 9, pp. 487-493, (1998).

Ken Iwai, et al., "Use of oily contrast medium for selective drug targeting to tumor: Enhanced therapeutic effect and X-ray image," Cancer Research, 44, 2115-2121, May 1994.

Laure Champion et al., "Brief Communication: Sirolimus-Associated Pneumonitis: 24 Cases in Renal Transplant Recipients," Annals of Internal Medicine, vol. 144, No. 7, Apr. 4, 2006, at pp. 505-509.

Leo, A., et al., "Partition coefficients and their uses." Chem Rev, vol. 71 (6), pp. 525-537 (1971).

Li J. Chiang et al., "Potent inhibition of tumor survival in vivo by β-lapachone plus taxol: Combining drugs imposes different artificial checkpoints," PNAS, vol. 96, No. 23, Nov. 9, 1999, at pp. 13369-13374.

New England Journal of Medicine, 1995, 332: 1004-1014.

Rowinsky, E. K., et al., "Drug therapy: paclitaxel (taxol)", Review Article, N Engl J Med, vol. 332, No. 15, pp. 1004-1014, (1995).

PPD "Evaluation of Butanol-Buffer Distribution Properties of C6-Ceraminde." PPD Project No. 7557-001, Aug. 20, 2008, pp. 1-14.

Prashant N. Chhajed et al., "Patterns of Pulmonary Complications Associated with Sirolimus," Respiration: International Review of Thoracic Diseases, vol. 73, No. 3, Mar. 2006, at pp. 367-374.

Sangster, James, "Octanol-Water Partition Coefficients: Fundamentals and Physical Chemistry", Wiley Series in Solution Chemistry vol. 2, Chichester: John Wiley & Sons, vol. 2, Chapter 1 (1997).

Scheller et al., Paclitaxel Balloon Coating, a Novel Method for Prevention and Therapy of Restenosis, Circulation 2004;110;810-814; originally published online Aug. 9, 2004.

(56) References Cited

OTHER PUBLICATIONS

Seymour R. Halpin SF et al., "Corticosteroid prophylaxis for patients with increased risk of adverse reactions to intravascular contrast agents: a survey of current practice in the UK," Department of Radiology, University Hospital of Wales, Heath Park, Cardiff, Clinical Radiology (1994), 49, pp. 791-795.

Toshimitsu Konno, M.D., et al., "Selective targeting of anti-cancer drug and simultaneous imaging enhancement in solid tumors by arterially administered lipid contrast medium," Cancer 54:2367-2374, 1984.

Yushmanov, et al., "Dipyridamole Interacts with the Polar Part of Cationic Reversed Micelles in Chloroform: 1H NMR and ESR Evidence", J. Colloid Interface Sci., vol. 191(2), pp. 384-390 (1997).

* cited by examiner

MEDICAL DEVICE RAPID DRUG RELEASING COATINGS COMPRISING OILS, FATTY ACIDS, AND/OR LIPIDS

CROSS REFERENCE TO RELATED APPLICATIONS

This application is a continuation of U.S. application Ser. No. 12/123,951, filed May 20, 2008, which is a continuation-in-part of application Ser. No. 11/942,452, filed Nov. 19, 2007, which claims the benefit of priority of U.S. Provisional Application No. 60/860,084, filed on Nov. 20, 2006, U.S. Provisional Application No. 60/880,742, filed Jan. 17, 2007, U.S. Provisional Application No. 60/897,427, filed on Jan. 25, 2007, U.S. Provisional Application No. 60/903,529 filed on Feb. 26, 2007, U.S. Provisional Application No. 60/904,473 filed Mar. 2, 2007, U.S. Provisional Application No. 60/926,850 filed Apr. 30, 2007, U.S. Provisional Application No. 60/981,380 filed Oct. 19, 2007, and U.S. Provisional Application No. 60/981,384 filed Oct. 19, 2007, the disclosures of all of which are incorporated by reference herein.

FIELD OF THE INVENTION

Embodiments of the present invention relate to coated medical devices, and particularly to coated balloon catheters, and their use for rapidly delivering a therapeutic agent to particular tissue or body lumen, for treatment of disease and particularly for reducing stenosis and late lumen loss of a body lumen. Embodiments of the present invention also relate to methods of manufacturing these medical devices, the drug releasing coatings comprising at least one of an oil, a fatty acid, and a lipid provided on these medical devices, the solutions for making those coatings, and methods for treating a body lumen such as the vasculature, including particularly arterial vasculature, for example, using these coated medical devices.

BACKGROUND OF THE INVENTION

It has become increasingly common to treat a variety of medical conditions by introducing a medical device into the vascular system or other lumen within a human or veterinary patient such as the esophagus, trachea, colon, biliary tract, or urinary tract. For example, medical devices used for the treatment of vascular disease include stents, catheters, balloon catheters, guide wires, cannulas and the like. While these medical devices initially appear successful, the benefits are often compromised by the occurrence of complications, such as late thrombosis, or recurrence of disease, such as stenosis (restenosis), after such treatment.

Restenosis, for example, involves a physiological response to the vascular injury caused by angioplasty. Over time, de-endotheliaziation and injury to smooth muscle cells results in thrombus deposition, leukocyte and macrophage infiltration, smooth muscle cell proliferation/migration, fibrosis and extracellular matrix deposition. Inflammation plays a pivotal role linking early vascular injury to the eventual consequence of neointimal growth and lumen compromise. In balloon-injured arteries, leukocyte recruitment is confined to early neutrophil infiltration, while in stented arteries, early neutrophil recruitment is followed by prolonged macrophage accumulation. The widespread use of coronary stents has altered the vascular response to injury by causing a more intense and prolonged inflammatory state, due to chronic irritation from the implanted foreign body, and in the case of drug eluting stents (DES), from insufficient biocompatibility of the polymer coating.

Over the past several years, numerous local drug delivery systems have been developed for the treatment and/or the prevention of restenosis after balloon angioplasty or stenting. Examples include local drug delivery catheters, delivery balloon catheters, and polymeric drug coated stents. Given that many diseases affect a specific local site or organ within the body, it is advantageous to preferentially treat only the affected area. This avoids high systemic drug levels, which may result in adverse side effects, and concentrates therapeutic agents in the local area where they are needed. By treating just the diseased tissue, the total quantity of drug used may be significantly reduced. Moreover, local drug delivery may allow for the use of certain effective therapeutic agents, which have previously been considered too toxic or non-specific to use systemically.

One example of a local delivery system is a drug eluting stent (DES). The stent is coated with a polymer into which drug is impregnated. When the stent is inserted into a blood vessel, the polymer degrades and the drug is slowly released. The slow release of the drug, which takes place over a period of weeks to months, has been reported as one of the main advantages of using DES. However, while slow release may be advantageous in the case where a foreign body, such as a stent, is deployed, which is a source of chronic irritation and inflammation, if a foreign body is not implanted it is instead advantageous to rapidly deliver drug to the vascular tissue at the time of treatment to inhibit inflammation and cellular proliferation following acute injury. Thus, a considerable disadvantage of a DES, or any other implanted medical device designed for sustained release of a drug, is that the drug is incapable of being rapidly released into the vessel.

Additionally, while drug-eluting stents were initially shown to be an effective technique for reducing and preventing restenosis, recently their efficacy and safety have been questioned. A life-threatening complication of the technology, late thrombosis, has emerged as a major concern. Drug eluting stents cause substantial impairment of arterial healing, characterized by a lack of complete re-endothelialization and a persistence of fibrin when compared to bare metal stents (BMS), which is understood to be the underlying the cause of late DES thrombosis. Concerns have also been raised that the polymeric matrix on the stent in which the anti-proliferative drug is embedded might exacerbate inflammation and thrombosis, since the polymers used are not sufficiently biocompatible. These polymeric systems are designed to facilitate long-term sustained release of drug over a period of days, months, or years, not over a period of seconds or minutes. The polymeric drug coatings of medical devices do not release the polymer, which remains on the device even after drug is released. Even if biodegradable polymers are used, polymer and drug are not released at the same time. Rapid release of drug, an intent of embodiments of the present invention, from these polymeric systems is not possible. Thus, combining a therapeutic agent with a polymer in a medical device coating may have significant disadvantages.

Another important limitation of the DES is that the water insoluble drugs are not evenly distributed in the polymeric matrix of the coating. Furthermore, drug and polymer are concentrated on the struts of the stent, but not in gaps between the struts. The non-uniform distribution of drug causes non-uniform drug release to the tissue of the vessel walls. This may cause tissue damage and thrombosis in areas exposed to excess drug and hyperplasia and restenosis areas that are undertreated. Thus, there is a need to improve the uniformity of drug delivery to target tissues by improving drug solubility in coatings of medical devices by increasing the drug's compatibility with carriers in the coatings, such as a polymeric matrix, thereby eliminating or reducing the size of drug crystal particles in the polymeric matrix or other coating to create a uniform drug distribution in the drug coating on the medical device.

Yet another important limitation of the DES is that only a limited amount of an active agent can be loaded into the relatively small surface area of the stent.

Non-stent based local delivery systems, such as balloon catheters, have also been effective in the treatment and prevention of restenosis. The balloon is coated with an active agent, and when the blood vessel is dilated, the balloon is pressed against the vessel wall to deliver the active agent. Thus, when balloon catheters are used, it is advantageous for the drug in the coating to be rapidly released and absorbed by blood vessel tissues. Any component of the coating that inhibits its rapid release, such as a polymer, liposome, or encapsulating particle, is necessarily disadvantageous to the intended use of the balloon catheter, which is inflated for a very brief period of time and then removed from the body.

Hydrophilic drugs, such as heparin, have been reported to be deliverable by polymeric hydrogel coated balloon catheters. However, a polymeric hydrogel coating can not effectively deliver water insoluble drugs (such as paclitaxel and rapamycin), because they can not mix with the hydrogel coating. Even if hydrophobic drug could be incorporated successfully into a hydrogel matrix, drug cannot release through the crosslinked polymer network, which remains on the balloon.

The iodine contrast agent iopromide has been used with paclitaxel to coat balloon catheters and has some success in treatment of restenosis. It was reported that contrast agent improves adhesion of paclitaxel to the balloon surface. Iodinated contrast agents suffer from several well known disadvantages. When used for diagnostic procedures, they may have complication rates of 5-30%. These agents are associated with the risk of bradycardia, ventricular arrthymia, hypotension, heart block, sinus arrest, sinus tachycardia, and fibrillation. Iodine contrast agents may also induce renal failure, and as a result there are significant efforts to remove these contrast agents from the vascular system after diagnostic procedures.

Iodinated X-ray contrast agents are large hydrophilic spherical molecules. They are characterized by an extracellular distribution and rapid glomerular filtration and renal excretion. They are unable to cross membrane lipid bilayers to enter cells of the vasculature because they are large, polar, hydrophilic molecules. They are therefore not optimally effective at carrying hydrophobic drugs such as paclitaxel into cells, and the percent of paclitaxel reported to be taken up by vascular tissue after deployment of these devices is only 5-20%. In addition, the compatability or miscibility of paclitaxel and iopromide is not good, and the integrity and uniformity of the coating is poor. Particles from the coating easily flake off and are lost during handling. These deficiencies adversely affect the amount and uniformity of drug delivered to target tissue. Improved coatings are therefore needed, coatings that not only avoid unnecessary doses of contrast, but that also maintain integrity during handling and more effectively and uniformly deliver drug and facilitate its absorption by tissue.

Alternatively, balloon catheters are reported to have been coated with hydrophobic therapeutic agents that have been encapsulated in particles such as micelles, liposomes, nanoparticles or polymers. Liposomes, which usually contain a core of aqueous solution, and micelles, which do not, have both been reported to be useful for pharmaceutical preparations of water-insoluble drugs for venous injection. However, for purposes of a medical device coating, all of these drug delivery formulations have significant disadvantages: drug loading is poor, and drug release from these preparations is slow.

Oils and lipids mix well with water-insoluble drugs such as paclitaxel or rapamycin, but when micelles or liposomes are then formed by interaction with aqueous media, the particles and particle sizes are relatively unstable, ranging in a broad particle size distribution from several hundred nanometers to several microns in diameter. Several reports suggest that the maximal concentration ratio of drug to lipid that can be stably achieved in these particles is in the range of 0.2 to 0.3; it is often less than 0.1.

Another disadvantage of oil-based liposome formulations is the dependence of drug absorption on the rate and extent of lipolysis. Lipolysis of oil-based triglycerides is difficult and dependent upon many factors, and triglycerides must be digested and drug released in order to be absorbed by diseased tissue. The amount of hydrophobic drug delivered to tissues by these agents will be low, because liposomes and micelles cannot efficiently release hydrophobic drug, which they carry away before it can be absorbed by tissues. Micelles, liposomes, or particles of oils and lipids are therefore not effective at rapidly and efficiently facilitating tissue uptake of drug during a very brief device deployment time, and no report has shown these types of coatings to be effective.

Loading capacity of conventional micelles and liposomes is low. In the absence of other considerations, the highest achievable drug to lipid ratio is advantageous, since high lipid doses may raise concerns of toxicitiy, and it is the drug—not the lipid—that provides the therapeutic benefit, once it is delivered to target tissue. The ratio of drug to lipid in these formulations is often less than 0.1 and almost always less than 0.2-0.3, because a significantly higher concentration of lipid than drug is required in order for the drug to be encapsulated in the particles, miscelles, or liposomes. Formulation stability is highly dependent on drug-lipid interactions that are concentration dependent. "In many studies, a maximum of 3 to 4 mol % drug (with respect to phospholipid) possess stability of sufficient duration as to be clinically useable. [ . . . ] 8 mol % paclitaxel liposomes may be physically stable for 15 min or less"—Preparation and Characterization of Taxane-Containing Liposomes. *Methods Enzymol*. 2005; 391:97-117, p. 101-2. Several attempts to achieve drug to lipid concentration ratios higher than 0.2-0.3 failed (for example, see *PDA J Pharm Sci Technol* 2006 60(3):144-55). These technologies involve forming the drug/lipid particles first and then coating medical devices with the prepared particles. Liposomes, for example, are prepared by first mixing drug and lipid in organic solvent, then removing the organic solvent to form a lipid film or cake, then hydrating with aqueous solution and sonicating.

There are several reports showing that drug release from liposomal, miscellar, or particular oil/lipid formulations occurs very slowly, in the range of days to weeks or months. In addition, the inventor has found that drug release occurs far too slowly from a coating consisting essentially of just oil/lipid and lipophilic drug, because they bind to each other and to the external surface of the medical device so tightly that the drug cannot rapidly elute off the device during several minutes or less of deployment at the target site. This slow-releasing property of prior approaches to drug-oil, drug-fatty acid, and drug-lipid formulations is not desirable in embodiments of the present invention, wherein drug release takes place in the range of seconds to minutes. Thus the technology for oil, fatty acid, and/or lipid formulations needs to be improved significantly in order to be useful in the rapid drug release coatings for medical devices.

Drug that is encapsulated in polymeric particles may take even longer to diffuse from the coating (the reported range is months to years) and will have further difficulty permeating target tissues rapidly. Microspheres formed with polymeric materials, such as polyesters, when used to encapsulate water insoluble drugs, are unable to release the drug until the polymeric material is degraded. Thus, these polymeric microspheres are useful for sustained release of drug over a long period of time but cannot rapidly release drug and facilitate tissue uptake.

Combining drugs and medical devices is a complicated area of technology. It involves the usual formulation challenges, such as those of oral or injectable pharmaceuticals, together with the added challenge of maintaining drug adherence to the medical device until it reaches the target site and subsequently delivering the drug to the target tissues with the desired release and absorption kinetics. Drug coatings of medical devices must also have properties such that they do not crack upon expansion and contraction of the device, for example, of a balloon catheter or a stent. Furthermore, coatings must not impair functional performance such as burst pressure and compliance of balloons or the radial strength of self- or balloon-expanded stents. The coating thickness must also be kept to a minimum, since a thick coating would increase the medical device's profile and lead to poor trackability and deliverability. These coatings generally contain almost no liquid chemicals, which typically are often used to stabilize drugs. Thus, formulations that are effective with pills or injectables might not work at all with coatings of medical device. If the drug releases from the device too easily, it may be lost during device delivery before it can be deployed at the target site, or it may burst off the device during the initial phase of inflation and wash away before being pressed into contact with target tissue of a body lumen wall. If the drug adheres too strongly, the device may be withdrawn before the drug can be released and absorbed by tissues at the target tissues.

Thus, there is still a need to develop improved drug-oil, drug-fatty acid and drug-lipid coatings for medical devices that can be loaded with a higher concentration of therapeutic agent, drug, or other bioactive material and that can rapidly deliver that therapeutic agent directly into a localized tissue area during or following a medical procedure, so as to treat or prevent vascular and nonvascular diseases such as stenosis. The device should be able to quickly release the therapeutic agent during a brief 0.1-2 minute deployment of the device at the target site (not require a prolonged period of deployment), and the therapeutic agent should rapidly permeate the target tissue to treat disease, for example, to relieve stenosis and prevent restenosis and late lumen loss of a body lumen.

There is still a need to develop improved drug-oil, drug-fatty acid, and drug-lipid coatings for medical devices that release drug in seconds to minutes, not in days to months.

SUMMARY OF THE INVENTION

The present inventor has found that coating the exterior surface of a medical device, and particularly of a balloon catheter or a stent, for example, with a layer comprising a lipophilic or water-insoluble therapeutic agent, an additive, and at least one of an oil, a fatty acid, and a lipid, wherein the additive comprises a hydrophilic part and a drug affinity part, wherein the drug affinity part is at least one of a hydrophobic part, a part that has an affinity to the therapeutic agent by hydrogen bonding, and a part that has an affinity to the therapeutic agent by van der Waals interactions, facilitates rapid release of drug in seconds to minutes and solves the problems associated with prior approaches to oil, fatty acid, and lipid coatings discussed above. Surprisingly, the present inventor has found that the at least one additive that has both a hydrophilic part and a drug affinity part and at least one of an oil, fatty acid, and lipid according to embodiments of the present invention, in combination with a lipophilic or water-insoluble therapeutic agent, forms an effective drug delivery coating on a medical device that avoids the disadvantages of conventional oil-based, fatty-acid-based, and lipid-based coating formulations such as slow release, lipolysis dependence, and a very low limit to drug:lipid concentration ratio. Moreover, the coatings according to embodiments of the present invention facilitate rapid drug elution off of the surface of the device and superior permeation of drug into tissues at a disease site to treat disease, for example, to relieve stenosis and to reduce restenosis and late lumen loss of a body lumen. Thus, coatings according to embodiments of the present invention provide an enhanced rate and/or extent of absorption of the hydrophobic therapeutic agent in diseased tissues of the vasculature or other body lumen.

In embodiments of the present invention, the coated device reduces stenosis and late lumen loss of a body lumen.

In embodiments of the present invention, the additive comprises a hydrophilic part and a drug affinity part, wherein the drug affinity part is at least one of a hydrophobic part, a part that has affinity to the therapeutic agent by hydrogen bonding, a part that has affinity to the therapeutic agent by charge, and a part that has affinity to the therapeutic agent by van der Waals interactions. In embodiments of the present invention, the therapeutic agent is lipophilic or water-insoluble.

In one embodiment, the present invention relates to a medical device for delivering a therapeutic agent to a tissue for reducing stenosis and late lumen loss of a body lumen, the device comprising a layer overlying an exterior surface of the medical device. The device includes one of a balloon catheter, a perfusion balloon catheter, infusion catheter such as distal perforated drug infusion tube, a perforated balloon, spaced double balloon, porous balloon, and weeping balloon, a cutting balloon catheter, a scoring balloon catheter, a laser catheter, an atherectomy device, a debulking catheter, a stent, a filter, a stent graft, a covered stent, a patch, a wire, and a valve. Further, the tissue includes tissue of one of coronary vasculature, peripheral vasculature, cerebral vasculature, esophagus, airways, sinus, trachea, colon, biliary tract, urinary tract, prostate, and brain passages.

In one embodiment of the medical device, the layer overlying the exterior surface of the medical device comprises a therapeutic agent, an additive, and at least one of an oil, a fatty acid, and a lipid, wherein the additive comprises a hydrophilic part and a drug affinity part, wherein the drug affinity part is at least one of a hydrophobic part, a part that has an affinity to the therapeutic agent by hydrogen bonding, a part that has an affinity to the therapeutic agent by charge, and a part that has an affinity to the therapeutic agent by van der Waals interactions, wherein the additive is at least one of a surfactant and a chemical compound, and wherein the chemical compound is water-soluble.

In one embodiment, the layer overlying the exterior surface of the medical device consists essentially of the therapeutic agent, the additive, and the at least one of an oil, a fatty acid, and a lipid.

In one embodiment, the layer overlying the exterior surface of the medical device includes a therapeutic agent, an additive, and at least one of an oil, a fatty acid, and a lipid, wherein the additive comprises a hydrophilic part and a drug affinity part, wherein the drug affinity part is at least one of a hydrophobic part, a part that has an affinity to the therapeutic agent by hydrogen bonding, and a part that has an affinity to the therapeutic agent by van der Waals interactions, and the layer does not include a polymer. In one embodiment, the additive in the layer comprising the therapeutic agent, the additive, and the at least one of an oil, fatty acid, and lipid, is an ionic or non-ionic surfactant. In another embodiment, the additive is an aliphatic or aromatic surfactant. In another embodiment, the additive is the chemical compounds with one or more hydroxyl, amino, carbonyl, carboxyl, acid, amide, ester moieties thereof. In another embodiment, the additive is a chemical compound with one or more hydroxyl, amino, carbonyl, carboxyl, acid, amide, or ester moieties with a molecular weight of less than 5,000-10,000, preferably less than 1000-5,000, more preferably less than 750-1,000, or most preferably less than 750. Molecular weight of the additive is preferred to be less than that of the drug to be delivered. Small molecules can diffuse quickly, and they easily release from the surface of the delivery balloon, carrying drug with them. They quickly diffuse away from drug when the drug binds tissue. The molecular weight of the additives can not be too low, however, additives with molecular weight less than 80 are not desirable because they evaporate easily and are not stable components of the coating. In another embodiment, the additive is hydroxyl ketone, hydroxyl lactone, hydroxyl acid, hydroxyl ester, or hydroxylamide. In another embodiment, the additive is gluconolactone or ribonic acid lactone thereof. In yet another embodiment, the additive is chosen from meglumine/lactic acid, meglumine/gentisic acid, meglumine/acetic acid, lactobionic acid, Tween 20/sorbitol, Tween 20/lactobionic acid, Tween 20/sugar or sugar derivatives, and N-octanoyl N-methylglucamine. In another embodiment, the additive is a vitamin or derivative thereof. In another embodiment, the additive is an amino acid or derivative thereof. In another embodiment, the additive is a protein or derivative thereof. In another embodiment, the additive is an albumin. In another embodiment, the additive is soluble in an aqueous solvent and is soluble in an organic solvent. In yet another embodiment, the additive is chosen from sorbitan oleate and sorbitan fatty esters.

In one embodiment, the at least one of an oil, a fatty acid, and a lipid in the layer overlying an exterior of the medical device is chosen from soybean oil, vegetable oil, flower oil, animal oil, marine oil, butterfat, coconut oil, palm oil, olive oil, peanut oil, fish oil, butanoic acid, hexanoic acid, octanoic acid, decanoic acid, dodecanoic acid, tetradecanoic acid, hexadecanoic acid, octadecanoic acid, octadecatrienoic acid, eicosanoic acid, eicosenoic acid, eicosatetraenoic acid, eicosapentaenoic acid, docosahexaenoic acid, tocotrienol, butyric acid, caproic acid, caprylic acid, capric acid, lauric acid, myristic acid, palmitic acid, palmitoleic acid, stearic acid, oleic acid, vaccenic acid, linoleic acid, alpha-linolenic acid, gamma-linolenic acid, behenic acid, erucic acid, lignoceric acid, natural or synthetic phospholipids, mono-, di-, or triacylglycerols, cardiolipin, phosphatidylglycerol, phosphatidic acid, phosphatidylcholine, alpha tocoferol, phosphatidylethanolamine, sphingomyelin, phosphatidylserine, phosphatidylinositol, dimyristoylphosphatidylcholine, dioleoylphosphatidylcholine, dipalmitoylphosphatidylcholine, distearoylphosphatidylcholine, phosphatidylethanolamines phosphatidylglycerols, sphingolipids, prostaglandins, gangliosides, neobee, niosomes, and derivatives thereof.

In one embodiment of the medical device, the additive in the layer overlying an exterior surface of the medical device is at least one of a surfactant and a chemical compound. In one aspect of this embodiment, the chemical compound is chosen from amino alcohols, hydroxyl carboxylic acid, ester, and anhydrides, hydroxyl ketone, hydroxyl lactone, hydroxyl ester, sugar phosphate, sugar sulfate, ethyl oxide, ethyl glycols, amino acids, peptides, proteins, sorbitan, glycerol, polyalcohol, phosphates, sulfates, organic acids, esters, salts, vitamins, combinations of amino alcohol and organic acid, and their substituted molecules. In another embodiment of the medical device, the surfactant is chosen from ionic, nonionic, aliphatic, and aromatic surfactants, PEG fatty esters, PEG omega-3 fatty esters, ether, and alcohols, glycerol fatty esters, sorbitan fatty esters, PEG glyceryl fatty esters, PEG sorbitan fatty esters, sugar fatty esters, PEG sugar esters, and derivatives thereof.

In one embodiment, the additive in the layer overlying an exterior surface of the medical device is a mixture or combination of a surfactant and a chemical compound, wherein the chemical compound has one or more hydroxyl, amino, carbonyl, carboxyl, acid, amide or ester groups. In one aspect of this embodiment, the surfactant is chosen from ionic, nonionic, aliphatic, and aromatic surfactants, PEG fatty esters, PEG omega-3 fatty esters, ether, and alcohols, glycerol fatty esters, sorbitan fatty esters, PEG glyceryl fatty esters, PEG sorbitan fatty esters, sugar fatty esters, PEG sugar esters, and derivatives thereof. In another aspect of this embodiment, the chemical compound having one or more hydroxyl, amino, carbonyl, carboxyl, acid, amide or ester groups is chosen from amino alcohols, hydroxyl carboxylic acid, ester, and anhydrides, hydroxyl ketone, hydroxyl lactone, hydroxyl ester, sugar phosphate, sugar sulfate, ethyl oxide, ethyl glycols, amino acids, peptides, proteins, sorbitan, glycerol, polyalcohol, phosphates, sulfates, organic acids, esters, salts, vitamins, combinations of amino alcohol and organic acid, and their substituted molecules.

In one embodiment the present invention relates to a medical device for delivering a therapeutic agent to a tissue, the device comprising a layer overlying an exterior surface of the medical device, the layer comprising a therapeutic agent, an additive, and at least one of an oil, a fatty acid, and a lipid, wherein the additive comprises a hydrophilic part and a drug affinity part, wherein the drug affinity part is at least one of a hydrophobic part, a part that has an affinity to the agent by charge, and a part that has an affinity to the therapeutic agent by van der Waals interactions, wherein the additive is chosen from p-isononylphenoxypolyglycidol, PEG laurate, PEG oleate, PEG stearate, PEG glyceryl laurate, Tween 20, Tween 40, Tween 60, Tween 80, PEG glyceryl oleate, PEG glyceryl stearate, polyglyceryl laurate, plyglyceryl oleate, polyglyceryl myristate, polyglyceryl palmitate, polyglyceryl-6 laurate, plyglyceryl-6 oleate, polyglyceryl-6 myristate, polyglyceryl-6 palmitate, polyglyceryl-10 laurate, plyglyceryl-10 oleate, polyglyceryl-10 myristate, polyglyceryl-10 palmitate PEG sorbitan monolaurate, PEG sorbitan monolaurate, PEG sorbitan monooleate, PEG sorbitan stearate, PEG oleyl ether, PEG laurayl ether, octoxynol, monoxynol, tyloxapol, sucrose monopalmitate, sucrose monolaurate, decanoyl-N-methylglucamide, n-decyl-β-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucopyranoside, n-heptyl-β-D-thioglucoside, n-hexyl-β-D-glucopyranoside, nonanoyl-N-methylglucamide, n-noyl-β-D-glucopyranoside, octanoyl-N-methylglucamide, n-octyl-β-D-glucopyranoside, octyl-β-D-thioglucopyranoside; cystine, tyrosine, tryptophan, leucine, isoleucine, phenylalanine, asparagine, aspartic acid, glutamic acid, and methionine; acetic anhydride, benzoic anhydride, ascorbic acid, 2-pyrrolidone-5-carboxylic acid, sodium pyrrolidone carboxylate, ethylenediaminetetraacetic dianhydride, maleic and anhydride, succinic anhydride, diglycolic anhydride, glutaric anhydride, acetiamine, benfotiamine, pantothenic acid; cetotiamine; cyclothiamine, dexpanthenol, niacinamide, nicotinic acid, pyridoxal 5-phosphate, nicotinamide ascorbate, riboflavin, riboflavin phosphate, thiamine, folic acid, menadiol diphosphate, menadione sodium bisulfite, menadoxime, vitamin B12, vitamin K5, vitamin K6, vitamin K6, and vitamin U; albumin, immunoglobulins, caseins, hemoglobins, lysozymes, immunoglobins, a-2-macroglobulin, fibronectins, vitronectins, firbinogens, lipases, benzalkonium chloride, benzethonium chloride, docecyl trimethyl ammonium bromide, sodium docecylsulfates, dialkyl methylbenzyl ammonium chloride, and dialkylesters of sodium sulfonsuccinic acid, L-ascorbic acid and its salt, D-glucoascorbic acid and its salt, tromethamine, triethanolamine, diethanolamine, meglumine, glucamine, amine alcohols, glucoheptonic acid, glucomic acid, hydroxyl ketone, hydroxyl lactone, gluconolactone, glucoheptonolactone, glucooctanoic lactone, gulonic acid lactone, mannoic lactone, ribonic acid lactone, lactobionic acid, glucosamine, glutamic acid, benzyl alcohol, benzoic acid, hydroxybenzoic acid, propyl 4-hydroxybenzoate, lysine acetate salt, gentisic acid, lactobionic acid, lactitol, sinapic acid, vanillic acid, vanillin, methyl paraben, propyl paraben, diethylene glycol, triethylene glycol, tetraethylene glycol, xylitol, 2-ethoxyethanol, sugars, galactose, glucose, mannose, xylose, sucrose, lactose, maltose, sorbitol, cyclodextrin, (2-hydroxypropyl)-cyclodextrin, acetaminophen, ibuprofen, retinoic acid, lysine acetate, gentisic acid, catechin, catechin gallate, tiletamine, ketamine, propofol, lactic acids, acetic acid, salts of any of the foregoing organic acids and amines, polyglycidol, glycerols, multiglycerols, and mixtures of the additives, and derivatives thereof.

In another embodiment, the additive in the layer comprising the therapeutic agent, the additive, and the at least one of an oil, a fatty acid, and a lipid, is chosen from Tyloxapol, Octoxynol, oleth, laureth, PEG-glyceryl, monolaurate, PEG-20 monolaurate, PEG 20 monooleate, PEG 20 glyceryl monooleate, Nonoxynol, Nonylphenylpoly(glycidol), Octyl-betha-D-glycopyranoside, and deconoyl-N-methylglucamide.

In another embodiment, the additive in the layer comprising the therapeutic agent, the additive, and the at least one of an oil, a fatty acid, and a lipid is chosen from benzalkonium chloride, benzethonium chloride, docecyl trimethyl ammonium bromide, sodium docecylsulfates, dialkyl methylbenzyl ammonium chloride, and dialkylesters of sodium sulfonsuccinic acid.

In one embodiment, the therapeutic agent in the layer comprising the therapeutic agent, the additive, and the at least one of an oil, a fatty acid, and a lipid, is one of paclitaxel and analogues thereof, rapamycin and analogues thereof, beta-lapachone and analogues thereof, biological vitamin D and analogues thereof, and a mixture of these therapeutic agents. In another embodiment, the therapeutic agent is in combination with a second therapeutic agent, wherein the therapeutic agent is one of paclitaxel, rapamycin, and analogues thereof, and wherein the second therapeutic agent is one of beta-lapachone, biological active vitamin D, and their analogues. In one embodiment, the therapeutic agent is not water-soluble.

In one embodiment, the additive enhances penetration and absorption of the therapeutic agent in tissue. In another embodiment, the additive penetrates tissue, and the therapeutic agent is not water-soluble. In another embodiment, the additive enhances release of the therapeutic agent from the surface of the medical device. In another embodiment, the additive has water and ethanol solubility of at least 1 mg/ml and the therapeutic agent is not water-soluble.

In one embodiment, the concentration of the additive in the layer is from 1 to 20 μg/mm$^2$. In one embodiment, the concentration of the at least one of an oil, a fatty acid, and a lipid in the layer is from 1 to 20 μg/mm$^2$. In one embodiment, the concentration of the therapeutic agent in the layer is from 1 to 20 μg/mm$^2$. In another embodiment, the concentration of the therapeutic agent in the layer is from 2 to 10 μg/mm$^2$.

In one embodiment of the medical device, the device is capable of delivering the therapeutic agent to the tissue in about 0.2 to 10 minutes, or preferably from about 0.1 to 2 minutes. In another embodiment, the device is capable of delivering the therapeutic agent to the tissue in about 0.1 to 1 minute.

In one embodiment, the medical device comprising a layer overlying an exterior surface of the medical device further comprises an adherent layer between the exterior surface of the medical device and the layer. In another embodiment, the device further comprises a top layer overlying the surface of the layer to reduce loss of drug during transit through a body to the tissue. In one aspect of this embodiment, the top layer comprises an additive that is less hydrophilic than the additive in the layer overlying the exterior surface of the medical device, and wherein the additive in the top layer is chosen from p-isononylphenoxypolyglycidol, PEG laurate, Tween 20, Tween 40, Tween 60, PEG oleate, PEG stearate, PEG glyceryl laurate, PEG glyceryl oleate, PEG glyceryl stearate, polyglyceryl laurate, plyglyceryl oleate, polyglyceryl myristate, polyglyceryl palmitate, polyglyceryl-6 laurate, plyglyceryl-6 oleate, polyglyceryl-6 myristate, polyglyceryl-6 palmitate, polyglyceryl-10 laurate, plyglyceryl-10 oleate, polyglyceryl-10 myristate, polyglyceryl-10 palmitate PEG sorbitan monolaurate, PEG sorbitan monolaurate, PEG sorbitan monooleate, PEG sorbitan stearate, PEG oleyl ether, PEG laurayl ether, octoxynol, monoxynol, tyloxapol, sucrose monopalmitate, sucrose monolaurate, decanoyl-N-methylglucamide, n-decyl-β-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucopyranoside, n-heptyl-β-D-thioglucoside, n-hexyl-β-D-glucopyranoside, nonanoyl-N-methylglucamide, n-noyl-β-D-glucopyranoside, octanoyl-N-methylglucamide, n-octyl-β-D-glucopyranoside, octyl-β-D-thioglucopyranoside; cystine, tyrosine, tryptophan, leucine, isoleucine, phenylalanine, asparagine, aspartic acid, glutamic acid, and methionine; acetic anhydride, benzoic anhydride, ascorbic acid, 2-pyrrolidone-5-carboxylic acid, sodium pyrrolidone carboxylate, ethylenediaminetetraacetic dianhydride, maleic and anhydride, succinic anhydride, diglycolic anhydride, glutaric anhydride, acetiamine, benfotiamine, pantothenic acid; cetotiamine; cyclothiamine, dexpanthenol, niacinamide, nicotinic acid, pyridoxal 5-phosphate, nicotinamide ascorbate, riboflavin, riboflavin phosphate, thiamine, folic acid, menadiol diphosphate, menadione sodium bisulfite, menadoxime, vitamin B12, vitamin K5, vitamin K6, vitamin K6, and vitamin U; albumin, immunoglobulins, caseins, hemoglobins, lysozymes, immunoglobins, a-2-macroglobulin, fibronectins, vitronectins, firbinogens, lipases, benzalkonium chloride, benzethonium chloride, docecyl trimethyl ammonium bromide, sodium docecylsulfates, dialkyl methylbenzyl ammonium chloride, and dialkylesters of sodium sulfonsuccinic acid, L-ascorbic acid and its salt, D-glucoascorbic acid and its salt, tromethamine, triethanolamine, diethanolamine, meglumine, glucamine, amine alcohols, glucoheptonic acid, glucomic acid, hydroxyl ketone, hydroxyl lactone, gluconolactone, glucoheptonolactone, glucooctanoic lactone, gulonic acid lactone, mannoic lactone, ribonic acid lactone, lactobionic acid, glucosamine, glutamic acid, benzyl alcohol, benzoic acid, hydroxybenzoic acid, propyl 4-hydroxybenzoate, lysine acetate salt, gentisic acid, lactobionic acid, lactitol, sinapic acid, vanillic acid, vanillin, methyl paraben, propyl paraben, sorbitol, cyclodextrin, (2-hydroxypropyl)-cyclodextrin, acetaminophen, ibuprofen, retinoic acid, lysine acetate, gentisic acid, catechin, catechin gallate, tiletamine, ketamine, propofol, lactic acids, acetic acid, salts of any of the foregoing organic acids and amines, polyglycidol, glycerols, multiglycerols, and mixtures of the additives, and derivatives thereof. In another embodiment, the medical device further comprises a dimethylsulfoxide solvent layer, wherein the dimethylsulfoxide solvent layer is overlying the surface of the layer.

In another embodiment of the medical device, the layer overlying the exterior surface of the medical device comprises a therapeutic agent, at least two additives, and at least one of an oil, a fatty acid, and a lipid.

In another embodiment of the medical device, the layer overlying the exterior surface of the medical device comprises a therapeutic agent, at least two additives, and at least one of an oil, a fatty acid, and a lipid, wherein each additive is soluble in polar organic solvent and is soluble in water. In one aspect of this embodiment, the polar organic solvent is chosen from methanol, ethanol, isopropanol, acetone, dimethylformide, tetrahydrofuran, methylethyl ketone, dimethylsulfoxide, acetonitrile, ethyl acetate, and chloroform and mixtures of these polar organic solvents with water.

In another embodiment of the medical device, the layer overlying the exterior surface of the medical device comprises a therapeutic agent, an additive, and at least one of an oil, a fatty acid, and a lipid, wherein the additive comprises a hydrophilic part and a drug affinity part, wherein the drug affinity part is at least one of a hydrophobic part, a part that has an affinity to the therapeutic agent by hydrogen bonding, and a part that has an affinity to the therapeutic agent by van der Waals interactions, wherein the therapeutic agent is interdispersed in the matrix or dispersion of the additive and the at least one of an oil, a lipid, and a fatty acid, and wherein the therapeutic agent is not water-soluble and is not enclosed in micelles or liposomes or encapsulated in polymer particles.

In another embodiment of the medical device, the layer overlying the exterior surface of the medical device comprises a therapeutic agent, an additive, and at least one of an oil, a fatty acid, and a lipid, wherein the at least one of an oil, a fatty acid, and a lipid has a fatty chain that directly inserts into lipid membrane structures of tissue, wherein the additive comprises a hydrophilic part and a drug affinity part, wherein the additive has one or more functional groups which have affinity to the drug by hydrogen bonding and/or van der Waals interactions (the functional groups include hydroxyl, ester, amide, carboxylic acid, primary, second, and tertiary amine, carbonyl, anhydrides, oxides, and amino alcohols), wherein the therapeutic agent is not water-soluble and is not enclosed in micelles or liposomes or encapsulated in particles, and wherein the layer does not include polymer.

In another embodiment, the present invention relates to a balloon catheter for delivering a therapeutic agent to a blood vessel for reducing stenosis, the catheter comprising a coating layer overlying an exterior surface of a balloon. In one embodiment of the balloon catheter, the coating layer comprises a therapeutic agent, an additive, and at least one of an oil, a fatty acid, and a lipid, wherein the additive comprises a hydrophilic part and a drug affinity part, wherein the drug affinity part is at least one of a hydrophobic part, a part that has an affinity to the therapeutic agent by hydrogen bonding, a part that has an affinity to the therapeutic agent by charge, and a par that has an affinity to the therapeutic agent by van der Waals interactions, wherein the additive is at least one of a surfactant and a chemical compound, and wherein the chemical compound is water-soluble. In one embodiment, the therapeutic agent is not enclosed in micelles or liposomes or encapsulated in polymer particles.

In one embodiment of the balloon catheter, the additive in the coating layer is an ionic or non-ionic surfactant. In another embodiment, the additive is a vitamin or derivative thereof. In another embodiment, the additive is an amino acid or derivative thereof. In another embodiment, the additive is a protein or derivative thereof. In another embodiment, the additive is an albumin. In another embodiment, the additive is soluble in an aqueous solvent and is soluble in an organic solvent. In another embodiment, the additive is an organic acid or an anhydride thereof. In yet another embodiment, the additive is chosen from sorbitan oleate and sorbitan fatty esters.

In one embodiment, the additive in the coating layer comprising the therapeutic agent, the additive, and the at least one of an oil, a fatty acid, and a lipid is chosen from PEG fatty esters, PEG omega-3 fatty esters and alcohols, glycerol fatty esters, sorbitan fatty esters, PEG glyceryl fatty esters, PEG sorbitan fatty esters, sugar fatty esters, PEG sugar esters, vitamins and derivatives, amino acids, multi amino acids and derivatives, peptides, polypeptides, proteins, quaternary ammonium salts, organic acids, salts and anhydrides.

In another embodiment, the additive in the coating layer comprising the therapeutic agent, the additive, and the at least one of an oil, a fatty acid, and a lipid is chosen from p-isononylphenoxypolyglycidol, PEG laurate, Tween 20, Tween 40, Tween 60, Tween 80, PEG oleate, PEG stearate, PEG glyceryl laurate, PEG glyceryl oleate, PEG glyceryl stearate, polyglyceryl laurate, plyglyceryl oleate, polyglyceryl myristate, polyglyceryl palmitate, polyglyceryl-6 laurate, plyglyceryl-6 oleate, polyglyceryl-6 myristate, polyglyceryl-6 palmitate, polyglyceryl-10 laurate, plyglyceryl-10 oleate, polyglyceryl-10 myristate, polyglyceryl-10 palmitate PEG sorbitan monolaurate, PEG sorbitan monolaurate, PEG sorbitan monooleate, PEG sorbitan stearate, PEG oleyl ether, PEG laurayl ether, octoxynol, monoxynol, tyloxapol, sucrose monopalmitate, sucrose monolaurate, decanoyl-N-methylglucamide, n-decyl-β-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucopyranoside, n-heptyl-β-D-thioglucoside, n-hexyl-β-D-glucopyranoside, nonanoyl-N-methylglucamide, n-noyl-β-D-glucopyranoside, octanoyl-N-methylglucamide, n-octyl-β-D-glucopyranoside, octyl-β-D-thioglucopyranoside; cystine, tyrosine, tryptophan, leucine, isoleucine, phenylalanine, asparagine, aspartic acid, glutamic acid, and methionine; acetic anhydride, benzoic anhydride, ascorbic acid, 2-pyrrolidone-5-carboxylic acid, sodium pyrrolidone carboxylate, ethylenediaminetetraacetic dianhydride, maleic and anhydride, succinic anhydride, diglycolic anhydride, glutaric anhydride, acetiamine, benfotiamine, pantothenic acid; cetotiamine; cyclothiamine, dexpanthenol, niacinamide, nicotinic acid, pyridoxal 5-phosphate, nicotinamide ascorbate, riboflavin, riboflavin phosphate, thiamine, folic acid, menadiol diphosphate, menadione sodium bisulfite, menadoxime, vitamin B12, vitamin K5, vitamin K6, vitamin K6, and vitamin U; albumin, immunoglobulins, caseins, hemoglobins, lysozymes, immunoglobins, a-2-macroglobulin, fibronectins, vitronectins, firbinogens, lipases, benzalkonium chloride, benzethonium chloride, docecyl trimethyl ammonium bromide, sodium docecylsulfates, dialkyl methylbenzyl ammonium chloride, and dialkylesters of sodium sulfonsuccinic acid, L-ascorbic acid and its salt, D-glucoascorbic acid and its salt, tromethamine, triethanolamine, diethanolamine, meglumine, glucamine, amine alcohols, glucoheptonic acid, glucomic acid, hydroxyl ketone, hydroxyl lactone, gluconolactone, glucoheptonolactone, glucooctanoic lactone, gulonic acid lactone, mannoic lactone, ribonic acid lactone, lactobionic acid, glucosamine, glutamic acid, benzyl alcohol, benzoic acid, hydroxybenzoic acid, propyl 4-hydroxybenzoate, lysine acetate salt, gentisic acid, lactobionic acid, lactitol, sinapic acid, vanillic acid, vanillin, methyl paraben, propyl paraben, diethylene glycol, triethylene glycol, tetraethylene glycol, xylitol, 2-ethoxyethanol, sugars, galactose, glucose, mannose, xylose, sucrose, lactose, maltose, sorbitol, cyclodextrin, (2-hydroxypropyl)-cyclodextrin, acetaminophen, ibuprofen, retinoic acid, lysine acetate, gentisic acid, catechin, catechin gallate, tiletamine, ketamine, propofol, lactic acids, acetic acid, salts of any of the foregoing organic acids and amines, polyglycidol, glycerols, multiglycerols, and mixtures of the additives, and derivatives thereof.

In another embodiment, the additive in the coating layer comprising the therapeutic agent, the additive, and the at least one of an oil, a fatty acid and a lipid is chosen from Tyloxapol, Octoxynol, oleth, laureth, PEG-glyceryl, monolaurate, PEG-20 monolaurate, PEG 20 monooleate, PEG 20 glyceryl monooleate, Nonoxynol, Nonylphenylpoly(glycidol), Octyl-betha-D-glycopyranoside, and deconoyl-N-methylglucamide.

In another embodiment, the additive in the coating layer comprising the therapeutic agent, the additive, and the at least one of an oil, a fatty acid, and a lipid is chosen from benzalkonium chloride, benzethonium chloride, docecyl trimethyl ammonium bromide, sodium docecylsulfates, dialkyl methylbenzyl ammonium chloride, and dialkylesters of sodium sulfonsuccinic acid.

In one embodiment, the therapeutic agent is one of paclitaxel and analogues thereof, rapamycin and analogues thereof, beta-lapachone and analogues thereof, biological vitamin D and analogues thereof, and a mixture of these therapeutic agents. In another embodiment, the therapeutic agent is in combination with a second therapeutic agent, wherein the therapeutic agent is one of paclitaxel, rapamycin, and analogues thereof, and wherein the second therapeutic agent is one of beta-lapachone, biological active vitamin D, and their analogues. In one embodiment, the therapeutic agent is not water-soluble.

In one embodiment, the additive enhances penetration and absorption of the therapeutic agent in the blood vessel. In another embodiment, the additive penetrates the blood vessel, and the therapeutic agent is not water-soluble. In another embodiment, the additive has water and ethanol solubility of at least 1 mg/ml, and the therapeutic agent is not water-soluble.

In one embodiment of the balloon catheter, the catheter further comprises an adherent layer between the exterior surface of the balloon and the coating layer. In another embodiment, the catheter further comprises a top layer overlying the coating layer, wherein the top layer reduces loss of the therapeutic agent during transit through a body to the blood vessel. In one embodiment, the top layer comprises an additive chosen from those additives, according to embodiments of the invention described herein. The top layer will be slowly dissolved during transit through a body to the body lumen to the target site for therapeutic intervention. This top layer will reduce drug loss during transit and increase the drug available to the tissue when the medical device of embodiments of the present invention is pressed into contact with luminal tissue.

In one embodiment, the additive in the top layer is less hydrophilic than the additive in the coating layer. In another embodiment, the catheter further comprises a dimethylsulfoxide solvent layer, wherein the dimethylsulfoxide solvent layer is overlying the surface of the coating layer.

In one embodiment, the balloon catheter is capable of delivering the therapeutic agent to the blood vessel in about 0.2 to 2 minutes. In another embodiment, the balloon catheter is capable of delivering the therapeutic agent to the blood vessel in about 0.1 to 1 minute.

In one embodiment of the balloon catheter, the concentration of the therapeutic agent in the coating layer is from 1 to 20 $\mu g/mm^2$. In another embodiment, the concentration of the therapeutic agent in the coating layer is from 2 to 6 $\mu g/mm^2$. In one embodiment, the concentration of the additive in the coating layer is from 1 to 10 $\mu g/mm^2$.

In yet a further embodiment, the present invention relates to a balloon catheter for delivering a therapeutic agent to a blood vessel. In one aspect of this embodiment, the catheter comprises an elongate member having a lumen and a distal end, an expandable balloon attached to the distal end of the elongate member and in fluid communication with the lumen, and a coating layer overlying an exterior surface of the balloon. In one aspect of this embodiment, the coating layer overlying the surface of the balloon comprises a lipophilic or water-insoluble therapeutic agent, an additive, and at least one of an oil, a fatty acid, and a lipid wherein the additive comprises a hydrophilic part and a drug affinity part, wherein the drug affinity part is at least one of a hydrophobic part, a part that has an affinity to the therapeutic agent by hydrogen bonding, a part that has an affinity to the therapeutic agent by charge, and a part that has an affinity to the therapeutic agent by van der Waals interactions, wherein the additive is water-soluble, and wherein the catheter is capable of delivering the therapeutic agent to the blood vessel in less than about 2 minutes.

In one embodiment, the coating layer overlying the surface of the balloon consists essentially of the therapeutic agent, the additive, and the at least one of an oil, a fatty acid, and a lipid. In one embodiment, the therapeutic agent in the coating layer overlying the surface of the balloon is paclitaxel and analogues thereof. In another embodiment, the therapeutic agent in the coating layer overlying the surface of the balloon is rapamycin and analogues thereof.

In one embodiment, the concentration of the therapeutic agent in the coating layer is from 2.5 to 6 $\mu g/mm^2$.

In one embodiment, the additive in the coating layer overlying the surface of the balloon is an ionic or non-ionic surfactant. In another embodiment, the additive in the coating layer overlying the surface of the balloon is a vitamin or derivative thereof.

In one embodiment, the additive in the coating layer overlying the surface of the balloon is chosen from Tyloxapol, Octoxynol, oleth, laureth, PEG-glyceryl, monolaurate, PEG-20 monolaurate, PEG 20 monooleate, PEG 20 glyceryl monooleate, Nonoxynol, Nonylphenylpoly(glycidol), Octyl-betha-D-glycopyranoside, and deconoyl-N-methylglucamide.

In another embodiment, the additive in the coating layer overlying the surface of the balloon is chosen from PEG fatty esters, PEG omega-3 fatty esters and alcohols, glycerol fatty esters, sorbitan fatty esters, PEG glyceryl fatty esters, PEG sorbitan fatty esters, sugar fatty esters, PEG sugar esters, vitamins and derivatives, amino acids, multi amino acids and derivatives, peptides, polypeptides, proteins, quaternary ammonium salts, organic acids, salts and anhydrides.

In another embodiment, the additive in the coating layer overlying the surface of the balloon is chosen from p-isononylphenoxypolyglycidol, PEG laurate, PEG oleate, PEG stearate, PEG glyceryl laurate, PEG glyceryl oleate, PEG glyceryl stearate, polyglyceryl laurate, plyglyceryl oleate, polyglyceryl myristate, polyglyceryl palmitate, polyglyceryl-6 laurate, plyglyceryl-6 oleate, polyglyceryl-6 myristate, polyglyceryl-6 palmitate, polyglyceryl-10 laurate, plyglyceryl-10 oleate, polyglyceryl-10 myristate, polyglyceryl-10 palmitate PEG sorbitan monolaurate, PEG sorbitan monolaurate, PEG sorbitan monooleate, PEG sorbitan stearate, PEG oleyl ether, PEG laurayl ether, octoxynol, monoxynol, tyloxapol, sucrose monopalmitate, sucrose monolaurate, Tween 20, Tween 40, Tween 60, decanoyl-N-methylglucamide, n-decyl-β-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucopyranoside, n-heptyl-β-D-thioglucoside, n-hexyl-β-D-glucopyranoside, nonanoyl-N-methylglucamide, n-noyl-β-D-glucopyranoside, octanoyl-N-methylglucamide, n-octyl-β-D-glucopyranoside, octyl-β-D-thioglucopyranoside; cystine, tyrosine, tryptophan, leucine, isoleucine, phenylalanine, asparagine, aspartic acid, glutamic acid, and methionine (amino acids); acetic anhydride, benzoic anhydride, ascorbic acid, 2-pyrrolidone-5-carboxylic acid, sodium pyrrolidone carboxylate, ethylenediaminetetraacetic dianhydride, maleic and anhydride, succinic anhydride, diglycolic anhydride, glutaric anhydride, acetiamine, benfotiamine, pantothenic acid (organic acids and anhydrides); cetotiamine; cyclothiamine, dexpanthenol, niacinamide, nicotinic acid, pyridoxal 5-phosphate, nicotinamide ascorbate, riboflavin, riboflavin phosphate, thiamine, folic acid, menadiol diphosphate, menadione sodium bisulfite, menadoxime, vitamin B12, vitamin K5, vitamin K6, vitamin K6, and vitamin U (vitamins); albumin, immunoglobulins, caseins, hemoglobins, lysozymes, immunoglobins, a-2-macroglobulin, fibronectins, vitronectins, firbinogens, lipases, benzalkonium chloride, benzethonium chloride, docecyl trimethyl ammonium bromide, sodium docecylsulfates, dialkyl methylbenzyl ammonium chloride, and dialkylesters of sodium sulfonsuccinic acid (ionic surfactants), L-ascorbic acid and its salt, D-glucoascorbic acid and its salt, triethanolamine, diethanolamine, meglumine, tromethamine, glucamine, glucosamine, glucoheptonic acid, glucomic acid, hydroxyl ketone, hydroxyl lactone, gluconolactone, glucoheptonolactone, glucooctanoic lactone, gulonic acid lactone, mannoic lactone, ribonic acid lactone, lactobionic acid, glucosamine, glutamic acid, benzyl alcohol, benzoic acid, hydroxybenzoic acid, vanillin, vanillic acid, vanillic acid diethylamide, lysine acetate salt, gentisic acid, lactobionic acid, lactitol, sorbitol, cyclodextrin, (2-hydroxypropyl)-cyclodextrin, acetaminophen, ibuprofen, catechin, catechin gallate, methyl paraben, ethyl paraben, propyl paraben, butyl paraben, tiletamine, ketamine, propofol, lactic acids, acetic acid, diethylene glycol, triethylene glycol, tetraethylene glycol, xylitol, 2-ethoxyethanol, sugars, galactose, glucose, mannose, xylose, sucrose, lactose, maltose, salts of any organic acid and amine described above, polyglycidol, glycerols and multiglycerols (chemical compounds with one or more hydroxyl, amino, carbonyl, carboxyl, or ester moieties). In yet another embodiment, the additive in the coating layer overlying the surface of the balloon is chosen from benzalkonium chloride, benzethonium chloride, docecyl trimethyl ammonium bromide, sodium docecylsulfates, dialkyl methylbenzyl ammonium chloride, and dialkylesters of sodium sulfonsuccinic acid.

In one embodiment, the balloon catheter further comprises a dimethylsulfoxide solvent layer overlying the coating layer, wherein the dimethylsulfoxide layer enhances the ability of the therapeutic agent to penetrate into the blood vessel. In another embodiment, the balloon catheter further comprises an adherent layer between the exterior surface of the balloon and the coating layer. In yet another embodiment, the balloon catheter further comprises a top layer overlying the coating layer, wherein the top layer reduces loss of the therapeutic agent and/or additive in the coating layer during transit through a body or blood vessel to the target site for intervention.

In yet a further embodiment, the present invention relates to a pharmaceutical composition for treating a diseased body lumen or cavity after a surgical or interventional procedure, wherein the composition comprises a therapeutic agent, an additive, and at least one of an oil, a fatty acid, and a lipid, wherein the additive comprises a hydrophilic part and a drug affinity part, wherein the drug affinity part is at least one of a hydrophobic part, a part that has an affinity to the therapeutic agent by hydrogen bonding, and a part that has an affinity to the therapeutic agent by van der Waals interactions, and wherein the therapeutic agent is not enclosed in micelles or liposomes or encapsulated in polymer particles.

In yet a further embodiment, the present invention relates to a method for treating a diseased body lumen or cavity after a surgical or interventional procedure comprising delivering a pharmaceutical composition at a surgical site by injection or spraying with a catheter, wherein the composition comprises a therapeutic agent, an additive, and at least one of an oil, a fatty acid and a lipid, wherein the additive comprises a hydrophilic part and a drug affinity part, wherein the drug affinity part is at least one of a hydrophobic part, a part that has an affinity to the therapeutic agent by hydrogen bonding, and a part that has an affinity to the therapeutic agent by van der Waals interactions, and wherein the therapeutic agent is not enclosed in micelles or liposomes or encapsulated in polymer particles.

In yet a further embodiment, the present invention relates to a pharmaceutical composition for treating a cancer including cancers of the ovary, breast, lung, esophagus, head and neck region, bladder, brain, liver, colon and lymphomas, wherein the composition comprises a therapeutic agent, an additive, and at least one of an oil, a fatty acid and a lipid, wherein the additive comprises a hydrophilic part and a drug affinity part, wherein the drug affinity part is at least one of a hydrophobic part, a part that has an affinity to the therapeutic agent by hydrogen bonding, and a part that has an affinity to the therapeutic agent by van der Waals interactions, and wherein the therapeutic agent is not enclosed in micelles or liposomes or encapsulated in polymer particles. In one aspect of this embodiment, the therapeutic agent is chosen from paclitaxel and analogues thereof and rapamycin and analogues thereof.

In yet a further embodiment, the present invention relates to a solution for coating a medical device. In one aspect of this embodiment, the solution comprises an organic solvent, a therapeutic agent, an additive, and at least one of an oil, a fatty acid, and a lipid, wherein the additive comprises a hydrophilic part and a drug affinity part, wherein the drug affinity part is at least one of a hydrophobic part, a part that has an affinity to the therapeutic agent by hydrogen bonding, and a part that has an affinity to the therapeutic agent by van der Waals interactions, and wherein the therapeutic agent is not enclosed in micelles or liposomes or encapsulated in polymer particles. In another embodiment, the solution for coating a medical device does not include a polymer.

In one embodiment, the additive in the coating solution is an ionic or non-ionic surfactant. In another embodiment, the additive in the coating solution is a vitamin or derivative thereof.

In one embodiment, the additive in the coating solution is chosen from Tyloxapol, Octoxynol, oleth, laureth, PEG-glyceryl, monolaurate, PEG-20 monolaurate, PEG 20 monooleate, PEG 20 glyceryl monooleate, Nonoxynol, Nonylphenylpoly(glycidol), Octyl-betha-D-glycopyranoside, and deconoyl-N-methylglucamide.

In another embodiment, the additive in the coating solution is chosen from PEG fatty esters, PEG omega-3 fatty esters and alcohols, glycerol fatty esters, sorbitan fatty esters, PEG glyceryl fatty esters, PEG sorbitan fatty esters, sugar fatty esters, PEG sugar esters, vitamins and derivatives, amino acids, multi amino acids and derivatives, peptides, polypeptides, proteins, quaternary ammonium salts, organic acids, salts and anhydrides.

In another embodiment, the additive in the coating solution is chosen from p-isononylphenoxypolyglycidol, PEG laurate, PEG oleate, PEG stearate, PEG glyceryl laurate, PEG glyceryl oleate, PEG glyceryl stearate, polyglyceryl laurate, plyglyceryl oleate, polyglyceryl myristate, polyglyceryl palmitate, polyglyceryl-6 laurate, plyglyceryl-6 oleate, polyglyceryl-6 myristate, polyglyceryl-6 palmitate, polyglyceryl-10 laurate, plyglyceryl-10 oleate, polyglyceryl-10 myristate, polyglyceryl-10 palmitate PEG sorbitan monolaurate, PEG sorbitan monolaurate, PEG sorbitan monooleate, PEG sorbitan stearate, PEG oleyl ether, PEG laurayl ether, octoxynol, monoxynol, tyloxapol, Tween 20, Tween 80, Tween 40, Tween 60, sucrose monopalmitate, sucrose monolaurate, decanoyl-N-methylglucamide, n-decyl-β-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucopyranoside, n-heptyl-β-D-thioglucoside, n-hexyl-β-D-glucopyranoside, nonanoyl-N-methylglucamide, n-noyl-β-D-glucopyranoside, octanoyl-N-methylglucamide, n-octyl-β-D-glucopyranoside, octyl-β-D-thioglucopyranoside; cystine, tyrosine, tryptophan, leucine, isoleucine, phenylalanine, asparagine, aspartic acid, glutamic acid, and methionine (amino acids); acetic anhydride, benzoic anhydride, ascorbic acid, 2-pyrrolidone-5-carboxylic acid, sodium pyrrolidone carboxylate, ethylenediaminetetraacetic dianhydride, maleic and anhydride, succinic anhydride, diglycolic anhydride, glutaric anhydride, acetiamine, benfotiamine, pantothenic acid (organic acids and anhydrides); cetotiamine; cyclothiamine, dexpanthenol, niacinamide, nicotinic acid, pyridoxal 5-phosphate, nicotinamide ascorbate, riboflavin, riboflavin phosphate, thiamine, folic acid, menadiol diphosphate, menadione sodium bisulfite, menadoxime, vitamin B12, vitamin K5, vitamin K6, vitamin K6, and vitamin U (vitamins); albumin, immunoglobulins, caseins, hemoglobins, lysozymes, immunoglobins, a-2-macroglobulin, fibronectins, vitronectins, firbinogens, lipases (proteins), benzalkonium chloride, benzethonium chloride, docecyl trimethyl ammonium bromide, sodium docecylsulfates, dialkyl methylbenzyl ammonium chloride, and dialkylesters of sodium sulfonsuccinic acid (ionic surfactants), L-ascorbic acid and its salt, D-glucoascorbic acid and its salt, triethanolamine, diethanolamine, meglumine, tromethamine, glucamine, glucosamine, glucoheptonic acid, glucomic acid, hydroxyl ketone, hydroxyl lactone, gluconolactone, glucoheptonolactone, glucooctanoic lactone, gulonic acid lactone, mannoic lactone, ribonic acid lactone, lactobionic acid, glutamic acid, benzyl alcohol, benzoic acid, hydroxybenzoic acid, vanillin, vanillic acid, vanillic acid diethylamide, lysine acetate salt, gentisic acid, lactobionic acid, lactitol, diethylene glycol, triethylene glycol, tetraethylene glycol, xylitol, 2-ethoxyethanol, sugars, galactose, glucose, mannose, xylose, sucrose, lactose, maltose, sorbitol, cyclodextrin, (2-hydroxypropyl)-cyclodextrin, acetaminophen, ibuprofen, catechin, catechin gallate, methyl paraben, ethyl paraben, propyl paraben, butyl paraben, tiletamine, ketamine, propofol, lactic acids, acetic acid, salts of any organic acid and amine described above (chemical compounds with one or more hydroxyl, amino, carbonyl, carboxyl, or ester moieties).

In another embodiment, the additive in the solution is chosen from sorbitan fatty esters. In yet another embodiment, the additive in the coating solution is chosen from benzalkonium chloride, benzethonium chloride, docecyl trimethyl ammonium bromide, sodium docecylsulfates, dialkyl methylbenzyl ammonium chloride, and dialkylesters of sodium sulfonsuccinic acid.

In one embodiment, the therapeutic agent in the coating solution is paclitaxel or rapamycin.

In one embodiment, the content of the therapeutic agent in the solution is from 0.5-50% by weight. In one embodiment, the content of the additive in the coating solution is from 1-45% by weight.

In one embodiment, the additive in the solution is soluble in aqueous solvent and is soluble in organic solvent.

In yet a further embodiment, the present invention relates to a medical device for delivering a therapeutic agent to a tissue, the device comprising a first layer applied to an exterior surface of the medical device, and a second layer overlying the first layer. In one aspect of this embodiment, the first layer comprises a therapeutic agent, and the second layer comprises a mixture of the additive and at least one of an oil, a fatty acid, and a lipid, and wherein the therapeutic agent in the first layer is not enclosed in micelles or liposomes or encapsulated in polymer particles. In one aspect of this embodiment, the first layer further comprises an additive and at least one of an oil, a fatty acid, and a lipid. In another aspect of this embodiment, the second layer further comprises a therapeutic agent. In yet a further aspect of this embodiment, the first layer further comprises an additive, at least one of an oil, a fatty acid, and a lipid, and the second layer further comprises a therapeutic agent.

In a further embodiment, the present invention relates to a two layer coating comprising a first layer comprising a therapeutic agent, and a second layer comprising an additive and at least one of an oil, a fatty acid, and a lipid. In one aspect of this embodiment, the second layer may be overlying the first layer. In one aspect of this embodiment, the additive in the second layer is hydrophilic, and the therapeutic agent in the first layer is not enclosed in micelles or liposomes or encapsulated in polymer particles. In one aspect of this embodiment, the first layer further comprises an additive and at least one of an oil, a fatty acid, and a lipid. In another aspect of this embodiment, the second layer further comprises a therapeutic agent. In yet another aspect of this embodiment, the first layer further comprises an additive and at least one of an oil, a fatty acid, and a lipid and the second layer further comprises a therapeutic agent.

In a further embodiment, the present invention relates to a method for preparing a medical device. In one aspect of this embodiment, the method comprises (a) preparing a coating solution comprising an organic solvent, a therapeutic agent, an additive, and at least one of an oil, a fatty acid, and a lipid, wherein the additive comprises a hydrophilic part and a drug affinity part, wherein the drug affinity part is at least one of a hydrophobic part, a part that has an affinity to the therapeutic agent by hydrogen bonding, and a part that has an affinity to the therapeutic agent by van der Waals interactions, and wherein the therapeutic agent is not enclosed in micelles or liposomes or encapsulated in polymer particles, (b) applying the coating solution to a medical device, and (c) drying the coating solution, forming a coating layer. In one aspect of this embodiment, the coating is applied by dipping a portion of the exterior surface of the medical device in the coating solution. In another aspect of this embodiment, the coating is applied by spraying a portion of the exterior surface of the medical device with a coating solution. In another aspect of this embodiment, steps (b) and (c) are repeated until a therapeutically effective amount of the therapeutic agent in the coating layer is deposited on the surface of the medical device. In another aspect of this embodiment, the total thickness of the coating layer is from about 0.1 to 200 microns. In another aspect of this embodiment, the concentration density of the at least one therapeutic agent applied to the surface of the medical device is from about 1 to 20 $\mu g/mm^2$, or in another aspect from about 2 to 6 $\mu g/mm^2$. In yet another aspect of this embodiment, the method further comprises applying a dimethylsulfoxide solvent to the dried coating layer obtained in step (c).

In a further embodiment, the present invention relates to a method for preparing a drug coated balloon catheter. In one aspect of this embodiment, the method comprises, (a) preparing a coating solution comprising an organic solvent, a therapeutic agent, an additive, and at least one of an oil, a fatty acid, and a lipid, wherein the additive comprises a hydrophilic part and a drug affinity part, wherein the drug affinity part is at least one of a hydrophobic part, a part that has an affinity to the therapeutic agent by hydrogen bonding, and a part that has an affinity to the therapeutic agent by van der Waals interactions, (b) applying the coating solution to an inflated balloon catheter, and (c) deflating and folding the balloon catheter and drying the coating solution to increase uniformity of drug coating.

In a further embodiment, the present invention relates to a method for treating a blood vessel. In one aspect of this embodiment, the method comprises inserting a medical device comprising a coating layer into the blood vessel, wherein the coating layer comprises a therapeutic agent, an additive, and at least one of an oil, a fatty acid, and a lipid, wherein the additive comprises a hydrophilic part and a drug affinity part, wherein the drug affinity part is at least one of a hydrophobic part, a part that has an affinity to the therapeutic agent by hydrogen bonding, and a part that has an affinity to the therapeutic agent by van der Waals interactions, and wherein the therapeutic agent is not enclosed in micelles or liposomes or encapsulated in polymer particles, and releasing the therapeutic agent into the tissue of the blood vessel in 2 minutes or less.

In a further embodiment, the present invention relates to a method for treating a total occlusion or narrowing of body passages. In one aspect of this embodiment, the method comprises removing plaques in the body passages, for example, by one of a debulking catheter, a laser atherectomy, a directing atherectomy, or a rotational atherectomy, inserting a medical device comprising a coating layer into the body passages, wherein the coating layer comprises a therapeutic agent, an additive, and at least one of an oil, a fatty acid, and a lipid, wherein the additive comprises a hydrophilic part and a drug affinity part, wherein the drug affinity part is at least one of a hydrophobic part, a part that has an affinity to the therapeutic agent by hydrogen bonding, and a part that has an affinity to the therapeutic agent by van der Waals interactions, and releasing the therapeutic agent into the tissue of the body passage or lumen, such as a blood vessel, in 2 minutes or less.

In a further embodiment, the present invention relates to a method for treating tissue of a body comprising bringing a medical device comprising a coating layer into contact with tissue of the body, wherein the coating layer comprises a therapeutic agent, an additive, and at least one of an oil, a fatty acid, and a lipid, wherein the additive comprises a hydrophilic part and a drug affinity part, wherein the drug affinity part is at least one of a hydrophobic part, a part that has an affinity to the therapeutic agent by hydrogen bonding, and a part that has an affinity to the therapeutic agent by van der Waals interactions, and releasing the therapeutic agent into the tissue in 2 minutes or less. In one aspect of this embodiment, the tissue includes tissue of one of coronary vasculature, peripheral vasculature, cerebral vasculature, esophagus, airways, sinus, trachea, colon, biliary tract, urinary tract, prostate, and brain passages.

In yet a further embodiment, the present invention relates to a process of producing a balloon catheter. In one aspect of this embodiment, the process comprises preparing a solution comprising an organic solvent, a therapeutic agent, an additive, and at least one of an oil, a fatty acid, and a lipid, wherein the additive comprises a hydrophilic part and a drug affinity part, wherein the drug affinity part is at least one of a hydrophobic part, a part that has an affinity to the therapeutic agent by hydrogen bonding, and a part that has an affinity to the therapeutic agent by van der Waals interactions, and wherein the therapeutic agent is not enclosed in micelles or liposomes or encapsulated in polymer particles, applying the solution to the balloon catheter, and evaporating the solvent.

In yet a further embodiment, the present invention relates to a medical device comprising a layer overlying an exterior surface of the medical device, the layer comprising a therapeutic agent, an additive, and at least one of an oil, a fatty acid and a lipid, wherein the additive is one of PEG fatty ester, PEG fatty ether, and PEG fatty alcohols. In one aspect of this embodiment, the additive is chosen from PEG-8 laurate, PEG-8 oleate, PEG-8 stearate, PEG-9 oleate, PEG-10 laurate, PEG-10 oleate, PEG-12 laurate, PEG-12 oleate, PEG-15 oleate, PEG-20 laurate, PEG-20 oleate, PEG-20 dilaurate, PEG-20 dioleate, PEG-20 distearate, PEG-32 dilaurate and PEG-32 dioleate. In another aspect of this embodiment, the tissue includes tissue of one of coronary vasculature, peripheral vasculature, cerebral vasculature, esophagus, airways, sinus, trachea, colon, biliary tract, urinary tract, prostate, and brain passages. In yet another aspect of this embodiment, the device includes one of a balloon catheter, a perfusion balloon catheter, a cutting balloon catheter, a scoring balloon catheter, a laser catheter, an atherectomy device, a debulking catheter, a stent, a filter, a stent graft, a covered stent, a patch, a wire, and a valve.

In yet a further embodiment, the present invention relates to a medical device comprising a layer overlying an exterior surface of the medical device, the layer comprising a therapeutic agent, an additive, and at least one of an oil, a fatty acid, and a lipid, wherein the additive is one of glycerol and polyglycerol fatty esters and PEG glycerol fatty esters. In one aspect of this embodiment, the additive is chosen from polyglyceryl oleate, polyglyceryl-2 dioleate, polyglyceryl-10 trioleate, polyglyceryl stearate, polyglyceryl laurate, polyglyceryl myristate, polyglyceryl palmitate, polyglyceryl linoleate, polyglyceryl-10 laurate, polyglyceryl-10 oleate, polyglyceryl-10 mono, dioleate, polyglyceryl-10 stearate, polyglyceryl-10 laurate, polyglyceryl-10 myristate, polyglyceryl-10 palmitate, polyglyceryl-10 linoleate, polyglyceryl-6 stearate, polyglyceryl-6 laurate, polyglyceryl-6 myristate, polyglyceryl-6 palmitate, and polyglyceryl-6 linoleate, polyglyceryl polyricinoleates, PEG-20 glyceryl laurate, PEG-30 glyceryl laurate, PEG-40 glyceryl laurate, PEG-20 glyceryl oleate, and PEG-30 glyceryl oleate. In another aspect of this embodiment, the tissue includes tissue of one of coronary vasculature, peripheral vasculature, cerebral vasculature, esophagus, airways, sinus, trachea, colon, biliary tract, urinary tract, prostate, and brain passages. In yet another aspect of this embodiment, the device includes one of a balloon catheter, a perfusion balloon catheter, a cutting balloon catheter, a scoring balloon catheter, a laser catheter, an atherectomy device, a debulking catheter, a stent, a filter, a stent graft, a covered stent, a patch, a wire, and a valve.

In yet a further embodiment, the present invention relates to a medical device comprising a layer overlying an exterior surface of the medical device, the layer comprising a therapeutic agent, an additive, and at least one of an oil, a fatty acid, and a lipid, wherein the additive is one of sorbitan fatty esters, and PEG sorbitan esters. In one aspect of this embodiment, the additive is chosen from sorbitan monolaurate, sorbitan monopalmitate, sorbitan monooleate, sorbitan monostearate, Tween 20, Tween 40, Tween 60, Tween 80, PEG-20 sorbitan monolaurate, PEG-20 sorbitan monopalmitate, PEG-20 sorbitan monooleate, and PEG-20 sorbitan monostearate. In another aspect of this embodiment, the tissue includes tissue of one of coronary vasculature, peripheral vasculature, cerebral vasculature, esophagus, airways, sinus, trachea, colon, biliary tract, urinary tract, prostate, and brain passages. In yet another aspect of this embodiment, the device includes one of a balloon catheter, a perfusion balloon catheter, an infusion catheter, perforated balloon, porous balloon, weeping balloon, a cutting balloon catheter, a scoring balloon catheter, a laser catheter, an atherectomy device, a debulking catheter, a stent, a filter, a stent graft, a covered stent, a patch, a wire, and a valve.

In yet a further embodiment, the present invention relates to a medical device comprising a layer overlying an exterior surface of the medical device, the layer comprising a therapeutic agent, an additive, and at least one of an oil, a fatty acid, and a lipid, wherein the additive is a chemical compound containing a phenol moiety. In one aspect of this embodiment, the additive is chosen from p-isononylphenoxypolyglycidol, octoxynol, monoxynol, tyloxapol, octoxynol-9, and monoxynol-9. In another aspect of this embodiment, the tissue includes tissue of one of coronary vasculature, peripheral vasculature, cerebral vasculature, esophagus, airways, sinus, trachea, colon, biliary tract, urinary tract, prostate, and brain passages. In yet another aspect of this embodiment, the device includes one of a balloon catheter, a perfusion balloon catheter, an infusion catheter, perforated balloon, porous balloon, weeping balloon, a cutting balloon catheter, a scoring balloon catheter, a laser catheter, an atherectomy device, a debulking catheter, a stent, a filter, a stent graft, a covered stent, a patch, a wire, and a valve.

In yet a further embodiment, the present invention relates to a medical device comprising a layer overlying an exterior surface of the medical device, the layer comprising a therapeutic agent, an additive, and at least one of an oil, a fatty acid, and a lipid, wherein the additive is a sugar or sugar derivative. In one aspect of this embodiment, the additive is chosen from sucrose monolaurate, decanoyl-N-methylglucamide, n-decyl-β-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucopyranoside, n-heptyl-β-D-thioglucoside, n-hexyl-β-D-glucopyranoside, nonanoyl-N-methylglucamide, n-noyl-β-D-glucopyranoside, octanoyl-N-methylglucamide, n-octyl-β-D-glucopyranoside, octyl-β-D-thioglucopyranoside, D-glucoascorbic acid and its salt, triethanolamine, diethanolamine, meglumine, tromethamine, glucamine, glucosamine, glucoheptonic acid, glucomic acid, hydroxyl ketone, hydroxyl lactone, gluconolactone, glucoheptonolactone, glucooctanoic lactone, gulonic acid lactone, mannoic lactone, ribonic acid lactone, lactobionic acid, glutamic acid, benzyl alcohol, benzoic acid, hydroxybenzoic acid, vanillin, vanillic acid, vanillic acid diethylamide, lysine acetate salt, gentisic acid, lactobionic acid, lactitol, diethylene glycol, triethylene glycol, tetraethylene glycol, xylitol, 2-ethoxyethanol, sugars, galactose, glucose, mannose, xylose, sucrose, lactose, maltose, sorbitol, cyclodextrin, (2-hydroxypropyl)-cyclodextrin, acetaminophen, ibuprofen, catechin, catechin gallate, methyl paraben, ethyl paraben, propyl paraben, butyl paraben, tiletamine, ketamine, propofol, lactic acids, acetic acid, salts of any organic acid and amine described above. In another aspect of this embodiment, the tissue includes tissue of one of coronary vasculature, peripheral vasculature, cerebral vasculature, esophagus, airways, sinus, trachea, colon, biliary tract, urinary tract, prostate, and brain passages. In yet another aspect of this embodiment, the device includes one of a balloon catheter, a perfusion balloon catheter, a cutting balloon catheter, a scoring balloon catheter, a laser catheter, an atherectomy device, a debulking catheter, a stent, a filter, a stent graft, a covered stent, a patch, a wire, and a valve.

In yet a further embodiment, the present invention relates to a medical device comprising a layer overlying an exterior surface of the medical device, the layer comprising a therapeutic agent, an additive, and at least one of an oil, a fatty acid, and a lipid, wherein the additive is an ionic surfactant. In one aspect of this embodiment, the additive is chosen from benzalkonium chloride, benzethonium chloride, cetylpyridinium chloride, docecyl trimethyl ammonium bromide, sodium docecylsulfates, dialkyl methylbenzyl ammonium chloride, edrophonium chloride, domiphen bromide, and dialkylesters of sodium sulfonsuccinic acid, sodium dioctyl sulfosuccinate, sodium cholate, and sodium taurocholate. In another aspect of this embodiment, the tissue includes tissue of one of coronary vasculature, peripheral vasculature, cerebral vasculature, esophagus, airways, sinus, trachea, colon, biliary tract, urinary tract, prostate, and brain passages. In yet another aspect of this embodiment, the device includes one of a balloon catheter, a perfusion balloon catheter, an infusion catheter, perforated balloon, porous balloon, weeping balloon, a cutting balloon catheter, a scoring balloon catheter, a laser catheter, an atherectomy device, a debulking catheter, a stent, a filter, a stent graft, a covered stent, a patch, a wire, and a valve.

In yet a further embodiment, the present invention relates to a medical device comprising a layer overlying an exterior surface of the medical device, the layer comprising a therapeutic agent, an additive, at least one of an oil, a fatty acid, and a lipid, wherein the additive is a vitamin or vitamin derivative. In one aspect of this embodiment, the additive is chosen from acetiamine, benfotiamine, pantothenic acid, cetotiamine, cyclothiamine, dexpanthenol, niacinamide, nicotinic acid and its salts, pyridoxal 5-phosphate, nicotinamide ascorbate, riboflavin, riboflavin phosphate, thiamine, folic acid, menadiol diphosphate, menadione sodium bisulfite, menadoxime, vitamin B12, vitamin K5, vitamin K6, vitamin K6, vitamin U, ergosterol, 1-alpha-hydroxycholecal-ciferol, vitamin D2, vitamin D3, alpha-carotene, beta-carotene, gamma-carotene, vitamin A, fursultiamine, methylolriboflavin, octotiamine, prosultiamine, riboflavine, vintiamol, dihydrovitamin K1, menadiol diacetate, menadiol dibutyrate, menadiol disulfate, menadiol, vitamin K1, vitamin K1 oxide, vitamins K2, and vitamin K—S(II). In another aspect of this embodiment, the tissue includes tissue of one of coronary vasculature, peripheral vasculature, cerebral vasculature, esophagus, airways, sinus, trachea, colon, biliary tract, urinary tract, prostate, and brain passages. In yet another aspect of this embodiment, the device includes one of a balloon catheter, a perfusion balloon catheter, an infusion catheter, perforated balloon, porous balloon, weeping balloon, a cutting balloon catheter, a scoring balloon catheter, a laser catheter, an atherectomy device, a debulking catheter, a stent, a filter, a stent graft, a covered stent, a patch, a wire, and a valve.

In yet a further embodiment, the present invention relates to a medical device comprising a layer overlying an exterior surface of the medical device, the layer comprising a therapeutic agent, an additive, and at least one of an oil, a fatty acid, and a lipid, wherein the additive is an amino acid, an amino acid salt, or an amino acid derivative. In one aspect of this embodiment, the additive is chosen from alanine, arginine, asparagine, aspartic acid, cysteine, glutamic acid, glutamine, glycine, histidine, proline, isoleucine, leucine, lysine, methionine, phenylalanine, serine, threonine, tryptophan, tyrosine, valine, and derivatives thereof. In another aspect of this embodiment, the tissue includes tissue of one of coronary vasculature, peripheral vasculature, cerebral vasculature, esophagus, airways, sinus, trachea, colon, biliary tract, urinary tract, prostate, and brain passages. In yet another aspect of this embodiment, the device includes one of a balloon catheter, a perfusion balloon catheter, an infusion catheter, perforated balloon, porous balloon, weeping balloon, a cutting balloon catheter, a scoring balloon catheter, a laser catheter, an atherectomy device, a debulking catheter, a stent, a filter, a stent graft, a covered stent, a patch, a wire, and a valve.

In yet a further embodiment, the present invention relates to a medical device for delivering a therapeutic agent to a tissue, the device comprising a layer overlying an exterior surface of the medical device, the layer comprising a therapeutic agent, an additive, at least one of an oil, a fatty acid, and a lipid, wherein the additive is a peptide, oligopeptide, or protein. In one aspect of this embodiment, the additive is chosen from albumins, immunoglobulins, caseins, hemoglobins, lysozymes, immunoglobins, a-2-macroglobulin, fibronectins, vitronectins, firbinogens, and lipases. In another aspect of this embodiment, the tissue includes tissue of one of coronary vasculature, peripheral vasculature, cerebral vasculature, esophagus, airways, sinus, trachea, colon, biliary tract, urinary tract, prostate, and brain passages. In yet another aspect of this embodiment, the device includes one of a balloon catheter, a perfusion balloon catheter, an infusion catheter, perforated balloon, porous balloon, weeping balloon, a cutting balloon catheter, a scoring balloon catheter, a laser catheter, an atherectomy device, a debulking catheter, a stent, a filter, a stent graft, a covered stent, a patch, a wire, and a valve.

In yet a further embodiment, the present invention relates to a medical device for delivering a therapeutic agent to a tissue, the device comprising a layer overlying an exterior surface of the medical device, the layer comprising a therapeutic agent, an additive, and at least one of an oil, a lipid, and a fatty acid, wherein the additive is an organic acid or an organic acid ester or anhydride. In one aspect of this embodiment, the additive is chosen from acetic acid and anhydride, benzoic acid and anhydride, diethylenetriaminepentaacetic acid dianhydride, ethylenediaminetetraacetic dianhydride, maleic acid and anhydride, succinic acid and anhydride, diglycolic acid and anhydride, glutaric acid and anhydride, ascorbic acid, citric acid, tartaric acid, lactic acid, oxalic acid aspartic acid, nicotinic acid, and 2-pyrrolidone-5-carboxylic acid. In another aspect of this embodiment, the tissue includes tissue of one of coronary vasculature, peripheral vasculature, cerebral vasculature, esophagus, airways, sinus, trachea, colon, biliary tract, urinary tract, prostate, and brain passages. In yet another aspect of this embodiment, the device includes one of a balloon catheter, a perfusion balloon catheter, a cutting balloon catheter, a scoring balloon catheter, a laser catheter, an atherectomy device, a debulking catheter, a stent, a filter, a stent graft, a covered stent, a patch, a wire, and a valve.

Many embodiments of the present invention are particularly useful for treating vascular disease and for reducing stenosis and late luminal loss, or are useful in the manufacture of devices for that purpose.

It is understood that both the foregoing general description and the following detailed description are exemplary and explanatory only and are not restrictive of the present invention as claimed.

DETAILED DESCRIPTION OF EXEMPLARY EMBODIMENTS

Embodiments of the present invention relate to medical devices, including particularly balloon catheters and stents, having a rapid drug-releasing coating and methods for preparing such coated devices. The therapeutic agent according to embodiments of the present invention does not require a delayed or long term release and instead preferably is released in a very short time period, from seconds to minutes, to provide a therapeutic effect upon contact with tissue. An object of embodiments of the present invention is to facilitate rapid and efficient uptake of drug by target tissue during transitory device deployment at a target site.

Figure 1:
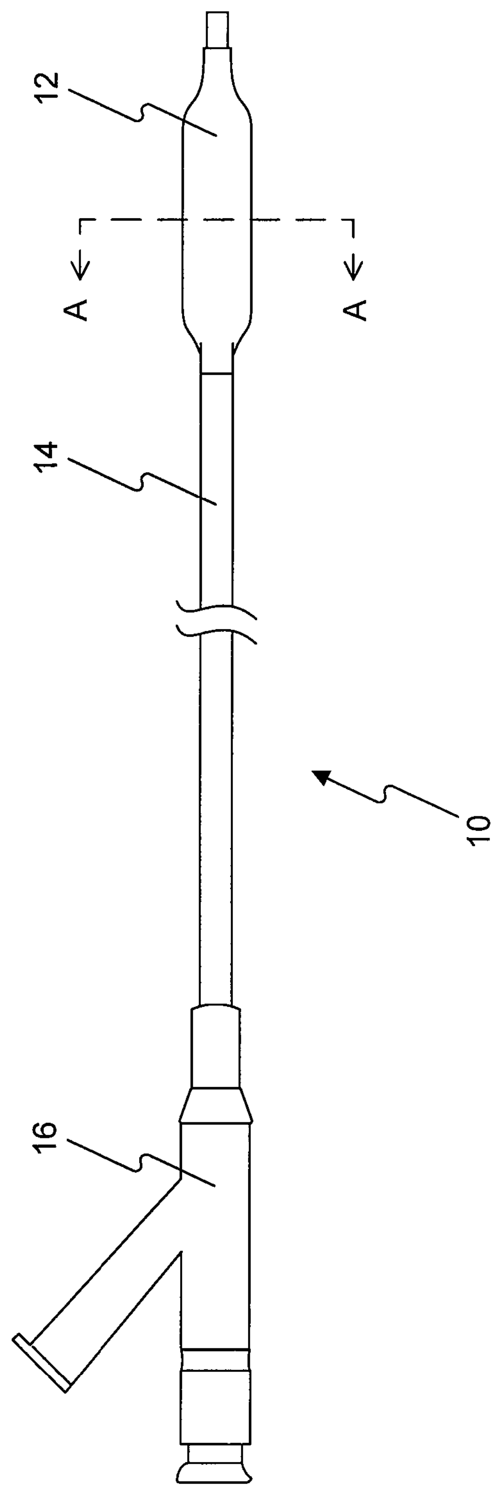
FIG. 1 is a perspective view of an exemplary embodiment of a balloon catheter according to the present invention.

As shown in FIG. 1, in one embodiment, the medical device is a balloon catheter. The balloon catheter may be any suitable catheter for the desired use, including conventional balloon catheters known to one of ordinary skill in the art. For example, balloon catheter 10 may include an expandable, inflatable balloon 12 at a distal end of the catheter 10, a handle assembly 16 at a proximal end of the catheter 10, and an elongate flexible member 14 extending between the proximal and distal ends. Handle assembly 16 may connect to and/or receive one or more suitable medical devices, such as a source of inflation media (e.g., air, saline, or contrast media). Flexible member 14 may be a tube made of suitable biocompatible material and having one or more lumens therein. At least one of the lumens is configured to receive inflation media and pass such media to balloon 12 for its expansion. The balloon catheter may be a rapid exchange or over-the-wire catheter and made of any suitable biocompatible material.

Figure 2A:
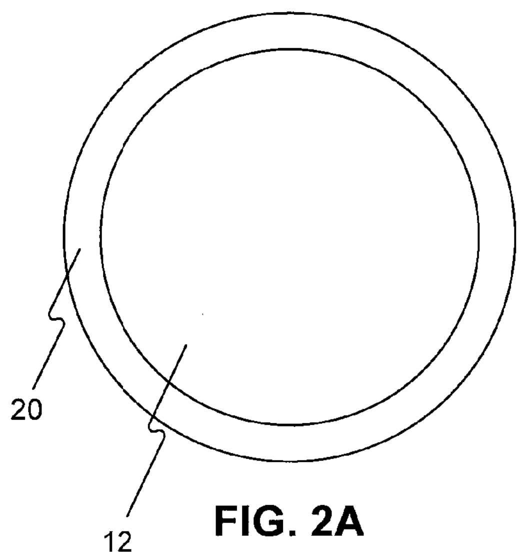
FIGS. 2A-2C are cross-sectional views of different embodiments of the distal portion of the balloon catheter of FIG. 1, taken along line A-A, showing exemplary coating layers.
Figure 2B:
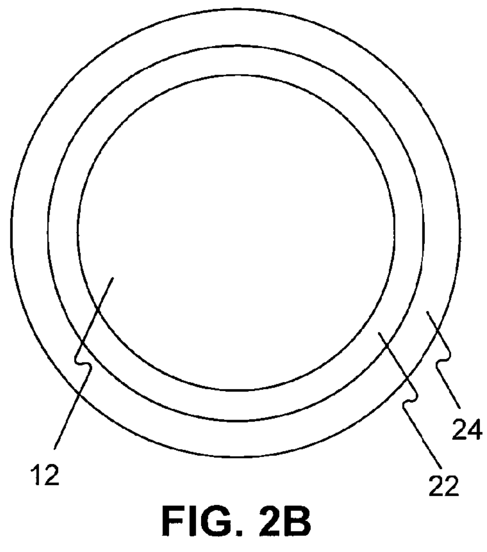

In one embodiment, the present invention provides a medical device for delivering a therapeutic agent to a tissue. The device includes a layer applied to an exterior surface of the medical device, such as a balloon catheter or stent, for example. The layer includes (1) a therapeutic agent, (2) one of an oil, a fatty acid and a lipid, and (3) an additive. For example, as shown in the embodiment depicted in FIG. 2A, the balloon 12 is coated with a layer 20 that includes a therapeutic agent, at least one of an oil, a fatty acid, and a lipid, and an additive. In some embodiments, the layer consists essentially of a therapeutic agent, at least one of an oil, a fatty acid, and a lipid, and an additive, i.e., the layer includes only the therapeutic agent, the at least one of an oil, a fatty acid, and a lipid, and the additive, without any other materially significant components. In some embodiments, the device may optionally include an adherent layer. For example, as shown in the embodiment depicted in FIG. 2B, the balloon 12 is coated with an adherent layer 22. A layer 24 that includes a therapeutic agent, at least one of an oil, a fatty acid, and a lipid, and an additive is overlying the adherent layer. The adherent layer, which is a separate layer underlying the drug coating layer, improves the adherence of the drug coating layer to the exterior surface of the medical device and protects coating integrity. For example, if drug, one of an oil, a fatty acid and a lipid, and additive differ in their adherence to the medical device, the adherent layer may prevent differential loss of components and maintain drug-to-additive and drug-to-the oil, fatty acid or lipid ratio in the coating during transit to a target site for therapeutic intervention. Furthermore, the adherent layer may function to facilitate rapid release of coating layer components off the device surface upon contact with tissues at the target site. In other embodiments, the device may include a top layer. The top layer may reduce loss of the drug layer before it is brought into contact with target tissues, for example during transit of the balloon 12 to the site of therapeutic intervention or during the first moments of inflation of balloon 12 before coating layer 20 is pressed into direct contact with target tissue.

In embodiments of the coatings for medical devices of the present invention, the lipophilic or water-insoluble therapeutic agent is interdispersed in the matrix or dispersion of the additive, such as an additive having a hydrophilic part and a drug affinity part, and the at least one of an oil, a fatty acid and a lipid. The inventor has found that, when the coating of a medical device contains a lipophilic or water-insoluble therapeutic agent and at least one of an oil, a fatty acid and a lipid, but does not contain such an additive, the therapeutic agent cannot elute quickly enough off the surface of the medical device for adequate tissue uptake during a brief deployment time of seconds to minutes, because the lipophilic or water-insoluble drug binds the lipid, fatty acid, or oil and the surface of the balloon too tightly. The inventor has found that, the addition of the additive to the coating, wherein the additive is interspersed or interdispersed with the lipophilic or water-insoluble therapeutic agent and with the at least one of an oil, a fatty acid, and a lipid, dramatically accelerates the elution of the lipophilic or water-insoluble therapeutic agent and the at least one of an oil, a fatty acid and a lipid off the surface of the device and facilitates drug penetration into target tissues. For example, an additive may elute rapidly off the surface of the device when the device is deployed in the aqueous environment of the arterial vasculature, and as the additive having a hydrophilic part and a drug affinity part elutes off the surface of the device, the interdispersed hydrophobic drug and the at least one of an oil, a fatty acid, and a lipid are pulled with it. In this example, the additive functions to disrupt the attraction between lipophilic drug and the at least one of an oil, a fatty acid, and a lipid and the surface of the medical device and facilitates dispersal of the therapeutic agent off the device in an aqueous environment. In some cases it may further accelerate passage of lipophilic drug through the water barrier overlying polar head groups of membrane bilayers of target tissues to the underlying lipid and cellular proteins with which the lipophilic drug has high affinity.

In one embodiment, the concentration density of the at least one therapeutic agent applied to the surface of the medical device is from about 1 to 20 $\mu g/mm^2$, or more preferably from about 2 to 6 $\mu g/mm^2$. In one embodiment, the ratio by weight of the therapeutic agent to the additive in the layer is from about 0.05 to 100, for example, from about 0.1 to 5, from 0.5 to 3, and further for example, from about 0.8 to 1.2. In one embodiment, the ratio by weight of the drug to the at least one of an oil, a fatty acid, and a lipid in the layer is from about 0.05 to 100, for example, from about 0.1 to 5, from 0.5 to 2, and further for example, from about 0.8 to 1.2

In other embodiments, the layer may include a therapeutic agent, at least one of an oil, a fatty acid, and a lipid, and more than one additive. For example, one additive may serve to improve balloon adhesion of another additive or additives, which may be superior at promoting tissue uptake of drug, or may serve to improve balloon adhesion of the at least one of an oil, a fatty acid, and a lipid. Alternatively, one additive may decrease balloon adhesion of another additive or the at least one of an oil, a fatty acid, and a lipid, in order to accelerate elution of the therapeutic agent off the surface of the device during brief deployment at the target site.

In other embodiments, the layer may include at least one therapeutic agent, at least one of an oil, a fatty acid, and a lipid, at least one additive, and at least one polymer carrier for coating of a medical device such as a stent or a balloon. In such embodiments, the therapeutic agent is not encapsulated in polymer particles.

In another embodiment, the device comprises two layers applied to an exterior surface of the medical device, and particularly a balloon catheter, for example. The first layer comprises a therapeutic agent. The first layer may optionally comprise at least one of an oil, a fatty acid, and a lipid, and an additive or additives. The second layer comprises at least one of an oil, a fatty acid, and a lipid, and an additive or additives. The second layer may optionally include at least a therapeutic agent. When the first and second layers both contain a therapeutic agent, the content of the therapeutic agent in the second layer is lower than the content of the therapeutic agent in the first layer. In one embodiment, the second layer is overlying the first layer. In this arrangement, the second layer can prevent drug loss during deployment of the medical device into body passageways, for example, as a balloon catheter traverses the tortuous anatomy to a tissue site in the vasculature.

In another embodiment, the device comprises two layers applied to an exterior surface of the medical device, and particularly a balloon catheter, for example. The first layer comprises a therapeutic agent. The first layer may optionally comprise an additive or additives and may optionally comprise at least one of an oil, a fatty acid, and a lipid. The second layer comprises an additive or additives and at least one of an oil, a fatty acid, and a lipid. The second layer may optionally include at least a therapeutic agent. When the first and second layers both contain a therapeutic agent, the content of the therapeutic agent in the first layer is lower than the content of the therapeutic agent in the second layer. In one embodiment, the second layer is overlying the first layer. This arrangement is useful, for example, in the case of a therapeutic agent that adheres too tightly to the balloon surface to rapidly elute off the balloon when inflated at the target site. In this arrangement, the first layer functions to facilitate rapid release of the bulk of drug, which is in the second layer, off the surface of the device while it is inflated at the target site of therapeutic intervention.

In other embodiments, two or more therapeutic agents are used in combination in the drug-additive layer.

Figure 2C:
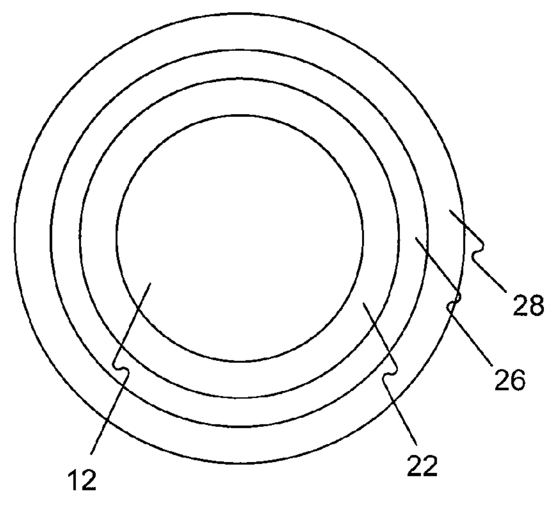

In a further embodiment, the device having a two layer coating may optionally include an adherent layer. The adherent layer does not contain a therapeutic agent. For example, as shown in the embodiment depicted in FIG. 2C, the balloon 12 is coated with an adherent layer 22. A first layer 26 that comprises a therapeutic agent and optionally an additive or additives and optionally at least one of an oil, a fatty acid, and a lipid, is overlying the adherent layer 22. A second layer 28 that comprises an additive, at least one of an oil, a fatty acid, and a lipid, and optionally a therapeutic agent is overlying the first layer 26. The adherent layer improves the adherence of the first layer to the exterior surface of the medical device and protects the integrity of the first layer. For example, if drug and at least one of an oil, a fatty acid, and a lipid and the additive or additives in the first layer differ in their strength of adherence to the medical device, the adherent layer may prevent differential loss of components and maintain drug-to-additive, drug-to at least one of an oil, a fatty acid, and a lipid, and additive-to-additive ratio in the first and second layers during transit to a target site for therapeutic intervention. Furthermore, the adherent layer may function to facilitate rapid elution of coating layer off the device surface upon contact with tissues at the target site. In one embodiment, the first layer, the second layer, and the adherent layer each contain an additive.

Optionally, post-treatment with dimethylsulfoxide (DMSO) or other solvent may be advantageous since DMSO may further enhance penetration and absorption of drug into tissue. DMSO displaces water from the lipid head groups and protein domains of the membrane lipid bilayer of target cells to indirectly loosen the lipid structure, accelerating drug absorption and penetration.

In a further embodiment, the present invention relates to a pharmaceutical composition for treating a diseased body lumen or cavities after surgical or interventional procedures (PTCA, PTA, stent placement, excision of diseased tissue such as cancer, and relieving or treating stenosis), wherein the pharmaceutical composition comprises a therapeutic agent, at least one of an oil, a fatty acid, and a lipid, and an additive, wherein the additive comprises a hydrophilic part and a drug affinity part, wherein the drug affinity part has an affinity to the therapeutic agent by hydrogen bonding and/or charge and/or van der Waals interactions, and wherein the therapeutic agent is not enclosed in micelles or liposomes or encapsulated in polymer particles.

In another embodiment, a method of preventing complications or recurrence of disease (such as cancer or restenosis) after a surgical or interventional procedure such as PTCA, PTA, stent deployment, stenosis or plaque removal by debulking, atherectomy, or laser procedures, the pharmaceutical composition is locally delivered at or near the site of intervention by means of a coated medical device (such as a drug-coated balloon), or by spray, by injection, or by deposition. For example, the pharmaceutical composition may be delivered by spray, injection, balloon or other method of deposition, into cavities created by surgical removal of cancer tissue in order to reduce the risk of recurrence. As another example, a method for delivering the pharmaceutical composition comprises inserting a medical device (such as guide catheter or a drug infusion catheter) into the blood to inject the pharmaceutical composition after a vascular intervention such as PTCA, PTA, or stent placement to prevent restenosis, wherein the pharmaceutical composition comprises a therapeutic agent, at least one of an oil, a fatty acid and a lipid, and an additive, wherein the additive comprises a hydrophilic part and a drug affinity part, wherein the drug affinity part has an affinity to the therapeutic agent by hydrogen bonding and/or charge and/or Van der Waals interactions, and wherein the therapeutic agent is not enclosed in micelles or liposomes or encapsulated in polymer particles.

Many embodiments of the present invention are particularly useful for treating vascular disease and for reducing stenosis and late luminal loss, or are useful in the manufacture of devices for that purpose.

Oil, Fatty Acid and Lipid

The oil, fatty acid, and lipid of embodiments of the present invention are hydrophobic. They are not soluble in water. The lipophilic or water-insoluble therapeutic agents, such as paclitaxel, rapamycin and their analogues, are soluble in the oil, fatty acid, and lipid. Drug release from coatings of water-insoluble drugs and at least one of an oil, a fatty acid, and a lipid that lack the additive, such as a hydrophilic additive, is very slow, in the range of days to months.

The oil, fatty acid, and lipid in embodiments of the inventions herein include, for example, soybean oil, vegetable oil, flower oil, animal oil, marine oil, butterfat, coconut oil, palm oil, olive oil, peanut oil, fish oil, butanoic acid, hexanoic acid, octanoic acid, decanoic acid, dodecanoic acid, tetradecanoic acid, hexadecanoic acid, octadecanoic acid, octadecatrienoic acid, eicosanoic acid, eicosenoic acid, eicosatetraenoic acid, eicosapentaenoic acid, docosahexaenoic acid, tocotrienol, butyric acid, caproic acid, caprylic acid, capric acid, lauric acid, myristic acid, palmitic acid, palmitoleic acid, stearic acid, oleic acid, vaccenic acid, linoleic acid, alpha-linolenic acid, gamma-linolenic acid, behenic acid, erucic acid, lignoceric acid, natural or synthetic phospholipids, mono-, di-, or triacylglycerols, cardiolipin, phosphatidylglycerol, phosphatidic acid, phosphatidylcholine, alpha tocoferol, phosphatidylethanolamine, sphingomyelin, phosphatidylserine, phosphatidylinositol, dimyristoylphosphatidylcholine, dioleoylphosphatidylcholine, dipalmitoylphosphatidylcholine, distearoylphosphatidylcholine, phosphatidylethanolamines phosphatidylglycerols, sphingolipids, prostaglandins, gangliosides, neobee, niosomes and derivatives. There are many other oils, fatty acids, and lipids known in the art that are useful in embodiments of the present invention.

Additive

In embodiments of the present invention, the additive is hydrophilic. It is water-soluble. In embodiments of the present invention, the additive is interdispersed with the lipophilic or water-insoluble drug and at least one of an oil, a fatty acid, and a lipid in the coating of a medical device. In some embodiments, the additive accelerates the elution of the lipophilic or water-insoluble therapeutic agent and the at least one of an oil, a fatty acid, and a lipid off the surface of the device and facilitates drug penetration into target tissues. In some embodiments, the additive may disrupt the hydrophobic attractions between lipophilic drug and the at least one of an oil, a fatty acid, and a lipid and the surface of the medical device. In addition, in some embodiments, as the additive elutes off the surface of the device it may also disperse the therapeutic agent and the at least one of an oil, a fatty acid, and a lipid off the surface of the device and facilitate tissue penetration of the therapeutic agent.

In embodiments of the present invention, the additive has two parts: a hydrophilic part and a drug affinity part. The drug affinity part is a hydrophobic part or has an affinity to the therapeutic agent by hydrogen bonding and/or charge and/or van der Waals interactions. The drug affinity part of the additive may bind the lipophilic drug, such as rapamycin or paclitaxel. Binding or affinity between the drug affinity part of the additive and the drug may be relatively weak. For example, the drug affinity part might comprise hydroxyl groups, which are able to form hydrogen bonds with hydroxyl groups of the drug.

In some embodiments, the additive accelerates diffusion and increases permeation of the drug into tissue. It may facilitate rapid movement of drug off the medical device during deployment at the target site by preventing hydrophobic drug molecules from clumping to each other and to the at least one of an oil, a fatty acid, and a lipid, and to the surface of the device, increasing drug solubility in interstitial spaces, and/or accelerating drug passage through polar head groups to the lipid bilayer of cell membranes of target tissues. In one embodiment, the additives of the present invention have two parts that function together to facilitate rapid release of drug off the device surface and uptake by target tissue during deployment (by accelerating drug contact with tissues for which drug has high affinity) while preventing the premature release of drug from the device surface prior to device deployment at the target site.

In embodiments of the present invention, the therapeutic agent is rapidly released after the medical device is brought into contact with tissue and is readily absorbed. For example, certain embodiments of devices of the present invention include drug coated balloon catheters that deliver a lipophilic anti-proliferative pharmaceutical (such as paclitaxel or rapamycin) to vascular tissue through brief, direct pressure contact at high drug concentration during balloon angioplasty. The lipophilic drug is preferentially retained in target tissue at the delivery site, where it inhibits hyperplasia and restenosis yet allows endothelialization. In these embodiments, coating formulations of the present invention not only facilitate rapid release of drug from the balloon surface and transfer of drug into target tissues during deployment, but also prevent drug from diffusing away from the device during transit through tortuous arterial anatomy prior to reaching the target site and from exploding off the device during the initial phase of balloon inflation, before the drug coating is pressed into direct contact with the surface of the vessel wall.

In embodiments of the present invention, the additive has functional groups that can form hydrogen bonds with drug and with itself. These functional groups include hydroxyl groups, amine groups, amide groups, carbonyl groups, carboxylic acid and anhydrides, ethyl oxide, ethyl glycol, polyethylene glycol, ascorbic acid, amino acid, amino alcohol, glucose, sucrose, sorbitan, glycerol, polyalcohol, phosphates, sulfates, organic salts and their substituted molecules, among others. One or more hydroxyl, carboxyl, acid, amide or amine groups, for example, may be advantageous since they easily displace water molecules that are hydrogen-bound to polar head groups and surface proteins of cell membranes and may function to remove this barrier between hydrophobic drug and cell membrane lipid. These parts can dissolve in water and polar solvents. The therapeutic agent is not enclosed in micelles or liposomes or encapsulated in polymer particles. The additive of embodiments of the present invention facilitates rapid movement of drug off the medical device during deployment and into target tissues.

The additives in embodiments of the present invention are surfactants and chemical compounds with one or more hydroxyl, amino, carbonyl, carboxyl, acid, amide or ester moieties. The surfactants include ionic, nonionic, aliphatic, and aromatic surfactants. The chemical compounds with one or more hydroxyl, amino, carbonyl, carboxyl, acid, amide or ester moieties are chosen from amino alcohols, hydroxyl carboxylic acid and anhydrides, ethyl oxide, ethyl glycols, amino acids, peptides, proteins, sugars, glucose, sucrose, sorbitan, glycerol, polyalcohol, phosphates, sulfates, organic acids, esters, salts, vitamins, and their substituted molecules.

The inventor has performed experiments with some of these surfactants and chemical compounds, combined alone with a lipophilic or water-insoluble therapeutic agent to form the coating of a medical device. In at least certain experiments, a relatively large amount of the therapeutic agent is lost from the coating of the device during its transit to the target site, for example through the arterial vasculature to a stenotic vessel, and with less of the therapeutic agent remaining to provide a therapeutic effect when the coated device finally reaches the target site of therapeutic intervention. The further inclusion of at least one of an oil, a fatty acid, and a lipid in the coating results in less loss of therapeutic agent during transit. In such situations, the addition of the at least one of an oil, fatty acid, and lipid, which tightly binds the lipophilic drug, prevents premature loss of therapeutic agent from the device, but still allows rapid elution when the device is deployed for a brief period of time. Relatively more oil, fatty acid, or lipid may be needed in coatings that include an additive that poorly retains the therapeutic agent on the medical device during transit. Alternatively, in coatings for medical devices that do not include an oil, a fatty acid or a lipid, retention of therapeutic agent during transit may be improved by instead including an additional additive that is relatively hydrophobic.

The inventor has determined experimentally that some of these surfactants when combined alone with a lipophilic or water-insoluble therapeutic agent to form the coating of a medical device, the therapeutic agent release from the balloon catheters was accelerated when the ratio of paclitaxel to the surfactant was in a range of from 0.1 to 0.8. In such situations, a lower amount of surfactant relative to paclitaxel accelerated the drug releasing, and a higher amount of the surfactant reduced the drug releasing. When some of these surfactants are combined alone with a lipophilic or water-insoluble therapeutic agent to form the coating of a medical device, a relatively large amount of the therapeutic agent is lost from the coating of the device during its transit to the target site, for example through the arterial vasculature to a stenotic vessel, with less of the therapeutic agent remaining to provide a therapeutic effect when the coated device finally reaches the target site of therapeutic intervention. The further inclusion of the at least one of an oil, fatty acid, and lipid in the coating with a relatively small amount of the surfactant to slow drug releasing results in less loss of therapeutic agent during transit. In such situations, the addition of the at least one of an oil, a fatty acid, and a lipid, which tightly binds the lipophilic drug, reduces premature loss of therapeutic agent from the device, but still allows rapid elution when the device is deployed for a brief period of time.

As is well known in the art, the terms "hydrophilic" and "hydrophobic" are relative terms. To function as an additive in exemplary embodiments of the present invention, the compound includes polar or charged hydrophilic moieties. In certain embodiments, the hydrophilic additive has a drug affinity part that includes a nonpolar, hydrophobic or lipophilic moiety.

An empirical parameter commonly used in medicinal chemistry to characterize the relative hydrophilicity and hydrophobicity of pharmaceutical compounds is the partition coefficient, P, the ratio of concentrations of unionized compound in the two phases of a mixture of two immiscible solvents, usually octanol and water, such that P=([solute] octanol/[solute]water). Compounds with higher log Ps are more hydrophobic, while compounds with lower log Ps are more hydrophilic. Lipinski's rule suggests that pharmaceutical compounds having log $P<5$ are typically more membrane permeable. For purposes of certain embodiments of the present invention, it is preferable that the additive has log P less than log P of the drug to be formulated (as an example, log P of paclitaxel is 7.4). Furthermore, it is preferable that the additive has log P less than the at least one of an oil, a fatty acid, and a lipid. A greater log P difference between the drug and the additive can facilitate phase separation of drug. For example, if log P of the additive is much lower than log P of the drug, the additive may accelerate the release of drug in an aqueous environment from the at least one of an oil, a fatty acid, and a lipid and from the surface of a device to which drug might otherwise tightly adhere, thereby accelerating drug delivery to tissue during brief deployment at the site of intervention. In certain embodiments of the present invention, log P of the additive is negative. In other embodiments, log P of the additive is less than log P of the drug and less than log P of the at least one of an oil, a fatty acid, and a lipid. While a compound's octanol-water partition coefficient P or log P is useful as a measurement of relative hydrophilicity and hydrophobicity, it is merely a rough guide that may be useful in defining suitable additives for use in embodiments of the present invention.

Suitable additives that can be used in embodiments of the present invention include, without limitation, organic and inorganic pharmaceutical excipients, natural products and derivatives thereof (such as sugars, vitamins, amino acids, peptides, proteins, and fatty acids), low molecular weight oligomers, surfactants (anionic, cationic, non-ionic, and ionic), and mixtures thereof. The following detailed list of additives useful in the present invention is provided for exemplary purposes only and is not intended to be comprehensive. Many other additives may be useful for purposes of the present invention.

Surfactants

The surfactant can be any surfactant suitable for use in pharmaceutical compositions. Such surfactants can be anionic, cationic, zwitterionic or non-ionic. Mixtures of surfactants are also within the scope of the invention, as are combinations of surfactant and other additives. Surfactants often have one or more long aliphatic chains such as fatty acids that may insert directly into lipid bilayers of cell membranes to form part of the lipid structure, while other components of the surfactants loosen the lipid structure and enhance drug penetration and absorption. The contrast agent iopromide does not have these properties.

An empirical parameter commonly used to characterize the relative hydrophilicity and hydrophobicity of surfactants is the hydrophilic-lipophilic balance ("HLB" value). Surfactants with lower HLB values are more hydrophobic, and have greater solubility in oils, while surfactants with higher HLB values are more hydrophilic, and have greater solubility in aqueous solutions. Using HLB values as a rough guide, hydrophilic surfactants are generally considered to be those compounds having an HLB value greater than about 10, as well as anionic, cationic, or zwitterionic compounds for which the HLB scale is not generally applicable. Similarly, hydrophobic surfactants are compounds having an HLB value less than about 10. In certain embodiments of the present invention, a higher HLB value is preferred, since increased hydrophilicity may facilitate release of hydrophobic drug from the surface of the device. In one embodiment, the HLB of the surfactant additive is higher than 10. In another embodiment, the additive HLB is higher than 14. Alternatively, surfactants having lower HLB may be preferred when used to prevent drug loss prior to device deployment at the target site, for example in a top coat over a drug layer that has a very hydrophilic additive.

It should be understood that the HLB value of a surfactant is merely a rough guide generally used to enable formulation of industrial, pharmaceutical and cosmetic emulsions, for example. For many important surfactants, including several polyethoxylated surfactants, it has been reported that HLB values can differ by as much as about 8 HLB units, depending upon the empirical method chosen to determine the HLB value (Schott, J. Pharm. Sciences, 79(1), 87-88 (1990)). Keeping these inherent difficulties in mind, and using HLB values as a guide, surfactants may be identified that have suitable hydrophilicity or hydrophobicity for use in embodiments of the present invention, as described herein.

PEG-Fatty Acids and PEG-Fatty Acid Mono and Diesters

Although polyethylene glycol (PEG) itself does not function as a surfactant, a variety of PEG-fatty acid esters have useful surfactant properties. Among the PEG-fatty acid monoesters, esters of lauric acid, oleic acid, and stearic acid are most useful in embodiments of the present invention. Preferred hydrophilic surfactants include PEG-8 laurate, PEG-8 oleate, PEG-8 stearate, PEG-9 oleate, PEG-10 laurate, PEG-10 oleate, PEG-12 laurate, PEG-12 oleate, PEG-15 oleate, PEG-20 laurate and PEG-20 oleate. The HLB values are in the range of 4-20.

Polyethylene glycol fatty acid diesters are also suitable for use as surfactants in the compositions of embodiments of the present invention. Most preferred hydrophilic surfactants include PEG-20 dilaurate, PEG-20 dioleate, PEG-20 distearate, PEG-32 dilaurate and PEG-32 dioleate. The HLB values are in the range of 5-15.

In general, mixtures of surfactants are also useful in embodiments of the present invention, including mixtures of two or more commercial surfactants as well as mixtures of surfactants with another additive or additives. Several PEG-fatty acid esters are marketed commercially as mixtures or mono- and diesters.

Polyethylene Glycol Glycerol Fatty Acid Esters

Preferred hydrophilic surfactants are PEG-20 glyceryl laurate, PEG-30 glyceryl laurate, PEG-40 glyceryl laurate, PEG-20 glyceryl oleate, and PEG-30 glyceryl oleate.

Alcohol-Oil Transesterification Products

A large number of surfactants of different degrees of hydrophobicity or hydrophilicity can be prepared by reaction of alcohols or polyalcohol with a variety of natural and/or hydrogenated oils. Most commonly, the oils used are castor oil or hydrogenated castor oil, or an edible vegetable oil such as corn oil, olive oil, peanut oil, palm kernel oil, apricot kernel oil, or almond oil. Preferred alcohols include glycerol, propylene glycol, ethylene glycol, polyethylene glycol, sorbitol, and pentaerythritol. Among these alcohol-oil transesterified surfactants, preferred hydrophilic surfactants are PEG-35 castor oil (Incrocas-35), PEG-40 hydrogenated castor oil (Cremophor RH 40), PEG-25 trioleate (TAGAT® TO), PEG-60 corn glycerides (Crovol M70), PEG-60 almond oil (Crovol A70), PEG-40 palm kernel oil (Crovol PK70), PEG-50 castor oil (Emalex C-50), PEG-50 hydrogenated castor oil (Emalex HC-50), PEG-8 caprylic/capric glycerides (Labrasol), and PEG-6 caprylic/capric glycerides (Softigen 767). Preferred hydrophobic surfactants in this class include PEG-5 hydrogenated castor oil, PEG-7 hydrogenated castor oil, PEG-9 hydrogenated castor oil, PEG-6 corn oil (Labrafil® M 2125 CS), PEG-6 almond oil (Labrafil® M 1966 CS), PEG-6 apricot kernel oil (Labrafil® M 1944 CS), PEG-6 olive oil (Labrafil® M 1980 CS), PEG-6 peanut oil (Labrafil® M 1969 CS), PEG-6 hydrogenated palm kernel oil (Labrafil® M 2130 BS), PEG-6 palm kernel oil (Labrafil® M 2130 CS), PEG-6 triolein (Labrafil®b M 2735 CS), PEG-8 corn oil (Labrafil® WL 2609 BS), PEG-20 corn glycerides (Crovol M40), and PEG-20 almond glycerides (Crovol A40).

Polyglyceryl Fatty Acids

Polyglycerol esters of fatty acids are also suitable surfactants for use in embodiments of the present invention. Among the polyglyceryl fatty acid esters, preferred hydrophobic surfactants include polyglyceryl oleate (Plurol Oleique), polyglyceryl-2 dioleate (Nikkol DGDO), polyglyceryl-10 trioleate, polyglyceryl stearate, polyglyceryl laurate, polyglyceryl myristate, polyglyceryl palmitate, and polyglyceryl linoleate. Preferred hydrophilic surfactants include polyglyceryl-10 laurate (Nikkol Decaglyn 1-L), polyglyceryl-10 oleate (Nikkol Decaglyn 1-O), and polyglyceryl-10 mono, dioleate (Caprol® PEG 860), polyglyceryl-10 stearate, polyglyceryl-10 laurate, polyglyceryl-10 myristate, polyglyceryl-10 palmitate, polyglyceryl-10 linoleate, polyglyceryl-6 stearate, polyglyceryl-6 laurate, polyglyceryl-6 myristate, polyglyceryl-6 palmitate, and polyglyceryl-6 linoleate. Polyglyceryl polyricinoleates (Polymuls) are also preferred surfactants.

Propylene Glycol Fatty Acid Esters

Esters of propylene glycol and fatty acids are suitable surfactants for use in embodiments of the present invention. In this surfactant class, preferred hydrophobic surfactants include propylene glycol monolaurate (Lauroglycol FCC), propylene glycol ricinoleate (Propymuls), propylene glycol monooleate (Myverol P-O6), propylene glycol dicaprylate/dicaprate (Captex® 200), and propylene glycol dioctanoate (Captex® 800).

Sterol and Sterol Derivatives

Sterols and derivatives of sterols are suitable surfactants for use in embodiments of the present invention. Preferred derivatives include the polyethylene glycol derivatives. A preferred surfactant in this class is PEG-24 cholesterol ether (Solulan C-24).

Polyethylene Glycol Sorbitan Fatty Acid Esters

A variety of PEG-sorbitan fatty acid esters are available and are suitable for use as surfactants in embodiments of the present invention. Among the PEG-sorbitan fatty acid esters, preferred surfactants include PEG-20 sorbitan monolaurate (Tween-20), PEG-20 sorbitan monopalmitate (Tween-40), PEG-20 sorbitan monostearate (Tween-60), and PEG-20 sorbitan monooleate (Tween-80).

Polyethylene Glycol Alkyl Ethers

Ethers of polyethylene glycol and alkyl alcohols are suitable surfactants for use in embodiments of the present invention. Preferred ethers include PEG-3 oleyl ether (Volpo 3) and PEG-4 lauryl ether (Brij 30).

Sugar and its Derivatives

Sugar derivatives are suitable surfactants for use in embodiments of the present invention. Preferred surfactants in this class include sucrose monopalmitate, sucrose monolaurate, decanoyl-N-methylglucamide, n-decyl-β-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucopyranoside, n-heptyl-β-D-thioglucoside, n-hexyl-β-D-glucopyranoside, nonanoyl-N-methylglucamide, n-noyl-β-D-glucopyranoside, octanoyl-N-methylglucamide, n-octyl-β-D-glucopyranoside, and octyl-β-D-thioglucopyranoside.

Polyethylene Glycol Alkyl Phenols

Several PEG-alkyl phenol surfactants are available, such as PEG-10-100 nonyl phenol and PEG-15-100 octyl phenol ether, Tyloxapol, octoxynol, nonoxynol, and are suitable for use in embodiments of the present invention.

Polyoxyethylene-Polyoxypropylene (POE-POP) Block Copolymers

The POE-POP block copolymers are a unique class of polymeric surfactants. The unique structure of the surfactants, with hydrophilic POE and hydrophobic POP moieties in well-defined ratios and positions, provides a wide variety of surfactants suitable for use in embodiments of the present invention. These surfactants are available under various trade names, including Synperonic PE series (ICI); Pluronic® series (BASF), Emkalyx, Lutrol (BASF), Supronic, Monolan, Pluracare, and Plurodac. The generic term for these polymers is "poloxamer" (CAS 9003-11-6). These polymers have the formula:

$HO(C_2H_4O)_a(C_3H_6O)_b(C_2H_4O)_aH$ where "a" and "b" denote the number of polyoxyethylene and polyoxypropylene units, respectively.

Preferred hydrophilic surfactants of this class include Poloxamers 108, 188, 217, 238, 288, 338, and 407. Preferred hydrophobic surfactants in this class include Poloxamers 124, 182, 183, 212, 331, and 335.

Sorbitan Fatty Acid Esters

Sorbitan esters of fatty acids are suitable surfactants for use in embodiments of the present invention. Among these esters, preferred hydrophobic surfactants include sorbitan monolaurate (Arlacel 20), sorbitan monopalmitate (Span-40), and sorbitan monooleate (Span-80), sorbitan monostearate.

The sorbitan monopalmitate, an amphiphilic derivative of Vitamin C (which has Vitamin C activity), can serve two important functions in solubilization systems. First, it possesses effective polar groups that can modulate the microenvironment. These polar groups are the same groups that make vitamin C itself (ascorbic acid) one of the most water-soluble organic solid compounds available: ascorbic acid is soluble to about 30 wt/wt % in water (very close to the solubility of sodium chloride, for example). And second, when the pH increases so as to convert a fraction of the ascorbyl palmitate to a more soluble salt, such as sodium ascorbyl palmitate.

Ionic Surfactants

Ionic surfactants, including cationic, anionic and zwitterionic surfactants, are suitable hydrophilic surfactants for use in embodiments of the present invention. Preferred ionic surfactants include quaternary ammonium salts, fatty acid salts and bile salts. Specifically, preferred ionic surfactants include benzalkonium chloride, benzethonium chloride, cetylpyridinium chloride, docecyl trimethyl ammonium bromide, sodium docecylsulfates, dialkyl methylbenzyl ammonium chloride, edrophonium chloride, domiphen bromide, dialkylesters of sodium sulfonsuccinic acid, sodium dioctyl sulfosuccinate, sodium cholate, and sodium taurocholate. These quaternary ammonium salts are preferred additives. They can be dissolved in both organic solvents (such as ethanol, acetone, and toluene) and water. This is especially useful for medical device coatings because it simplifies the preparation and coating process and has good adhesive properties. Water insoluble drugs are commonly dissolved in organic solvents.

Chemical Compounds with One or More Hydroxyl, Amino, Carbonyl, Carboxyl, Acid, Amide or Ester Moieties The chemical compounds with one or more hydroxyl, amino, carbonyl, carboxyl, acid, amide or ester moieties include amino alcohols, hydroxyl carboxylic acid, ester, and anhydrides, hydroxyl ketone, hydroxyl lactone, hydroxyl ester, sugar phosphate, sugar sulfate, ethyl oxide, ethyl glycols, amino acids, peptides, proteins, sorbitan, glycerol, polyalcohol, phosphates, sulfates, organic acids, esters, salts, vitamins, combinations of amino alcohols and organic acids, and their substituted molecules. Hydrophilic chemical compounds with one or more hydroxyl, amino, carbonyl, carboxyl, acid, amide or ester moieties having molecular weight less than 5,000-10,000 are preferred in certain embodiments. In other embodiments, molecular weight of the additive with one or more hydroxyl, amino, carbonyl, carboxyl, acid, amide, or ester moieties is preferably less than 1000-5,000, or more preferably less than 750-1,000, or most preferably less than 750. In these embodiments, the molecular weight of the additive is preferred to be less than that of the drug to be delivered. The molecular weight of the additive is preferred to be higher than 80 since molecules with molecular weight less than 80 very easily evaporate and do not stay in the coating of a medical device. Small molecules can diffuse quickly. They can release themselves easily from the delivery balloon, accelerating release of drug, and they can diffuse away from drug when the drug binds tissue of the body lumen.

Fat-Soluble Vitamins and Salts Thereof

Vitamins A, D, E and K in many of their various forms and provitamin forms are considered as fat-soluble vitamins and in addition to these a number of other vitamins and vitamin sources or close relatives are also fat-soluble and have polar groups, and relatively high octanol-water partition coefficients. Clearly, the general class of such compounds has a history of safe use and high benefit to risk ratio, making them useful as additives in embodiments of the present invention. Derivatives of fat-soluble vitamins useful in embodiments of the present invention may easily be obtained via well known chemical reactions with hydrophilic molecules.

The following are examples of fat-soluble vitamin derivatives and/or sources: Alpha-tocopherol, beta-tocopherol, gamma-tocopherol, delta-tocopherol, tocopherol acetate, ergosterol, 1-alpha-hydroxycholecal-ciferol, vitamin D2, vitamin D3, alpha-carotene, beta-carotene, gamma-carotene, vitamin A, fursultiamine, methylolriboflavin, octotiamine, prosultiamine, riboflavine, vintiamol, dihydrovitamin K1, menadiol diacetate, menadiol dibutyrate, menadiol disulfate, menadiol, vitamin K1, vitamin K1 oxide, vitamins K2, and vitamin K—S(II). Folic acid is also of this type; it can be formulated in the free acid form, but it is water-soluble at physiological pH. Other derivatives of fat-soluble vitamins useful in embodiments of the present invention may easily be obtained via well known chemical reactions with hydrophilic molecules.

Water-Soluble Vitamins and their Amphiphilic Derivatives

Vitamins B, C, U, pantothenic acid, folic acid, and some of the menadione-related vitamins/provitamins in many of their various forms are considered water-soluble vitamins. These may also be conjugated or complexed with hydrophobic moieties or multivalent ions into amphiphilic forms having relatively high octanol-water partition coefficients and polar groups. Again, such compounds can be of low toxicity and high benefit to risk ratio, making them useful as additives in embodiments of the present invention. Salts of these can also be useful as additives in the present invention. Examples of water-soluble vitamins and derivatives include, without limitation, acetiamine, benfotiamine, pantothenic acid, cetotiamine, cyclothiamine, dexpanthenol, niacinamide, nicotinic acid, pyridoxal 5-phosphate, nicotinamide ascorbate, riboflavin, riboflavin phosphate, thiamine, folic acid, menadiol diphosphate, menadione sodium bisulfite, menadoxime, vitamin B12, vitamin K5, vitamin K6, vitamin K6, and vitamin U. Also, as mentioned above, folic acid is, over a wide pH range including physiological pH, water-soluble, as a salt.

Compounds in which an amino or other basic group is present can easily be modified by simple acid-base reaction with a hydrophobic group-containing acid such as a fatty acid (especially lauric, oleic, myristic, palmitic, stearic, or 2-ethylhexanoic acid), low-solubility amino acid, benzoic acid, salicylic acid, or an acidic fat-soluble vitamin (such as riboflavin). Other compounds might be obtained by reacting such an acid with another group on the vitamin such as a hydroxyl group to form a linkage such as an ester linkage, etc. Derivatives of a water-soluble vitamin containing an acidic group can be generated in reactions with a hydrophobic group-containing reactant such as stearylamine or riboflavine, for example, to create a compound that is useful in embodiments of the present invention. The linkage of a palmitate chain to vitamin C yields ascorbyl palmitate.

Amino Acids and their Salts

Alanine, arginine, asparagines, aspartic acid, cysteine, cystine, glutamic acid, glutamine, glycine, histidine, proline, isoleucine, leucine, lysine, methionine, phenylalanine, serine, threonine, tryptophan, tyrosine, valine, and derivatives thereof are other useful additives in embodiments of the invention.

Certain amino acids, in their zwitterionic form and/or in a salt form with a monovalent or multivalent ion, have polar groups, relatively high octanol-water partition coefficients, and are useful in embodiments of the present invention. In the context of the present disclosure we take "low-solubility amino acid" to mean an amino acid which has a solubility in unbuffered water of less than about 4% (40 mg/ml). These include Cystine, tyrosine, tryptophan, leucine, isoleucine, phenylalanine, asparagine, aspartic acid, glutamic acid, and methionine.

Amino acid dimers, sugar-conjugates, and other derivatives are also useful. Through simple reactions well known in the art hydrophilic molecules may be joined to hydrophobic amino acids, or hydrophobic molecules to hydrophilic amino acids, to make additional additives useful in embodiments of the present invention.

Catecholamines, such as dopamine, levodopa, carbidopa, and DOPA, are also useful as additives.

Oligopeptides, Peptides and Proteins

Oligopeptides and peptides are useful as additives, since hydrophobic and hydrophilic amino acids may be easily coupled and various sequences of amino acids may be tested to maximally facilitate permeation of tissue by drug.

Proteins are also useful as additives in embodiments of the present invention. Serum albumin, for example, is a preferred additive since it is water-soluble and contains significant hydrophobic parts to bind drug: paclitaxel is 89% to 98% protein-bound after human intravenous infusion, and rapamycin is 92% protein bound, primarily (97%) to albumin. Furthermore, paclitaxel solubility in PBS increases over 20-fold with the addition of BSA. Albumin is naturally present at high concentrations in serum and is thus very safe for human intravascular use.

Other useful proteins include, without limitation, other albumins, immunoglobulins, caseins, hemoglobins, lysozymes, immunoglobins, a-2-macroglobulin, fibronectins, vitronectins, firbinogens, lipases, and the like.

Organic Acids and Their Esters and Anhydrides

Examples are acetic acid and anhydride, benzoic acid and anhydride, diethylenetriaminepentaacetic acid dianhydride, ethylenediaminetetraacetic dianhydride, maleic acid and anhydride, succinic acid and anhydride, diglycolic anhydride, glutaric anhydride, ascorbic acid, citric acid, tartaric acid, lactic acid, oxalic acid aspartic acid, nicotinic acid, 2-pyrrolidone-5-carboxylic acid, and 2-pyrrolidone.

These esters and anhydrides are soluble in organic solvents such as ethanol, acetone, methylethylketone, ethylacetate. The water insoluble drugs can be dissolved in organic solvent with these esters and anhydrides, then coated easily on to the medical device, then hydrolyzed under high pH conditions. The hydrolyzed anhydrides or esters are acids or alcohols, which are water-soluble and can effectively carry the drugs off the device into the vessel walls.

Other chemical compounds with one or more hydroxyl, amine, carbonyl, carboxyl, or ester moieties The additives include amino alcohols, alcohols, amines, acids, amides and hydroxyl acids in both cyclo and linear aliphatic and aromatic groups. Examples are L-ascorbic acid and its salt, D-glucoascorbic acid and its salt, tromethamine, triethanolamine, diethanolamine, meglumine, glucamine, amine alcohols, glucoheptonic acid, glucomic acid, hydroxyl ketone, hydroxyl lactone, gluconolactone, glucoheptonolactone, glucooctanoic lactone, gulonic acid lactone, mannoic lactone, ribonic acid lactone, lactobionic acid, glucosamine, glutamic acid, benzyl alcohol, benzoic acid, hydroxybenzoic acid, propyl 4-hydroxybenzoate, lysine acetate salt, gentisic acid, lactobionic acid, lactitol, sorbitol, glucose, ribose, arabinose, lyxose, xylose, fructose, mannose, glucitol, sugars, sugar phosphates, glucopyranose phosphate, sugar sulphates, sinapic acid, vanillic acid, vanillin, methyl paraben, propyl paraben, diethylene glycol, triethylene glycol, tetraethylene glycol, xylitol, 2-ethoxyethanol, sugars, galactose, glucose, mannose, xylose, sucrose, lactose, maltose, sorbitol, cyclodextrin, (2-hydroxypropyl)-cyclodextrin, acetaminophen, ibuprofen, retinoic acid, lysine acetate, gentisic acid, catechin, catechin gallate, tiletamine, ketamine, propofol, lactic acids, acetic acid, salts of any organic acid and amine described above, polyglycidol, glycerols, and derivatives thereof.

Combinations of additives are also useful for purposes of the present invention.

One embodiment comprises the combination or mixture of two hydrophilic additives, for example, a first additive comprising a surfactant and a second additive comprising a chemical compound with one or more hydroxyl, amine, carbonyl, carboxyl, or ester moieties.

The combination or mixture of a surfactant and a small water-soluble molecule (the chemical compounds with one or more hydroxyl, amine, carbonyl, carboxyl, or ester moieties) has advantages. Formulations comprising mixtures of the two additives with water-insoluble drug are in certain cases superior to either alone. The hydrophobic drugs bind extremely water-soluble small molecules more poorly than they do surfactants. They are often phase separated from the small water-soluble molecules, which can lead to suboptimal coating uniformity and integrity. The water-insoluble drug has Log P higher than both that of the surfactant and that of small water-soluble molecules. However, Log P of the surfactant is typically higher than Log P of the chemical compounds with one or more hydroxyl, amine, carbonyl, carboxyl, or ester moieties. The surfactant has a relatively high Log P (usually above 0) and the water-soluble molecules have low Log P (usually below 0). Some surfactants, when used as additives in embodiments of the present invention, adhere so strongly to the water-insoluble drug and the at least one of an oil, a fatty acid, and a lipid and the surface of the medical device that drug is not able to rapidly release from the surface of the medical device at the target site. On the other hand, some of the water-soluble small molecules (with one or more hydroxyl, amine, carbonyl, carboxyl, or ester moieties) adhere so poorly to the medical device that they release drug before it reaches the target site, for example, into serum during the transit of a coated balloon catheter to the site targeted for intervention. Suprisingly, by adjusting the ratio of the concentrations of the small hydrophilic molecules, the surfactants, and the at least one of an oil, a fatty acid, and a lipid in the coating, the inventor has found that the coating stability during transit and rapid drug release when inflated and pressed against tissues of the lumen wall at the target site of therapeutic intervention is superior to a coating comprising any of these components alone. Furthermore, the miscibility and compatibility of the water-insoluble drug and the highly water-soluble molecules is improved by the presence of the surfactant and the at least one of an oil, a fatty acid, and a lipid. The surfactant also improves coating uniformity and integrity by its good adhesion to the drug and to the small molecules. The long chain hydrophobic part of the surfactant binds drug and at least one of an oil, a fatty acid and a lipid tightly, while the hydrophilic part of the surfactant binds well with the water-soluble small molecules.

The surfactants in the mixture or the combination include all of the surfactants described herein for use in embodiments of the invention. The surfactant in the mixture may be chosen from PEG fatty esters, PEG omega-3 fatty esters and alcohols, glycerol fatty esters, sorbitan fatty esters, PEG glyceryl fatty esters, PEG sorbitan fatty esters, sugar fatty esters, PEG sugar esters, Tween 20, Tween 40, Tween 60, Tween 80, p-isononylphenoxypolyglycidol, PEG laurate, PEG oleate, PEG stearate, PEG glyceryl laurate, PEG glyceryl oleate, PEG glyceryl stearate, polyglyceryl laurate, plyglyceryl oleate, polyglyceryl myristate, polyglyceryl palmitate, polyglyceryl-6 laurate, plyglyceryl-6 oleate, polyglyceryl-6 myristate, polyglyceryl-6 palmitate, polyglyceryl-10 laurate, plyglyceryl-10 oleate, polyglyceryl-10 myristate, polyglyceryl-10 palmitate, PEG sorbitan monolaurate, PEG sorbitan monolaurate, PEG sorbitan monooleate, PEG sorbitan stearate, PEG oleyl ether, PEG laurayl ether, octoxynol, monoxynol, tyloxapol, sucrose monopalmitate, sucrose monolaurate, decanoyl-N-methylglucamide, n-decyl-β-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucopyranoside, n-heptyl-β-D-thioglucoside, n-hexyl-β-D-glucopyranoside, nonanoyl-N-methylglucamide, n-noyl-β-D-glucopyranoside, octanoyl-N-methylglucamide, n-octyl-β-D-glucopyranoside, octyl-β-D-thioglucopyranoside and their derivatives.

The chemical compound with one or more hydroxyl, amine, carbonyl, carboxyl, or ester moieties in the mixture or the combination include all of the chemical compounds with one or more hydroxyl, amine, carbonyl, carboxyl, or ester moieties described in embodiments of the invention. The chemical compound with one or more hydroxyl, amine, carbonyl, carboxyl, or ester moieties in the mixture has at least one hydroxyl group in one of the embodiments in the invention. In one embodiment, more than four hydroxyl groups are preferred. The chemical compound with one or more hydroxyl, amine, carbonyl, carboxyl, or ester moieties in the mixture is chosen from L-ascorbic acid and its salt, D-glucoascorbic acid and its salt, tromethamine, triethanolamine, diethanolamine, meglumine, glucamine, amine alcohols, glucoheptonic acid, glucomic acid, hydroxyl ketone, hydroxyl lactone, gluconolactone, glucoheptonolactone, glucooctanoic lactone, gulonic acid lactone, mannoic lactone, ribonic acid lactone, lactobionic acid, glucosamine, glutamic acid, benzyl alcohol, benzoic acid, hydroxybenzoic acid, propyl 4-hydroxybenzoate, lysine acetate salt, gentisic acid, lactobionic acid, lactitol, sorbitol, glucose, ribose, arabinose, lyxose, xylose, fructose, mannose, glucitol, sugars, sugar phosphates, glucopyranose phosphate, sugar sulphates, sinapic acid, vanillic acid, vanillin, methyl paraben, propyl paraben, diethylene glycol, triethylene glycol, tetraethylene glycol, xylitol, 2-ethoxyethanol, sugars, galactose, glucose, mannose, xylose, sucrose, lactose, maltose, cyclodextrin, sorbitol, (2-hydroxypropyl)-cyclodextrin, acetaminophen, ibuprofen, retinoic acid, lysine acetate, gentisic acid, catechin, catechin gallate, tiletamine, ketamine, propofol, lactic acids, acetic acid, salts of any organic acid and amine described above, polyglycidol, glycerols, and derivatives thereof.

Preferred hydrophilic additives include p-isononylphenoxypolyglycidol, PEG glyceryl oleate, PEG glyceryl stearate, polyglyceryl laurate, plyglyceryl oleate, polyglyceryl myristate, polyglyceryl palmitate, polyglyceryl-6 laurate, plyglyceryl-6 oleate, polyglyceryl-6 myristate, polyglyceryl-6 palmitate, polyglyceryl-10 laurate, plyglyceryl-10 oleate, polyglyceryl-10 myristate, polyglyceryl-10 palmitate, PEG sorbitan monolaurate, PEG sorbitan monolaurate, PEG sorbitan monooleate, PEG sorbitan stearate, octoxynol, monoxynol, tyloxapol, sucrose monopalmitate, sucrose monolaurate, decanoyl-N-methylglucamide, n-decyl-β-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucopyranoside, n-heptyl-β-D-thioglucoside, n-hexyl-β-D-glucopyranoside, nonanoyl-N-methylglucamide, n-noyl-β-D-glucopyranoside, octanoyl-N-methylglucamide, n-octyl-β-D-glucopyranoside, octyl-β-D-thioglucopyranoside; cystine, tyrosine, tryptophan, leucine, isoleucine, phenylalanine, asparagine, aspartic acid, glutamic acid, and methionine (amino acids); cetotiamine; cyclothiamine, dexpanthenol, niacinamide, nicotinic acid and its salt, pyridoxal 5-phosphate, nicotinamide ascorbate, riboflavin, riboflavin phosphate, thiamine, folic acid, menadiol diphosphate, menadione sodium bisulfite, menadoxime, vitamin B12, vitamin K5, vitamin K6, vitamin K6, and vitamin U (vitamins); albumin, immunoglobulins, caseins, hemoglobins, lysozymes, immunoglobins, a-2-macroglobulin, fibronectins, vitronectins, firbinogens, lipases, benzalkonium chloride, benzethonium chloride, docecyl trimethyl ammonium bromide, sodium docecylsulfates, dialkyl methylbenzyl ammonium chloride, and dialkylesters of sodium sulfonsuccinic acid, L-ascorbic acid and its salt, D-glucoascorbic acid and its salt, tromethamine, triethanolamine, diethanolamine, meglumine, glucamine, amine alcohols, glucoheptonic acid, glucomic acid, hydroxyl ketone, hydroxyl lactone, gluconolactone, glucoheptonolactone, glucooctanoic lactone, gulonic acid lactone, mannoic lactone, ribonic acid lactone, lactobionic acid, glucosamine, glutamic acid, benzyl alcohol, benzoic acid, hydroxybenzoic acid, propyl 4-hydroxybenzoate, lysine acetate salt, gentisic acid, lactobionic acid, lactitol, sinapic acid, vanillic acid, vanillin, methyl paraben, propyl paraben, sorbitol, cyclodextrin, (2-hydroxypropyl)-cyclodextrin, acetaminophen, ibuprofen, retinoic acid, lysine acetate, gentisic acid, catechin, catechin gallate, tiletamine, ketamine, propofol, lactic acids, acetic acid, salts of any organic acid and amine described above, polyglycidol, glycerols, and derivatives thereof. (chemical compounds with one or more hydroxyl, amino, carbonyl, carboxyl, or ester moieties). Some of these additives are both water-soluble and organic solvent-soluble. They have good adhesive properties and adhere to the surface of polyamide medical devices, such as balloon catheters. They may therefore be used in the adherent layer, top layer, and/or in the drug layer of embodiments of the present invention. The aromatic and aliphatic groups increase the solubility of water insoluble drugs in the coating solution, and the polar groups of alcohols and acids accelerate drug release from the device and drug permeation into tissue.

Other preferred additives according to embodiments of the invention include the combination of an amino alcohol and an organic acid. Examples are lysine/glutamic acid, lysine acetate, lactobionic acid/meglumine, lactobionic acid/tromethanemine, lactobionic acid/diethanolamine, lactic acid/meglumine, lactic acid/tromethanemine, lactic acid/diethanolamine, gentisic acid/meglumine, gentisic acid/tromethanemine, gensitic acid/diethanolamine, vanillic acid/meglumine, vanillic acid/tromethanemine, vanillic acid/diethanolamine, benzoic acid/meglumine, benzoic acid/tromethanemine, benzoic acid/diethanolamine, acetic acid/meglumine, acetic acid/tromethanemine, and acetic acid/diethanolamine.

Other preferred additives according to embodiments of the invention include hydroxyl ketone, hydroxyl lactone, hydroxyl acid, hydroxyl ester, and hydroxyl amide. Examples are gluconolactone, D-glucoheptono-1,4-lactone, glucooctanoic lactone, gulonic acid lactone, mannoic lactone, erythronic acid lactone, ribonic acid lactone, glucuronic acid, gluconic acid, gentisic acid, lactobionic acid, lactic acid, acetaminophen, vanillic acid, sinapic acid, hydroxybenzoic acid, methyl paraben, propyl paraben, and derivatives thereof.

Other preferred additives that may be useful in embodiments of the present invention include riboflavin, riboflavin-phosphate sodium, Vitamin D3, folic acid (vitamin B9), vitamin 12, diethylenetriaminepentaacetic acid dianhydride, ethylenediaminetetraacetic dianhydride, maleic acid and anhydride, succinic acid and anhydride, diglycolic anhydride, glutaric anhydride, L-ascorbic acid, thiamine, nicotinamide, nicotinic acid, 2-pyrrolidone-5-carboxylic acid, cystine, tyrosine, tryptophan, leucine, isoleucine, phenylalanine, asparagine, aspartic acid, glutamic acid, and methionine.

From a structural point of view, these additives share structural similarities and are compatible with water insoluble drugs (such as paclitaxel and rapamycin). They often contain double bonds such as C═C, C═N, C═O in aromatic or aliphatic structures. These additives also contain amine, alcohol, ester, amide, anhydride, carboxylic acid, and/or hydroxyl groups. They may have an affinity to the therapeutic by hydrogen bonding and/or by charge and/or by van der Waals interactions. They are also useful in the top layer in the coating. Compounds containing one or more hydroxyl, carboxyl, or amine groups, for example, are especially useful as additives since they facilitate drug release from the device surface and easily displace water next to the polar head groups and surface proteins of cell membranes and may thereby remove this barrier to hydrophobic drug permeability. They accelerate movement of a hydrophobic drug off the balloon to the lipid layer of cell membranes and tissues for which it has very high affinity. They may also carry or accelerate the movement of drug off the balloon into more aqueous environments such as the interstitial space, for example, of vascular tissues that have been injured by balloon angioplasty or stent expansion. Additives such as polyglyceryl fatty esters, ascorbic ester of fatty acids, sugar esters, alcohols and ethers of fatty acids have fatty chains that can integrate into the lipid structure of target tissue membranes, carrying drug to lipid structures. Some of the amino acids, vitamins and organic acids have aromatic C═N groups as well as amino, hydroxyl, and carboxylic components to their structure. They have structural parts that can bind or complex with hydrophobic drug, such as paclitaxel or rapamycin, and they also have structural parts that facilitate tissue penetration by removing barriers between hydrophobic drug and lipid structure of cell membranes.

For example, isononylphenylpolyglycidol (Olin-10 G and Surfactant-10G), PEG glyceryl monooleate, sorbitan monolaurate (Arlacel 20), sorbitan monopalmitate (Span-40), sorbitan monooleate (Span-80), sorbitan monostearate, polyglyceryl-10 oleate, polyglyceryl-10 laurate, polyglyceryl-10 palmitate, and polyglyceryl-10 stearate all have more than four hydroxyl groups in their hydrophilic part. These hydroxyl groups have very good affinity for the vessel wall and can displace hydrogen-bound water molecules. At the same time, they have long chains of fatty acid, alcohol, ether and ester that can both complex with hydrophobic drug and integrate into the lipid structure of the cell membranes to form the part of the lipid structure. This deformation or loosening of the lipid membrane of target cells may further accelerate permeation of hydrophobic drug into tissue.

For another example, L-ascorbic acid, thiamine, maleic acids, niacinamide, and 2-pyrrolidone-5-carboxylic acid all have a very high water and ethanol solubility and a low molecular weight and small size. They also have structural components including aromatic C=N, amino, hydroxyl, and carboxylic groups. These structures have very good compatibility with paclitaxel and rapamycin and can increase the solubility of these water-insoluble drugs in water and enhance their absorption into tissues. However, they often have poor adhesion to the surface of medical devices. They are therefore preferably used in combination with other additives in the drug layer and top layer where they are useful to enhance drug absorption. Vitamin D2 and D3 are especially useful because they themselves have anti-restenotic effects and reduce thrombosis, especially when used in combination with paclitaxel.

In one embodiment, the concentration density of the at least one therapeutic agent applied to the surface of the medical device is from about 1 to 20 $\mu g/mm^2$, or more preferably from about 2 to 6 $\mu g/mm^2$. In one embodiment, the concentration of the at least one additive applied to the surface of the medical device is from about 1 to 20 $\mu g/mm^2$. In one embodiment, the concentration of the at least one of an oil, a fatty acid, and a lipid applied to the surface of the medical device is from about 1 to 20 $\mu g/mm^2$. The ratio of additives to drug by weight in the coating layer in embodiments of the present invention is about 20 to 0.05, preferably about 10 to 0.5, or more preferably about 5 to 0.8.

The relative amount of the therapeutic agent, at least one of an oil, a fatty acid and a lipid, and the additive in the coating layer may vary depending on applicable circumstances. The optimal amount of the additive can depend upon, for example, the particular therapeutic agent, the at least one of an oil, a lipid, and a fatty acid, and the additive selected, the critical micelle concentration of the surface modifier, the hydrophilic-lipophilic-balance (HLB) of a surfactant or an additive's the octonol-water partition coefficient (P), the melting point of the additive, the water solubility of the additive and/or therapeutic agent, the surface tension of water solutions of the surface modifier, etc. The oils, fatty acids, and lipids of the present invention are not formed into miscelles, liposomes or particles, and they do not encapsulate the therapeutic agent in particles.

Other considerations will further inform the choice of specific proportions of different additives, oils, lipids, and fatty acids. These considerations include the degree of bioacceptability of the additives and the desired dosage of hydrophobic therapeutic agent to be provided.

Therapeutic Agent

The drugs or biologically active materials, which can be used in embodiments of the present invention, can be any therapeutic agent or substance. The drugs can be of various physical states, e.g., molecular distribution, crystal forms or cluster forms. Examples of drugs that are especially useful in embodiments of the present invention are lipophilic substantially water insoluble drugs, such as paclitaxel, rapamycin, daunorubicin, doxorubicin, lapachone, vitamin D2 and D3 and analogues and derivatives thereof. These drugs are especially suitable for use in a coating on a balloon catheter used to treat tissue of the vasculature.

Other drugs that may be useful in embodiments of the present invention include, without limitation, glucocorticoids (e.g., dexamethasone, betamethasone), hirudin, angiopeptin, aspirin, growth factors, antisense agents, anti-cancer agents, anti-proliferative agents, oligonucleotides, and, more generally, anti-platelet agents, anti-coagulant agents, anti-mitotic agents, antioxidants, anti-metabolite agents, anti-chemotactic, and anti-inflammatory agents.

Also useful in embodiments of the present invention are polynucleotides, antisense, RNAi, or siRNA, for example, that inhibit inflammation and/or smooth muscle cell or fibroblast proliferation.

Anti-platelet agents can include drugs such as aspirin and dipyridamole. Aspirin is classified as an analgesic, antipyretic, anti-inflammatory and anti-platelet drug. Dipyridamole is a drug similar to aspirin in that it has anti-platelet characteristics. Dipyridamole is also classified as a coronary vasodilator. Anti-coagulant agents for use in embodiments of the present invention can include drugs such as heparin, protamine, hirudin and tick anticoagulant protein. Anti-oxidant agents can include probucol. Anti-proliferative agents can include drugs such as amlodipine and doxazosin. Anti-mitotic agents and anti-metabolite agents that can be used in embodiments of the present invention include drugs such as methotrexate, azathioprine, vincristine, vinblastine, 5-fluorouracil, adriamycin, and mutamycin. Antibiotic agents for use in embodiments of the present invention include penicillin, cefoxitin, oxacillin, tobramycin, and gentamicin. Suitable antioxidants for use in embodiments of the present invention include probucol. Additionally, genes or nucleic acids, or portions thereof can be used as the therapeutic agent in embodiments of the present invention. Furthermore, collagen-synthesis inhibitors, such as tranilast, can be used as a therapeutic agent in embodiments of the present invention.

Photosensitizing agents for photodynamic or radiation therapy, including various porphyrin compounds such as porfimer, for example, are also useful as drugs in embodiments of the present invention.

Drugs for use in embodiments of the present invention also include everolimus, somatostatin, tacrolimus, roxithromycin, dunaimycin, ascomycin, bafilomycin, erythromycin, midecamycin, josamycin, concanamycin, clarithromycin, troleandomycin, folimycin, cerivastatin, simvastatin, lovastatin, fluvastatin, rosuvastatin, atorvastatin, pravastatin, pitavastatin, vinblastine, vincristine, vindesine, vinorelbine, etoposide, teniposide, nimustine, carmustine, lomustine, cyclophosphamide, 4-hydroxycyclophosphamide, estramustine, melphalan, ifosfamide, trofosfamide, chlorambucil, bendamustine, dacarbazine, busulfan, procarbazine, treosulfan, temozolomide, thiotepa, daunorubicin, doxorubicin, aclarubicin, epirubicin, mitoxantrone, idarubicin, bleomycin, mitomycin, dactinomycin, methotrexate, fludarabine, fludarabine-5'-dihydrogenphosphate, cladribine, mercaptopurine, thioguanine, cytarabine, fluorouracil, gemcitabine, capecitabine, docetaxel, carboplatin, cisplatin, oxaliplatin, amsacrine, irinotecan, topotecan, hydroxycarbamide, miltefosine, pentostatin, aldesleukin, tretinoin, asparaginase, pegaspargase, anastrozole, exemestane, letrozole, formestane, aminoglutethimide, adriamycin, azithromycin, spiramycin, cepharantin, smc proliferation inhibitor-2w, epothilone A and B, mitoxantrone, azathioprine, mycophenolatmofetil, c-myc-antisense, b-myc-antisense, betulinic acid, camptothecin, lapachol, beta.-lapachone, podophyllotoxin, betulin, podophyllic acid 2-ethylhydrazide, molgramostim (rhuGM-CSF), peginterferon a-2b, lenograstim (r-HuG-CSF), filgrastim, macrogol, dacarbazine, basiliximab, daclizumab, selectin (cytokine antagonist), CETP inhibitor, cadherines, cytokinin inhibitors, COX-2 inhibitor, NFkB, angiopeptin, ciprofloxacin, camptothecin, fluoroblastin, monoclonal antibodies, which inhibit the muscle cell proliferation, bFGF antagonists, probucol, prostaglandins, 1,11-dimethoxycanthin-6-one, 1-hydroxy-11-methoxycanthin-6-one, scopoletin, colchicine, NO donors such as pentaerythritol tetranitrate and syndnoeimines, S-nitrosoderivatives, tamoxifen, staurosporine, beta.-estradiol, a-estradiol, estriol, estrone, ethinylestradiol, fosfestrol, medroxyprogesterone, estradiol cypionates, estradiol benzoates, tranilast, kamebakaurin and other terpenoids, which are applied in the therapy of cancer, verapamil, tyrosine kinase inhibitors (tyrphostines), cyclosporine A, 6-a-hydroxy-paclitaxel, baccatin, taxotere and other macrocyclic oligomers of carbon suboxide (MCS) and derivatives thereof, mofebutazone, acemetacin, diclofenac, lonazolac, dapsone, o-carbamoylphenoxyacetic acid, lidocaine, ketoprofen, mefenamic acid, piroxicam, meloxicam, chloroquine phosphate, penicillamine, hydroxychloroquine, auranofin, sodium aurothiomalate, oxaceprol, celecoxib, .beta.-sitosterin, ademetionine, myrtecaine, polidocanol, nonivamide, levomenthol, benzocaine, aescin, ellipticine, D-24851 (Calbiochem), colcemid, cytochalasin A-E, indanocine, nocodazole, S 100 protein, bacitracin, vitronectin receptor antagonists, azelastine, guanidyl cyclase stimulator tissue inhibitor of metal proteinase-1 and -2, free nucleic acids, nucleic acids incorporated into virus transmitters, DNA and RNA fragments, plasminogen activator inhibitor-1, plasminogen activator inhibitor-2, antisense oligonucleotides, VEGF inhibitors, IGF-1, active agents from the group of antibiotics such as cefadroxil, cefazolin, cefaclor, cefotaxim, tobramycin, gentamycin, penicillins such as dicloxacillin, oxacillin, sulfonamides, metronidazol, antithrombotics such as argatroban, aspirin, abciximab, synthetic antithrombin, bivalirudin, coumadin, enoxaparin, desulphated and N-reacetylated heparin, tissue plasminogen activator, GpIIb/IIIa platelet membrane receptor, factor Xa inhibitor antibody, heparin, hirudin, r-hirudin, PPACK, protamin, prourokinase, streptokinase, warfarin, urokinase, vasodilators such as dipyramidole, trapidil, nitroprussides, PDGF antagonists such as triazolopyrimidine and seramin, ACE inhibitors such as captopril, cilazapril, lisinopril, enalapril, losartan, thiol protease inhibitors, prostacyclin, vapiprost, interferon a, .beta and y, histamine antagonists, serotonin blockers, apoptosis inhibitors, apoptosis regulators such as p65 NF-kB or Bcl-xL antisense oligonucleotides, halofuginone, nifedipine, tranilast, molsidomine, tea polyphenols, epicatechin gallate, epigallocatechin gallate, Boswellic acids and derivatives thereof, leflunomide, anakinra, etanercept, sulfasalazine, etoposide, dicloxacillin, tetracycline, triamcinolone, mutamycin, procainamide, retinoic acid, quinidine, disopyramide, flecamide, propafenone, sotalol, amidorone, natural and synthetically obtained steroids such as bryophyllin A, inotodiol, maquiroside A, ghalakinoside, mansonine, strebloside, hydrocortisone, betamethasone, dexamethasone, non-steroidal substances (NSAIDS) such as fenoprofen, ibuprofen, indomethacin, naproxen, phenylbutazone and other antiviral agents such as acyclovir, ganciclovir and zidovudine, antimycotics such as clotrimazole, flucytosine, griseofulvin, ketoconazole, miconazole, nystatin, terbinafine, antiprozoal agents such as chloroquine, mefloquine, quinine, moreover natural terpenoids such as hippocaesculin, barringtogenol-C21-angelate, 14-dehydroagrostistachin, agroskerin, agrostistachin, 17-hydroxyagrostistachin, ovatodiolids, 4,7-oxycycloanisomelic acid, baccharinoids B1, B2, B3 and B7, tubeimoside, bruceanol A, B and C, bruceantinoside C, yadanziosides N and P, isodeoxyelephantopin, tomenphantopin A and B, coronarin A, B, C and D, ursolic acid, hyptatic acid A, zeorin, iso-iridogermanal, maytenfoliol, effusantin A, excisanin A and B, longikaurin B, sculponeatin C, kamebaunin, leukamenin A and B, 13,18-dehydro-6-a-senecioyloxychaparrin, taxamairin A and B, regenilol, triptolide, moreover cymarin, apocymarin, aristolochic acid, anopterin, hydroxyanopterin, anemonin, protoanemonin, berberine, cheliburin chloride, cictoxin, sinococuline, bombrestatin A and B, cudraisoflavone A, curcumin, dihydronitidine, nitidine chloride, 12-beta-hydroxypregnadien-3,20-dione, bilobol, ginkgol, ginkgolic acid, helenalin, indicine, indicine-N-oxide, lasiocarpine, inotodiol, glycoside 1a, podophyllotoxin, justicidin A and B, larreatin, malloterin, mallotochromanol, isobutyrylmallotochromanol, maquiroside A, marchantin A, maytansine, lycoridicin, margetine, pancratistatin, liriodenine, bisparthenolidine, oxoushinsunine, aristolactam-AII, bisparthenolidine, periplocoside A, ghalakinoside, ursolic acid, deoxypsorospermin, psychorubin, ricin A, sanguinarine, manwu wheat acid, methylsorbifolin, sphatheliachromen, stizophyllin, mansonine, strebloside, akagerine, dihydrousambarensine, hydroxyusambarine, strychnopentamine, strychnophylline, usambarine, usambarensine, berberine, liriodenine, oxoushinsunine, daphnoretin, lariciresinol, methoxylariciresinol, syringaresinol, umbelliferon, afromoson, acetylvismione B, desacetylvismione A, and vismione A and B.

A combination of drugs can also be used in embodiments of the present invention. Some of the combinations have additive effects because they have a different mechanism, such as paclitaxel and rapamycin, paclitaxel and active vitamin D, paclitaxel and lapachone, rapamycin and active vitamin D, rapamycin and lapachone. Because of the additive effects, the dose of the drug can be reduced as well. These combinations may reduce complications from using a high dose of the drug.

Adherent Layer

The adherent layer, which is an optional layer underlying the drug coating layer, improves the adherence of the drug coating layer to the exterior surface of the medical device and protects coating integrity. If drug and additive differ in their adherence to the medical device, the adherent layer may prevent differential loss (during transit) or elution (at the target site) of drug layer components in order to maintain consistent drug-to-additive, drug-to-oil, lipid, or fatty acid-ratio, or drug-to-drug ratio in the drug layer and therapeutic delivery at the target site of intervention. Furthermore, the adherent layer may function to facilitate release of coating layer components which otherwise might adhere too strongly to the device for elution during brief contact with tissues at the target site. For example, in the case where a particular drug binds the medical device tightly, more hydrophilic components are incorporated into the adherent layer in order to decrease affinity of the drug to the device surface.

The adherent layer may also comprise one or more of an oil, a fatty acid, and a lipid and the additives previously described, or other components, in order to maintain the integrity and adherence of the coating layer to the device and to facilitate both adherence of drug and additive components during transit and rapid elution during deployment at the site of therapeutic intervention.

Top Layer

In order to further protect the integrity of the drug layer, an optional top layer may be applied to prevent loss of drug during transit through tortuous anatomy to the target site or during the initial expansion of the device before the coating makes direct contact with target tissue. The top layer may release slowly in the body lumen while protecting the drug layer. The top layer will erode more slowly if it is comprised of more hydrophobic, high molecular weight additives. Surfactants are examples of more hydrophobic structures with long fatty chains, such as Tween 80, Tween 20 and polyglyceryl oleate. High molecular weight additives include polyethylene oxide, polyethylene glycol, and polyvinyl pyrrolidone. Hydrophobic drug itself can act as a top layer component. For example, paclitaxel or rapamycin are hydrophobic. They can be used in the top layer. On the other hand, the top layer cannot erode too slowly or it might actually slow the release of drug during deployment at the target site. Other additives useful in the top coat include additives that strongly interact with drug or with the coating layer, such as L-ascorbic acid and its salt, D-glucoascorbic acid and its salt, tromethamine, triethanolamine, diethanolamine, meglumine, glucamine, amine alcohols, glucoheptonic acid, glucomic acid, gluconolactone, glucosamine, glutamic acid, benzyl alcohol, benzoic acid, hydroxybenzoic acid, propyl 4-hydroxybenzoate, lysine acetate salt, gentisic acid, lactobionic acid, lactitol, sinapic acid, vanillic acid, vanillin, methyl paraben, propyl paraben, cyclodextrin, (2-hydroxypropyl)-cyclodextrin, acetaminophen, ibuprofen, retinoic acid, lysine acetate, gentisic acid, catechin, catechin gallate, tiletamine, ketamine, propofol, lactic acids, acetic acid, salts of any organic acid and amine described above, polyglycidol, glycerols, multiglycerols, and derivatives thereof.

Solvents

Solvents for preparing of the coating layer may include, as examples, any combination of one or more of the following: (a) water, (b) alkanes such as hexane, octane, cyclohexane, and heptane, (c) aromatic solvents such as benzene, toluene, and xylene, (d) alcohols such as ethanol, propanol, and isopropanol, diethylamide, ethylene glycol monoethyl ether, Trascutol, and benzyl alcohol (e) ethers such as dioxane, dimethyl ether and tetrahydrofuran, (f) esters/acetates such as ethyl acetate and isobutyl acetate, (g) ketones such as acetone, acetonitrile, diethyl ketone, and methyl ethyl ketone, and (h) mixture of water and organic solvents such as water/ethanol, water/acetone, water/methanol, water/tetrahydrofuran.

Organic solvents, such as short-chained alcohol, dioxane, tetrahydrofuran, dimethylformamide, acetonitrile, dimethylsulfoxide, etc., are particularly useful and preferred solvents in embodiments of the present invention because these organic solvents generally disrupt collodial aggregates and co-solubilize all the components in the coating solution.

The therapeutic agent, the at least one of an oil, a fatty acid and a lipid, and the additive or additives may be dispersed in, solubilized, or otherwise mixed in the solvent. The weight percent of drug, at least one of an oil, a fatty acid and a lipid, and the additive in the solvent may be in the range of 0.1-80% by weight, preferably 2-20% by weight.

In one embodiment, the ratio of the therapeutic agent to the at least one of an oil, a fatty acid, and a lipid is greater than 0.3. In one embodiment, the ratio of drug to additive is greater than 8 mol %. In one embodiment, the ratio of drug to the at least one of an oil, a fatty acid, and a lipid is greater than 10 mol %. All other things being equal, a higher ratio of drug to the at least one oil, fatty acid, and lipid is advantageous, since it is the drug that delivers the therapeutic effect upon delivery to target tissue.

Another embodiment of the invention relates to a method for preparing a medical device, particularly, for example, a balloon catheter or a stent. First, a coating solution or suspension comprising at least one solvent, at least one therapeutic agent, at least one of an oil, a fatty acid and a lipid, and at least one additive is prepared. In at least one embodiment, the coating solution or suspension includes only these components. The content of the therapeutic agent in the coating solution can be from 0.5-50% by weight based on the total weight of the solution. The content of the additive, or the at least one of an oil, a fatty acid, and a lipid in the coating solution can be from 1-45% by weight, 1 to 40% by weight, or from 1-15% by weight based on the total weight of the solution. The amount of solvent used depends on the coating process and viscosity. It will affect the uniformity of the coating but will be evaporated.

In other embodiments, two or more solvents, two or more therapeutic agents, two or more of the at least one of an oil, a fatty acid, and a lipid, and/or two or more additives may be used in the coating solution.

Various techniques may be used for applying a coating solution to a medical device such as casting, spinning, spraying, dipping (immersing), ink jet printing, electrostatic techniques, and combinations of these processes. Choosing an application technique principally depends on the viscosity and surface tension of the solution. In embodiments of the present invention, dipping and spraying are preferred because it makes it easier to control the uniformity of the thickness of the coating layer as well as the concentration of the therapeutic agent applied to the medical device. Regardless of whether the coating is applied by spraying or by dipping or by another method or combination of methods, each layer is usually deposited on the medical device in multiple application steps in order to control the uniformity and the amount of therapeutic substance and additive applied to the medical device.

Each applied layer is from about 0.1 microns to 15 microns in thickness. The total number of layers applied to the medical device is in a range of from about 2 to 50. The total thickness of the coating is from about 2 to 200 microns.

As discussed above, spraying and dipping are particularly useful coating techniques for use in embodiments of the present invention. In a spraying technique, a coating solution or suspension of an embodiment of the present invention is prepared and then transferred to an application device for applying the coating solution or suspension to a balloon catheter.

An application device that may be used is a paint jar attached to an air brush, such as a Badger Model 150, supplied with a source of pressurized air through a regulator (Norgren, 0-160 psi). When using such an application device, once the brush hose is attached to the source of compressed air downstream of the regulator, the air is applied. The pressure is adjusted to approximately 15-25 psi and the nozzle condition checked by depressing the trigger.

Prior to spraying, both ends of the relaxed balloon are fastened to the fixture by two resilient retainers, i.e., alligator clips, and the distance between the clips is adjusted so that the balloon remained in a deflated, folded, or an inflated or partially inflated, unfolded condition. The rotor is then energized and the spin speed adjusted to the desired coating speed, about 40 rpm.

With the balloon rotating in a substantially horizontal plane, the spray nozzle is adjusted so that the distance from the nozzle to the balloon is about 1-4 inches. First, the coating solution is sprayed substantially horizontally with the brush being directed along the balloon from the distal end of the balloon to the proximal end and then from the proximal end to the distal end in a sweeping motion at a speed such that one spray cycle occurred in about three balloon rotations. The balloon is repeatedly sprayed with the coating solution, followed by drying, until an effective amount of the drug is deposited on the balloon.

In one embodiment of the present invention, the balloon is inflated or partially inflated, the coating solution is applied to the inflated balloon, for example by spraying, and then the balloon is deflated and folded before drying. Drying may be performed under vacuum.

It should be understood that this description of an application device, fixture, and spraying technique is exemplary only. Any other suitable spraying or other technique may be used for coating the medical device, particularly for coating the balloon of a balloon catheter or stent delivery system or stent.

After the medical device is sprayed with the coating solution, the coated balloon is subjected to a drying in which the solvent in the coating solution is evaporated. This produces a coating matrix on the balloon containing the therapeutic agent. One example of a drying technique is placing a coated balloon into an oven at approximately 20° C. or higher for approximately 24 hours. Any other suitable method of drying the coating solution may be used. The time and temperature may vary with particular additives and therapeutic agents.

Optional Post Treatment

After depositing the drug-additive containing layer on the device of certain embodiments of the present invention, dimethyl sulfoxide (DMSO) or other solvent may be applied, by dip or spray or other method, to the finished surface of the coating. DMSO readily dissolves drugs and easily penetrates membranes and may enhance tissue absorption.

It is contemplated that the medical devices of embodiments of the present invention have applicability for treating blockages and occlusions of any body passageways, including, among others, the vasculature, including coronary, peripheral, and cerebral vasculature, the gastrointestinal tract, including the esophagus, stomach, small intestine, and colon, the pulmonary airways, including the trachea, bronchi, bronchioles, the sinus, the biliary tract, the urinary tract, prostate and brain passages. They are especially suited for treating tissue of the vasculature with, for example, a balloon catheter or a stent.

Yet another embodiment of the present invention relates to a method of treating a blood vessel. The method includes inserting a medical device comprising a coating into a blood vessel. The coating layer comprises a therapeutic agent, at least one of an oil, a fatty acid and a lipid, and an additive. In this embodiment, the medical device can be configured as having at least an expandable portion. Some examples of such devices include balloon catheters, perfusion balloon catheters, an infusion catheter such as distal perforated drug infusion catheters, a perforated balloon, spaced double balloon, porous balloon, and weeping balloon, cutting balloon catheters, scoring balloon catheters, self-expanded and balloon expanded-stents, guide catheters, guide wires, embolic protection devices, and various imaging devices.

As mentioned above, one example of a medical device that is particularly useful in the present invention is a coated balloon catheter. A balloon catheter typically has a long, narrow, hollow tube tabbed with a miniature, deflated balloon. In embodiments of the present invention, the balloon is coated with a drug solution. Then, the balloon is maneuvered through the cardiovascular system to the site of a blockage, occlusion, or other tissue requiring a therapeutic agent. Once in the proper position, the balloon is inflated and contacts the walls of the blood vessel and/or a blockage or occlusion. It is an object of embodiments of the present invention to rapidly deliver drug to and facilitate absorption by target tissue. It is advantageous to efficiently deliver drug to tissue in as brief a period of time as possible while the device is deployed at the target site. The therapeutic agent is released into such tissue, for example the vessel walls, in about 0.1 to 30 minutes, for example, or preferably about 0.1 to 10 minutes, or more preferably about 0.2 to 2 minutes, or most preferably, about 0.1 to 1 minutes, of balloon inflation time pressing the drug coating into contact with diseased vascular tissue.

Further, the balloon catheter may be used to treat vascular tissue/disease alone or in combination with other methods for treating the vasculature, for example, photodynamic therapy or atherectomy. Atherectomy is a procedure to remove plaque from arteries. Specifically, atherectomy removes plaque from peripheral and coronary arteries. The medical device used for peripheral or coronary atherectomy may be a laser catheter or a rotablator or a direct atherectomy device on the end of a catheter. The catheter is inserted into the body and advanced through an artery to the area of narrowing. After the atherectomy has removed some of the plaque, balloon angioplasty using the coated balloon of embodiments of the present invention may be performed. In addition, stenting may be performed thereafter, or simultaneous with expansion of the coated balloon as described above. Photodynamic therapy is a procedure where light or irradiated energy is used to kill target cells in a patient. A light-activated photosensitizing drug may be delivered to specific areas of tissue by embodiments of the present invention. A targeted light or radiation source selectively activates the drug to produce a cytotoxic response and mediate a therapeutic anti-proliferative effect.

In some of the embodiments of drug-containing coatings and layers according to the present invention, however, the coating or layer does not include a polymer. And, furthermore, the therapeutic agent is not encapsulated in polymer particles, micelles, or liposomes. As described above, such formulations have significant disadvantages and can inhibit the intended efficient, rapid release and tissue penetration of the agent, especially in the environment of diseased tissue of the vasculature.

Although various embodiments are specifically illustrated and described herein, it will be appreciated that modifications and variations of the present invention are covered by the above teachings and are within the purview of the appended claims without departing from the spirit and intended scope of the invention.

Other than the operating examples, or where otherwise indicated, all numbers expressing quantities of components in a layer, reaction conditions, and so forth used in the specification and claims are to be understood as being modified in all instances by the term "about." Accordingly, unless otherwise indicated to the contrary, the numerical parameters set forth in this specification and attached claims are approximations that may vary depending upon the desired properties sought to be obtained by the present disclosure.

Preparation

The medical device and the coating layers of embodiments of the present invention can be made according to various methods. For example, the coating solution can be prepared by dispersing, dissolving, diffusing, or otherwise mixing all the ingredients, such as a therapeutic agent, at least one of an oil, a fatty acid and a lipid, an additive, and a solvent, simultaneously together. Also, the coating solution can be prepared by sequentially adding each component based on solubility or any other parameters. For example, the coating solution can be prepared by first adding the therapeutic agent and the at least one of an oil, a fatty acid, and a lipid to the solvent and then adding the additive. Alternatively, the additive can be added to the solvent first and then the therapeutic agent, oil, fatty acid, or lipid can be later added. If the solvent used does not sufficiently dissolve the drug, it is preferable to first add the additive to the solvent, then the drug, since the additive will increase drug solubility in the solvent.

In some embodiments, encapsulating liposomes or particles are not formed because the coating solution or dispersion in organic solvent is coated directly onto the medical device, without first drying or evaporating or otherwise removing the organic solvent. That is, there is no reconstitution in aqueous solution of a dried lipid cake or film that might be formed by removal of organic solvent, as is typically done for manufacture of liposomes. Rather, the coating solution or disqersion in organic solvent is coated on the balloon and then dried.

EXAMPLES

The following examples include embodiments of medical devices and coating layers within the scope of the present invention. While the following examples are considered to embody the present invention, the examples should not be interpreted as limitations upon the present invention.

Example 1

Preparation of Coating Solutions

Formulation 1—

50-100 mg (0.06-0.12 mmole) paclitaxel, 1-1.6 ml acetone, 1-1.6 ml ethanol, 0.4-1.0 ml water, 50-200 mg phosphatidylcholine, and 50-200 mg gluconolactone are mixed.

Formulation 2—

50-100 mg (0.06-0.12 mmole) paclitaxel, 1-1.6 ml acetone, 1-1.6 ml ethanol, 0.4-1.0 ml water, 50-200 mg phosphatidylethanolamine, and 50-200 mg gluconolactone are mixed.

Formulation 3—

50-100 mg (0.06-0.12 mmole) paclitaxel, 1-1.6 ml acetone, 1-1.6 ml ethanol, 0.4-1.0 ml water, 50-200 mg dimyristoylphosphatidylcholine, and 50-200 mg gluconolactone are mixed.

Formulation 4—

35-70 mg (0.042-0.084 mmole) paclitaxel, 0.5-1.0 ml acetone, 0.5-1.0 ml ethanol, 5-35 mg Tween 20, and 35-70 mg phosphatidylcholine are mixed.

Formulation 5—

35-70 mg (0.042-0.084 mmole) paclitaxel, 0.4-1.0 ml acetone, 0.4-1.0 ml ethanol, 0.2-0.4 ml water, 35-70 mg sorbitol, and 35-70 mg phosphatidylcholine are mixed.

Formulation 6—

35-70 mg (0.042-0.084 mmole) paclitaxel, 0.4-0.8 ml acetone, 0.4-0.8 ml ethanol, 0.25-0.50 ml water, 35-70 mg lactobionic acid, and 35-70 mg phosphatidylcholine are mixed.

Formulation 7—

50-100 mg (0.06-0.12 mmole) paclitaxel, 1-1.6 ml acetone, 1-1.6 ml ethanol, 0.4-1.0 ml water, 50-200 mg fish oil, and 50-200 mg gluconolactone are mixed.

Formulation 8—

50-100 mg (0.06-0.12 mmole) paclitaxel, 1-1.6 ml acetone, 1-1.6 ml ethanol, 0.4-1.0 ml water, 50-200 mg soybean oil, and 50-200 mg gluconolactone are mixed.

Formulation 9—

50-100 mg (0.06-0.12 mmole) paclitaxel, 1-1.6 ml acetone, 1-1.6 ml ethanol, 0.4-1.0 ml water, 50-200 mg olive oil, and 50-200 mg gluconolactone are mixed.

Formulation 10—

35-70 mg (0.042-0.084 mmole) paclitaxel, 0.5-1.0 ml acetone, 0.5-1.0 ml ethanol, 5-35 mg Tween 20, and 35-70 mg tocotrienol were mixed.

Formulation 11—

35-70 mg (0.042-0.084 mmole) paclitaxel, 0.4-1.0 ml acetone, 0.4-1.0 ml ethanol, 0.2-0.4 ml water, 35-70 mg sorbitol, and 35-70 mg fish oil are mixed.

Formulation 12—

35-70 mg (0.042-0.084 mmole) paclitaxel, 0.4-0.8 ml acetone, 0.4-0.8 ml ethanol, 0.25-0.50 ml water, 35-70 mg lactobionic acid, and 35-70 mg eicosapentaenoic acid are mixed.

Example 2

5 PTCA balloon catheters (3 mm in diameter and 20 mm in length) are folded with three wings under vacuum. The folded balloon under vacuum is sprayed or dipped in a formulation (1-12) in example 1. The folded balloon is then dried, sprayed or dipped again, dried again, and sprayed or dipped again until sufficient amount of drug on the balloon (3 microgram per square mm) is obtained. The coated folded balloon is then rewrapped and sterilized for animal testing.

Example 3

5 PTCA balloon catheters (3 mm in diameter and 20 mm in length) are folded with three wings under vacuum. The folded balloon under vacuum is sprayed or dipped in a formulation (1-6) in example 1. The folded balloon is then dried, sprayed or dipped again in a formulation (7-12), dried, and sprayed or dipped again until sufficient amount of drug on the balloon (3 microgram per square mm) is obtained. The coated folded balloon is then rewrapped and sterilized for animal testing.

Example 4

5 PTCA balloon catheters crimped with bare metal coronary stent (3 mm in diameter and 20 mm in length) are sprayed or dipped in a formulation (1-6) in example 1. The stent delivery system is then dried, sprayed or dipped again in a formulation (7-10), dried and sprayed or dipped again until sufficient amount of drug on the stent and balloon (3 microgram per square mm) is obtained. The coated folded stent delivery system is then sterilized for animal testing.

Example 5

Drug coated balloon catheters and uncoated balloon catheters (as control) are inserted into coronary arteries in pigs. The balloon is over dilated (1:1.2), and the inflated balloon is held in the vessel for 60 seconds to release drug and additive, then deflated and withdrawn from the pig. The animals are angiographed after 3 days, 31 days, 3 months, 6 months, 9 months and 12 months. The amount of drug in the artery tissues of the sacrificed animal is measured after 60 minutes, 3 days, 31 days, 3 months, 6 months, 9 months and 12 months.

Example 6

5 coronary stents (3 mm in diameter and 18 mm in length) are spray or dip coated with the formulation (1-12) in example 1. The stents are then dried, sprayed or dipped again, and dried again until a sufficient amount of drug on the stent (3 microgram per square mm) is obtained. The coated stent is then crimped on PTCA balloon catheters (3 mm in diameters and 20 mm in length). The coated stents with balloon catheters are then sterilized for animal testing.

Example 7

The drug coated stent and uncoated stent (as control) are inserted into coronary arteries in pigs, then the balloon is over dilated (1:1.2). The stent is implanted and drug and additive released, and the balloon is deflated and withdrawn from the pig. The animals are then angiographed after 5, 30, 60 minutes, 3 days, 31 days, 3 months, 6 months, 9 months and 12 months. The amount of drug in the artery tissues of the sacrificed animal is measured 60 minutes, 1 day, 3 days, 31 days, 3 months, 6 months, 9 months and 12 months.

Example 8

5 PTCA balloon catheters are sprayed or dipped in the formulation (1-12) in example 1, dried, and sprayed or dipped and dried again until sufficient amount of drug on balloon is obtained (3 microgram per square mm). A bare metal coronary stent (3 mm in diameter and 20 mm in length) is crimped on each coated balloon. The coated balloons with crimped bare metal stents are then wrapped and sterilized for animal test.

Example 9

5 PTCA balloon catheters are sprayed or dipped in a formulation (1-6) in example 1, dried, and sprayed or dipped again in a formulation (7-12). Balloons are then dried and sprayed or dipped again until sufficient amount of drug on the balloon (3 microgram per square mm) is obtained. A bare metal coronary stent (3 mm in diameter and 20 mm in length) is crimped on each coated balloon. The coated balloons with crimped bare metal stents are then wrapped and sterilized for animal test.

Example 10

The drug coated balloon-expandable bare metal stent of Examples 8 and 9 and plain balloon-expandable bare metal stent (as control) are inserted into coronary arteries in pigs, and the balloon is over dilated (1:1.2). Stent is implanted, and the balloon is held inflated for 60 seconds to release drug and additive, and the balloon is deflated and withdraw from the pig. The animals are then angiographed after 5, 30, 60 minutes, 3 days, 31 days, 3 months, 6 months, 9 months and 12 months. The amount of drug in the artery tissues of the sacrificed animal is measured after 60 minutes, 1 day, 3 days, 31 days, 3 months, 6 months, 9 months and 12 months.

Example 11

The drug coated balloon catheters and uncoated balloon catheters (as control) are inserted via a bronchoscope into the pulmonary airway in pigs. The balloon was dilated, and the inflated balloon is held expanded in the lumen for 60 seconds to release drug and additive. The balloon is deflated and withdrawn from the pig. The animals are then examined bronchoscopically and tissues samples are taken for pathology and quantification of drug uptake after 3 days, 31 days, 3 months, 6 months, 9 months and 12 months.

Example 12

The uncoated stent delivery catheters are inserted into the vascular lumen in pigs. The balloon is dilated, the stent is deployed and the deflated balloon is then withdrawn. The pharmaceutical formulation (1-12) of example 1 (10-100 ml) are injected (about 5-15 mg drug per pig) at the site of stent implantation. The drug is then absorbed by injured tissue. The animals are then examined and tissues samples are taken for pathology.

Example 13

The diseased tissue (breast cancer or prostate or atheroma or stenosis) is removed surgically from a human body. The pharmaceutical formulation 1-12 of example 1 (10-100 ml) is then injected into or onto the surgical cavities created by the surgical intervention (about 5-20 mg drug). The local drug delivery included injection by long needle, guide catheters, introducer shealth, drug infusion tube and other drug delivery catheters. The drug is then absorbed by tissue at the target site.

Example 14

6 PTCA balloon catheters (3.5 and 3.0 mm in diameter and 20 mm in length) are inflated at 1-3 atm. The inflated balloon is loaded with a formulation (1-12) in example 1. A sufficient amount of drug on the balloon (3 microgram per square mm) is obtained. The inflated balloon is folded, and then dried. The coated folded balloon is then rewrapped and sterilized for animal testing.

The coated PTCA balloon catheter is inserted into a target site in the coronary vasculature (LAD, LCX and RCA) of a 25-45 pound pig. The balloon is inflated to about 12 atm. The overstretch ratio (the ratio of balloon diameter to vessel diameter) is about 1.15-1.20. The drug is delivered into the target tissue during 30-60 seconds of inflation. The balloon catheter is then deflated and is withdrawn from the animal body. The target blood vessel is harvested 0.25-24 hours after the procedure. The drug content in the target tissue and the residual drug remaining on the balloon is analyzed by tissue extraction and HPLC.

In some of these animal studies, a stent is crimped on the drug coated balloon catheters prior to deployment. In chronic animal tests, angiography is performed before and after all interventions and at 28-35 days after the procedure. Luminal diameters are measured and late lumen loss is calculated. Late lumen loss is the difference between the minimal lumen diameter measured after a period of follow-up time (usually weeks to months after an intervention, such as angioplasty and stent placement in the case of this example) and the minimal lumen diameter measured immediately after the intervention. Restenosis may be quantified by the diameter stenosis, which is the difference between the mean lumen diameters at follow-up and immediately after the procedure divided by the mean lumen diameter immediately after the procedure.

What is claimed is:

1. A medical device for delivering a therapeutic agent to a tissue, the medical device comprising a coating layer overlying an exterior surface of the medical device, the coating layer comprising:

a hydrophobic therapeutic agent chosen from paclitaxel, rapamycin, and combinations thereof;

at least one water-soluble first additive chosen from PEG sorbitan fatty esters, gluconolactone, lactobionic acid, and combinations thereof; and at least one water-insoluble second additive chosen from phosphatidylcholine, phosphatidylethanolamine, dimyristoylphosphatidylcholine, and combinations thereof.

2. The medical device according to claim 1, wherein the tissue includes tissue of one of coronary vasculature, peripheral vasculature, cerebral vasculature, esophagus, airways, sinus, trachea, colon, biliary tract, urinary tract, prostate, and brain passages.

3. The medical device according to claim 1, wherein the medical device is chosen from a laser catheter, an atherectomy device, a debulking catheter, a stent, a filter, a stent graft, a covered stent, a patch, a wire, and a valve.

4. The medical device according to claim 1, wherein the therapeutic agent in the coating layer is in combination with a second therapeutic agent, and wherein the second therapeutic agent is chosen from beta-lapachone and biologically active vitamin D.

5. The medical device of claim 1, wherein the at least one water-soluble first additive is selected from the group consisting of PEG sorbitan monolaurates, PEG sorbitan monooleates, gluconolactone, lactobionic acid, and combinations thereof.

6. The medical device of claim 1, wherein the at least one water-soluble first additive is selected from the group consisting of PEG-20 sorbitan monolaurate, gluconolactone, lactobionic acid, and combinations thereof.

7. The medical device of claim 1, wherein the at least one water-soluble first additive is selected from the group consisting of PEG-20 sorbitan monolaurate, gluconolactone, and combinations thereof.

8. The medical device of claim 7, wherein the hydrophobic therapeutic agent is paclitaxel.

9. The medical device of claim 1, wherein:

the at least one water-soluble first additive is gluconolactone.

10. The medical device of claim 9, wherein the hydrophobic therapeutic agent is paclitaxel.

11. The medical device of claim 1, wherein:

the at least one water-soluble first additive is lactobionic acid; and the at least one water-insoluble second additive is phosphatidylcholine.

12. The medical device of claim 11, wherein the hydrophobic therapeutic agent is paclitaxel.

13. The medical device of claim 1, wherein:

the at least one water-soluble first additive is PEG-20 sorbitan monolaurate; and the at least one water-insoluble second additive is phosphatidylcholine.

14. The medical device of claim 13, wherein the hydrophobic therapeutic agent is paclitaxel.

15. The medical device of claim 1, wherein the coating layer consists essentially of the hydrophobic therapeutic agent, the water-soluble first additive, and the water-insoluble second additive.

16. A medical device for delivering a therapeutic agent to a tissue, the medical device comprising a coating layer overlying an exterior surface of the medical device, the coating layer comprising:

a hydrophobic therapeutic agent selected from the group consisting of paclitaxel, rapamycin, and combinations thereof;

at least one water-soluble first additive selected from the group consisting of PEG sorbitan fatty esters, gluconolactone, lactobionic acid, and combinations thereof; and at least one water-insoluble second additive selected from the group consisting of soybean oil, vegetable oil, flower oil, coconut oil, palm oil, olive oil, fish oil, butanoic acid, hexanoic acid, octanoic acid, decanoic acid, dodecanoic acid, tetradecanoic acid, hexadecanoic acid, octadecanoic acid, octadecatrienoic acid, eicosanoic acid, eicosenoic acid, eicosatetraenoic acid, eicosapentaenoic acid, docosahexaenoic acid, tocotrienol, butyric acid, caproic acid, caprylic acid, capric acid, lauric acid, myristic acid, palmitic acid, palmitoleic acid, stearic acid, oleic acid, vaccenic acid, linoleic acid, alpha-linolenic acid, gamma-linolenic acid, behenic acid, erucic acid, lignoceric acid, and combinations thereof.

17. The medical device of claim 16, wherein:

the hydrophobic therapeutic agent is paclitaxel;

the at least one water-soluble first additive is gluconolactone; and the at least one water-insoluble second additive is selected from the group consisting of fish oil, soybean oil, and olive oil.

18. The medical device of claim 16, wherein:

the hydrophobic therapeutic agent is paclitaxel;

the at least one water-soluble first additive is lactobionic acid; and the at least one water-insoluble second additive is eicosapentaenoic acid.

19. The medical device of claim 16, wherein:

the hydrophobic therapeutic agent is paclitaxel;

the at least one water-soluble first additive is PEG-20 sorbitan monolaurate; and the at least one water-insoluble second additive is tocotrienol.

20. The medical device of claim 16, wherein the medical device is chosen from a laser catheter, an atherectomy device, a debulking catheter, a stent, a filter, a stent graft, a covered stent, a patch, a wire, and a valve.

* * * * *